United States Patent
Liu et al.

(10) Patent No.: US 11,198,732 B2
(45) Date of Patent: Dec. 14, 2021

(54) FC VARIANTS

(71) Applicant: AMGEN INC., Thousand Oaks, CA (US)

(72) Inventors: Zhi Liu, Shoreline, WA (US); Gunasekaran Kannan, Daly City, CA (US); Wei Yan, Sammamish, WA (US)

(73) Assignee: Amgen Inc., Thousand Oaks, CA (US)

(*) Notice: Subject to any disclaimer, the term of this patent is extended or adjusted under 35 U.S.C. 154(b) by 0 days.

(21) Appl. No.: 16/413,810

(22) Filed: May 16, 2019

(65) Prior Publication Data

US 2020/0010545 A1 Jan. 9, 2020

Related U.S. Application Data

(63) Continuation of application No. 14/005,517, filed as application No. PCT/US2012/029271 on Mar. 15, 2012, now abandoned.

(60) Provisional application No. 61/453,433, filed on Mar. 16, 2011.

(51) Int. Cl.
| | |
|---|---|
| C07K 16/00 | (2006.01) |
| C12P 21/08 | (2006.01) |
| A61K 39/395 | (2006.01) |
| A61K 39/40 | (2006.01) |
| C07K 16/28 | (2006.01) |
| A61K 45/06 | (2006.01) |
| C07K 1/00 | (2006.01) |

(52) U.S. Cl.
CPC ...... *C07K 16/283* (2013.01); *A61K 39/39558* (2013.01); *A61K 45/06* (2013.01); *C07K 16/00* (2013.01); *C07K 2317/31* (2013.01); *C07K 2317/41* (2013.01); *C07K 2317/52* (2013.01); *C07K 2317/524* (2013.01); *C07K 2317/526* (2013.01); *C07K 2317/622* (2013.01); *C07K 2317/72* (2013.01); *C07K 2317/732* (2013.01)

(58) Field of Classification Search
None
See application file for complete search history.

(56) References Cited

U.S. PATENT DOCUMENTS

| 6,737,056 | B1* | 5/2004 | Presta | C07K 16/4291 |
| | | | | 424/133.1 |
| 7,695,936 | B2 | 4/2010 | Carter et al. | |
| 7,820,790 | B2 | 10/2010 | Bakker et al. | |
| 7,951,917 | B1 | 5/2011 | Arathoon et al. | |
| 2003/0078385 | A1 | 4/2003 | Arathoon et al. | |
| 2004/0132101 | A1 | 7/2004 | Lazar et al. | |
| 2005/0079184 | A1 | 4/2005 | Hsing-Chang et al. | |
| 2006/0235208 | A1 | 10/2006 | Lazar et al. | |
| 2007/0105199 | A1 | 5/2007 | Yan et al. | |
| 2008/0089892 | A1 | 4/2008 | Allan et al. | |
| 2008/0112961 | A1 | 5/2008 | Stavenhagen et al. | |
| 2009/0042250 | A1 | 2/2009 | Collingwood et al. | |
| 2009/0311253 | A1 | 12/2009 | Ghayur et al. | |
| 2010/0286374 | A1 | 11/2010 | Kannan et al. | |
| 2012/0244578 | A1 | 9/2012 | Kannan et al. | |

FOREIGN PATENT DOCUMENTS

| EP | 2728002 A1 | 5/2014 |
| WO | 1991/18982 A1 | 12/1991 |
| WO | 2004/063351 A2 | 7/2004 |
| WO | 2006/104989 A2 | 10/2006 |
| WO | 2007/005612 A2 | 1/2007 |
| WO | 2008/145142 A1 | 12/2008 |
| WO | 2009/089004 A1 | 7/2009 |
| WO | 2012/058768 A1 | 5/2012 |

OTHER PUBLICATIONS

Vidarsson et al. Frontiers in Immunology 2014, 5;520:1-17. (Year: 2014).*
Abès and Dutertre et al., "Activating and inhibitory Fcγ receptors in immunotherapy: being the actor or being the target," Expert Review of Clinical Immunology, 5(6): 735-747, 2009.
Carayannopoulos and Capra, "Immunoglobulins Structure and Function," Fundamental Immunology, $3^{rd}$ ed. Paul, ed, Raven Press, pp. 282-286, 1993.
Cosman et al., "High level stable expression of human interleukin-2 receptors in mouse cells generates only low affinity interleukin-2 binding sites," Molecular Immunology, 23(9): 935-941, Sep. 1986.
Cosman et al., Cloning, sequence and expression of human interleukin-2 receptor, Nature, 312: 768-771, Dec. 1984.
Deans et al., "CD20-mediated apoptosis: signaling through lipid rafts," Immunology, 107: 176-182, Oct. 2002.
Dehaij et al., "In vivo Cytotoxicity of Type 1 CD20 Antibodies Critically Depends on Fc Receptor ITAM Signaling," Cancer research, 70(8): 3209-3217, Apr. 2010.
Desmyter et al., "Antigen specificity and high affinity binding provided by one single loop of a camel single-domain antibody," Journal of Biological Chemistry, 276(28): 26285-90; Jul. 2001.
Edelman et al., "The covalent structure of an entire γG immunoglobulin molecule," Proceedings of the National Academy of Sciences of the United States, 63(1): 78-85, May 1969.
Fischer et al., "The pattern of protein synthesis in SV40-infected CV-1 cells," International Journal of Cancer, 5(1): 21-27, 1970.

(Continued)

*Primary Examiner* — Chun W Dahle

(74) *Attorney, Agent, or Firm* — Raymond M. Doss

(57) ABSTRACT

Disclosed are Fc-containing proteins comprising a binding region and a variant Fc region that can elicit one or more immune effector function and/or bind to an Fc receptor more effectively than a similar Fc-containing protein comprising a wild type Fc region. Also disclosed are nucleic acids encoding such Fc-containing proteins, methods for making such proteins, and methods of treatment utilizing such proteins.

10 Claims, 14 Drawing Sheets

Specification includes a Sequence Listing.

(56) References Cited

OTHER PUBLICATIONS

Gluzman et al., "SV40-transformed simian cells support the replication of early SV40 mutants," Cell, 23(1): 175-182, 1981.

Ishiguro et al., "A defucosylated anti-CD317 antibody exhibited enhanced antibody-dependent cellular cytotoxicity against primary myeloma cells in the presence of effectors from patients," Cancer Science, 101: 2227-2223, Oct. 2010.

Karatan et al., "Molecular Recognition Properties of FN3 Monobodies that Bind the Src SH3 Domain," Chemistry & Biology, 11(6): 835-844, Jun. 2004.

Koene et al., "FCγRIIIa-158V/F Polymorphism Influences the Binding of IgG by Natural Killer Cell FCγRIIIa, Independently of the FCγRIIIa-48L/R/H Phenotype," Blood (American Society of Hematology), 90(3): 1109-1114, 1997.

Koide et al., "The Fibronectin type III domain as a scaffold for novel binding proteins," Journal of Molecular Biology, 284(4): 1141-1151, Dec. 1998.

Kolbeck et al., "MEDI-563, a humanized anti-IL-5 receptor @a mAb with enhanced antibody-dependent cell-mediated cytotoxicity function," Journal of Allergy and Clinical Immunology, 125(6): 1344-1353, Jun. 2010.

Liszewski et al., "The Complement System," Fundamental Immunology, 3$^{rd}$ Ed, Raven Press, NY; pp. 917-940,1993.

Luckow et al., "Trends in the Development of Baculovirus Expression Vectors," BioTechnology, 6(1): 47-55, 1988.

Malphettes et al., "Highlight Efficient Deletion of FUT8 I CHO Cell Lines Using Zine-Finger Nucleases Yields Cells That Produce Completely Nonfucosylated Antibodies," Biotechnology and Bioengineering, 106(5): 774-783, 2010.

McMahan et al., "A novel IL-1 receptor, cloned from B cells by mammalian expression, is expressed in many cell types," EMBO Journal, 10(10: 2821-2832, Oct. 1991.

Muyldermans, "Single Domain camel antibodies: current status," J. Biotechnology; Reviews in Molecular Biotechnology, 74: 277-302, 2001.

Nord et al., "A combinatorial library of an α-helical bacterial receptor domain," Protein Engineering, 8(6): 601-608, 1995.

Nuttall et al., "Design and expression of soluble CTLA-4 variable domain as a scaffold for the display of functional polypeptides," Protein Science, 36(2): 217-227, 1999.

Okayama et al., "High-efficiency cloning of full-length cDNA," Molecular and Cellular Biology, 2(2): 161-170, Feb. 1982.

Puck and Kao, "Genetics of Somatic Mammalian Cells, VII. Induction and Isolation of Nutritional Mutants in Chinese Hamster Cells," Proc. N.A.S. USA, 60: 1275-1281, 1958.

Reichert et al., "Development trends for monoclonal antibody cancer therapeutics," Nature Reviews Drug Discovery, 6: 349-356, May 2007.

Richards et al., "Optimization of antibody binding to Fc γ RIIa enhances macrophage phagocytosis of tumor cells," Molecular Cancer Therapeutics, 7(8): 2517-2527, Aug. 2008.

Shields et al., "High resolution mapping of the binding site on human IgG1 for Fc γ RI, Fc γ RII, Fc γ RIII, and FcRn and design of IgG1 variants with improved binding to the Fc γ R," Journal of Biological Chemistry, 276(9): 6591-604; Mar. 2001.

Sondermann et al., "The 3.2-crystal structure of the human IgG1 Fc fragment-Fc γ RIII complex," Nature, 406 i: 6793 p. 267-273; Jul. 2000.

Streltsov et al., "Structure of a shark IgNAR antibody variable domain and modeling of an early-developmental isotype," 14(11): 2901-2909; Nov. 2005.

Warrens et al., "Splicing by overlap extension by PCR using asymmetric amplification: an improved technique for the generation of hybrid proteins of immunological interest," Gene, 186(1): 29-35, Feb. 1997.

Zhang et al., "Transient expression and purification of chimeric heavy chain antibodies," Protein Expression and Purification, 65(1): 77-82, May 2009.

* cited by examiner

```
216        226        236        246        256
 |          |          |          |          |
EPKSCDKTHT CPPCPAPELL GGPSVFLFPP KPKDTLMISR TPEVTCVVVD
               111111 1112 2  3  3 33 33332 2 2 3   22

266        276        286        296        306
 |          |          |          |          |
VSHEDPEVKF NWYVDGVEVH NAKTKPREEQ YNSTYRVVSV LTVLHQDWLN
 2222 2 33 2 332 3332 23332 3322 2 2 2333 3  2 2333332

316        326        336        346        356
 |          |          |          |          |
GKEYKCKVSN KALPAPIEKT ISKAKGQPRE PQVYTLPPSR EEMTKNQVSL
 33 3  3 3 222 2 2223 32323

366        376        386        396        406
 |          |          |          |          |
TCLVKGFYPS DIAVEWESNG QPENNYKTTP PVLDSDGSFF LYSKLTVDKS 416        426        436        446
 |          |          |          |
RWQQGNVFSC SVMHEALHNH YTQKSLSLSP GK
```

Figure 2

FC VARIANTS

CROSS REFERENCE TO RELATED APPLICATIONS

This application is a continuation application of U.S. patent application Ser. No. 14/005,517, filed Dec. 20, 2013; which is a national stage application under 35 U.S.C. § 371 of International Application No. PCT/US2012/029271, having an international filing date of Mar. 15, 2012; which claims priority to U.S. Provisional Application No. 61/453,433, filed Mar. 16, 2011, all of which are incorporated by reference herein in their entireties.

REFERENCE TO THE SEQUENCE LISTING

The present application is being filed along with a Sequence Listing in electronic format. The Sequence Listing is provided as a file entitled A-1618-US-CNT SEQLIST ST25.txt, created May 15, 2019, which is 122 KB in size. The information in the electronic format of the Sequence Listing is incorporated herein by reference in its entirety.

FIELD

The invention relates to polypeptides comprising variant Fc regions that can be heterodimeric and contain amino acid substitutions. The invention further relates to methods of making and using such polypeptides.

BACKGROUND

Therapeutic monoclonal antibodies have been successfully used in various oncologic indications. See, e.g., Reichert et al. (2007), Nature Rev. Drug Discovery 6: 349-356. Efficacy can be dependent upon effector functions of the antibody, such as complement dependent cytotoxicity (CDC), antibody dependent cellular cytotoxicity (ADCC), and/or antibody dependent cell-mediated phagocytosis (ADCP) or upon antibody-induced formation of complexes of the antigen on the tumor cell surface, which can, in some cases, induce apoptosis. See, e.g., Deans et al. (2002), Immunology 107: 176-182. Anti-tumor activity of some antibodies is dependent on the interactions between the therapeutic antibody and Fc gamma receptors (FcγRs). de Haij et al. (2010), Cancer Res. 70(8): 3209-3217. There are a number of different FcγRs, some of which mediate intracellular signaling events leading to cell activation, which leads to cytotoxicity, cytokine release, and phagocytosis/endocytosis followed by antigen presentation. Other FcγRs mediate such activities through accessory proteins. There is a need in the art for antibodies that can more effectively elicit effector functions including ADCC, CDC and/or ADCP.

SUMMARY

Described herein is an Fc-containing protein containing an altered heterodimeric Fc region that can have enhanced effector function compared to a similar protein having an unaltered Fc region. In one embodiment, the invention includes an Fc-containing protein comprising a heterodimeric human IgG Fc region, which comprises an A chain and a B chain, which each comprise from 1 to 10 amino acid substitutions relative to a wild type human Fc polypeptide chain, wherein the Fc-containing protein binds to a human FcγRIIIA-158V and/or FcγRIIIA-158F with a $K_D$ of less than or equal to one fifth of the $K_D$ with which a second protein binds to human FcγRIIIA-158V and/or FcγRIIIA-158F, wherein the second protein is the same as the Fc-containing protein except that it contains a wild type human IgG Fc region without substitutions. The human IgG Fc region can be a human IgG1 or IgG3 Fc region. In some embodiments the Fc-containing protein can bind to human FcγRIIIA-158V and/or FcγRIIIA-158F with a $K_D$ of less than or equal to one tenth or one twentieth of the $K_D$ with which the second protein binds to human FcγRIIIA-158V and/or FcγRIIIA-158F. The IgG Fc region of the Fc-containing protein can be an IgG1 Fc region, and the Fc region can be defucosylated. In some embodiments, the A chain and the B chain of the Fc-containing protein each comprise from 1 to 6 amino acid substitutions relative to a wild type human Fc polypeptide chain. At least one of these substitutions can be a heterodimerizing alteration. The A chain and the B chain can each contain at least two amino acid substitutions that are heterodimerizing alterations and can, for example, contain two or three substitutions that are heterodimerizing alterations. The heterodimerizing alterations can be charge pair mutations, such as the substitutions K392D and K409D in the A chain and the substitutions E356K and D399K in the B chain, or vice versa. Alternatively, the heterodimerizing alterations can be pairs of knobs and holes substitutions.

In further aspects, the Fc-containing protein can comprise an Fc region in which the following substitutions are present: (a) the A chain comprises Q311M and K334V substitutions and the B chain comprises L234Y, E294L, and Y296W substitutions or vice versa; (b) the A chain comprises E233L, Q311M, and K334V substitutions and the B chain comprises L234Y, E294L, and Y296W substitutions or vice versa; (c) the A chain comprises L234I, Q311M, and K334V substitutions and the B chain comprises L234Y, E294L, and Y296W substitutions or vice versa; (d) the A chain comprises S298T and K334V substitutions and the B chain comprises L234Y, K290Y, and Y296W substitutions or vice versa; (e) the A chain comprises A330M and K334V substitutions and the B chain comprises L234Y, K290Y, and Y296W substitutions or vice versa; (f) the A chain comprises A330F and K334V substitutions and the B chain comprises L234Y, K290Y, and Y296W substitutions or vice versa; (g) the A chain comprises Q311M, A330M, and K334V substitutions and the B chain comprises L234Y, E294L, and Y296W substitutions or vice versa; (h) the A chain comprises Q311M, A330F, and K334V substitutions and the B chain comprises L234Y, E294L, and Y296W substitutions or vice versa; (i) the A chain comprises S298T, A330M, and K334V substitutions and the B chain comprises L234Y, K290Y, and Y296W substitutions or vice versa; (j) the A chain comprises S298T, A330F, and K334V substitutions and the B chain comprises L234Y, K290Y, and Y296W substitutions or vice versa; (k) the A chain comprises S239D, A330M, and K334V substitutions and the B chain comprises L234Y, K290Y, and Y296W substitutions or vice versa; (l) the A chain comprises S239D, S298T, and K334V substitutions and the B chain comprises L234Y, K290Y, and Y296W substitutions or vice versa; (m) the A chain comprises a K334V substitution and the B chain comprises Y296W and S298C substitutions or vice versa; (n) the A chain comprises a K334V substitution and the B chain comprises L234Y, Y296W, and S298C substitutions or vice versa; (o) the A chain comprises L235S, S239D, and K334V substitutions and the B chain comprises L234Y, K290Y, and Y296W, substitutions or vice versa; (p) the A chain comprises L235S, S239D, and K334V substitutions and the B chain comprises L234Y, Y296W, and S298C substitutions or vice versa; (q) the A chain comprises Q311M and K334V substitutions and the B chain comprises L234Y, F243V, and Y296W substitutions or vice versa; (r) the A chain comprises Q311M and K334V substitutions and the B chain comprises L234Y, K296W, and S298C substitutions or vice versa; (s) the A chain comprises S239D and K334V substitutions and the B chain comprises L234Y, K290Y, and Y296W substitutions or vice versa; (t) the A chain comprises S239D and K334V substitutions and the B chain comprises L234Y, Y296W, and S298C substitutions or vice versa; (u) the A chain comprises F243V and K334V substitutions and the B chain comprises L234Y, K290Y, and Y296W, substitutions or vice versa; (v) the A chain comprises F243V and K334V substitutions and the B chain comprises L234Y, Y296W, and S298C substitutions or vice versa; (w) the A chain comprises E294L and K334V substitutions and the B chain comprises L234Y, K290Y, and Y296W substitutions or vice versa; (x) the A chain comprises E294L and K334V substitutions and the B chain comprises L234Y, Y296W, and S298C substitutions or vice versa; (y) the A chain comprises A330M and K334V substitutions and the B chain comprises L234Y and Y296W substitutions or vice versa; or (z) the A chain comprises A330M and K334V substitutions and the B chain comprises K290Y and Y296W substitutions or vice versa. In some embodiments, the A chain can comprise the amino acid sequence of SEQ ID NO:8, 12, 14, 16, 20, 22, 24, 26, 28, 30, 32, 34, or 37 and the B chain can comprise the amino acid sequence of SEQ ID NO: 10, 18, 39, or 41. In some embodiments, the B chain can comprise the amino acid sequence of SEQ ID NO:8, 12, 14, 16, 20, 22, 24, 26, 28, 30, 32, or 34, and the A chain can comprise the amino acid sequence of SEQ ID NO:8, 10, or 18.

Any of the Fc-containing proteins described above or below can be defucosylated.

The Fc-containing protein can comprise one of the following combinations of amino acid sequences: SEQ ID NO: 8 and SEQ ID NO:10; SEQ ID NO: 16 and SEQ ID NO:18; SEQ ID NO: 12 and SEQ ID NO:10; SEQ ID NO: 14 and SEQ ID NO:10; SEQ ID NO: 20 and SEQ ID NO:18; SEQ ID NO: 22 and SEQ ID NO:18; SEQ ID NO: 24 and SEQ ID NO:10; SEQ ID NO: 26 and SEQ ID NO:10; SEQ ID NO: 28 and SEQ ID NO:18; SEQ ID NO: 30 and SEQ ID NO:18; SEQ ID NO: 32 and SEQ ID NO:18; SEQ ID NO: 34 and SEQ ID NO:18; SEQ ID NO:37 and SEQ ID NO:39; or SEQ ID NO:37 and SEQ ID NO:41.

Any of the Fc-containing proteins described herein can be an antibody or an Fc fusion protein and can be made in a CHO cell, a HEK 293 cell, or NS0 cell. Such an antibody can be a full length human IgG1 antibody, which can be monospecific, bispecific, trispecific or multispecific and/or can be monovalent or multivalent, including bivalent or tetravalent. The Fc-containing protein can bind to one or more target molecules selected from the group consisting of WT1, MUC1, LMP2, EGFRvIII, HER-2/neu, MAGE-A3, NY-ESO-1, PSMA, GM2/GD2 synthase, CEA, MLANA/MART1, gp100, survivin, prostate-specific antigen (PSA), telomerase reverse transcriptase (hTERT), sarcoma translocation breakpoints, EPHA2, prostatic acid phosphatase (PAP), melanoma inhibitor of apoptosis (ML-IAP), α-fetoprotein (AFP), epithelial cell adhesion molecule (EpCAM), ERG, NA17.A2 peptide (VLPDVFIRC), paired box 3 (PAX3), anaplastic lymphoma kinase (ALK), androgen receptor, claudin 3, claudin 4, claudin 6, claudin 9, cyclin B1, polysialic acid, rho-related GTP-binding protein RhoC, v-myc myelocytomatosis viral related oncogene (MYCN), TRP-2, GD3 ganglioside, fucosyl GM1, mesothelin, prostate stem cell antigen (PSCA), MAGE-A1, CYP1B1, PLAC1, GM3, BORIS, tetranectin (TN), ETV6-AML1 (especially peptides including the breakpoint), NY-BR-1, RGS5, SART3, STn, carbonic anhydrase IX, PAX5, proacrosin binding protein sp32 precursor (OY-TES-1), sperm protein 17 (Sp17), LCK, high molecular weight melanoma-associated antigen (HMWMAA, also known as melanoma chondroitin sulfate proteoglycan), AKAP-4, SSX2, XAGE-1, B7H3 (also known as CD276), legumain, TIE2, prostate-associated gene 4 protein (PAGE-4), vascular endothelial growth factor receptor 2 (VEGFR2), protamine 2 (also known as MAD-CT-1), glomulin (also known as FAP), PDGFR-β, SSX2, SSX5, Fos-related antigen 1, CD20, integrin αvβ3, 5T4 oncofetal antigen, CA IX, CD5, CD19, CD22 (also known as Siglec-2), CD30 (also known as TNFRSF8), CD33 (also known as Siglec-3), CD38, CD138, CD40, CD44V6, CD55, CD56 (also known as NCAM), CTLA-4 (also known as CD152), EGFR, GD2, HER2, HLA-DR10 (MHC II), IGF1R, IL-6, sialyl Lewis Y, Mesothelin, TAG-72, TAL6, TRAILR2, VEGF, CD52 (also known as CAM PATH-1), CD4, CD73, CA125 (also known as MUC16), CD66e, CD80 (also known as B7-1), PDGFRβ, prostate specific membrane antigen (PSMA, also known as glutamate carboxypeptidase 2, among many other names), the herpes virus 4 protein LMP2, the human papillomavirus proteins E6 and E7, and the glycoceramide globo H, the α4 subunit of the α4β1 and α4β7 integrins, the α4β7 integrin, BAFF, APRIL, CD2, CD3, CD20, CD52. CD80, CD86, the $C_5$ complement protein, IgE, IL-1β, IL-5, IL-6R, IL-12, IL-23, and tumor necrosis factor α (TNF α). In particular embodiments, the Fc-containing proteins described herein can bind to HER-2/neu or mesothelin or can bind to both CD38 and CD138. CDH19, CDH3, BCMA, and IL13RA2.

In a further embodiment, the invention includes a pharmaceutical composition comprising a therapeutically effective amount of any of the Fc-containing proteins described above and below plus a pharmaceutically acceptable carrier.

In another embodiment, described herein are nucleic acids encoding any of the Fc-containing proteins described above and below plus a host cell containing such nucleic acids. In some embodiments, an A chain and a B chain are encoded by separate nucleic acid molecules, whereas in other embodiments an A chain and a B chain can be encoded on the same nucleic acid molecule. The host cell can be a CHO cell, a HEK 293 cell, or an NS0 cell.

Further, described herein is a method of making an Fc-containing protein comprising a heterodimeric Fc region comprising culturing the host cell under conditions such that the Fc-containing protein will be expressed and, in some embodiments, recovering the polypeptide from the cell mass or the culture medium.

Also described herein is a method of making a pharmaceutical composition comprising an Fc-containing protein containing a heterodimeric Fc region comprising the following steps: (a) culturing a host cell containing one or more nucleic acids encoding a heterodimeric Fc-containing protein as described herein under conditions such that the Fc-containing protein will be expressed; (b) recovering the Fc-containing protein from the cell mass or the culture medium; and (c) formulating the Fc-containing protein with a pharmaceutically acceptable carrier.

Also described herein is a method of making an Fc-containing protein containing a heterodimeric Fc region comprising the following steps: (a) providing a host cell containing one or more nucleic acids encoding an Fc-containing protein comprising a heterodimeric human IgG Fc region and a binding region, wherein the Fc region comprises an A chain and a B chain, which each comprise from 1 to 10 amino acid substitutions relative to a wild type human Fc polypeptide chain, wherein the Fc-containing protein binds to human FcγRIIIA-158F and/or FcγRIIIA-158V with a $K_D$ of less than or equal to one fifth of the $K_D$ with which a second protein binds to human FcγRIIIA-158F or FcγRIIIA-158V, wherein the second protein is the same as the Fc-containing protein except that it contains a wild type human IgG Fc region without substitutions; (b) culturing the host cell containing one or more nucleic acids encoding the heterodimeric Fc-containing protein under conditions such that the Fc-containing protein will be expressed; and (c) recovering the Fc-containing protein from the cell mass or the culture medium. Further, the Fc-containing protein can be formulated with a pharmaceutically acceptable carrier to make a pharmaceutical composition.

In another aspect, described herein is a method for treating cancer comprising administering to a patient in need thereof a therapeutically effective amount of the Fc-containing protein or pharmaceutical composition described above or below, wherein the Fc-containing protein binds to a molecule that is displayed on the cancer cells. A chemotherapeutic agent or a non-chemotherapeutic anti-neoplastic agent can be administered to the patient before, after, or concurrently with administration of the Fc-containing protein. The cancer can be selected from the group consisting of mesothelioma, squamous cell carcinoma, myeloma, osteosarcoma, glioblastoma, glioma, carcinoma, adenocarcinoma, melanoma, sarcoma, acute and chronic leukemia, lymphoma, meningioma, Hodgkin's disease, Sézary syndrome, multiple myeloma, and lung, non-small cell lung, small cell lung, laryngeal, breast, head and neck, bladder, ovarian, skin, prostate, cervical, vaginal, gastric, renal cell, kidney, pancreatic, colorectal, endometrial, esophageal, hepatobiliary, bone, skin, and hematologic cancers, as well as cancers of the nasal cavity and paranasal sinuses, the nasopharynx, the oral cavity, the oropharynx, the larynx, the hypolarynx, the salivary glands, the mediastinum, the stomach, the small intestine, the colon, the rectum and anal region, the ureter, the urethra, the penis, the testis, the vulva, the endocrine system, the central nervous system, and plasma cells.

In another aspect, described herein are uses of the Fc-containing protein or pharmaceutical composition described above or below in the treatment of a human disease, for example autoimmune diseases, asthma, systemic lupus erythematosus, infectious diseases, or cell proliferative diseases such as cancer, or in the manufacture of a medicament, wherein the medicament can be for treating cancer, asthma, systemic lupus erythematosus, or an infectious disease.

BRIEF DESCRIPTION OF THE FIGURES

FIG. 2: The amino acid sequence of a human IgG1 Fc polypeptide. The amino acid sequence of a human IgG1 Fc region, starting with the hinge region and ending with the carboxyl terminus of the $C_H3$ region, is shown in single letter notation and is numbered according to the EU system of Edelman et al. (1969), Proc. Natl. Acad. Sci. 63: 78-85. The amino acids underlined and in boldface type were randomized in constructing the libraries as described in Example 1. Beneath each of these amino acids is a "1," a "2," or a "3," which indicates that DNAs encoding variants at the corresponding site were included in a Tier 1, 2, or 3 library as described in Example 1.

BRIEF DESCRIPTION OF THE SEQUENCE LISTINGS

Figure 1:
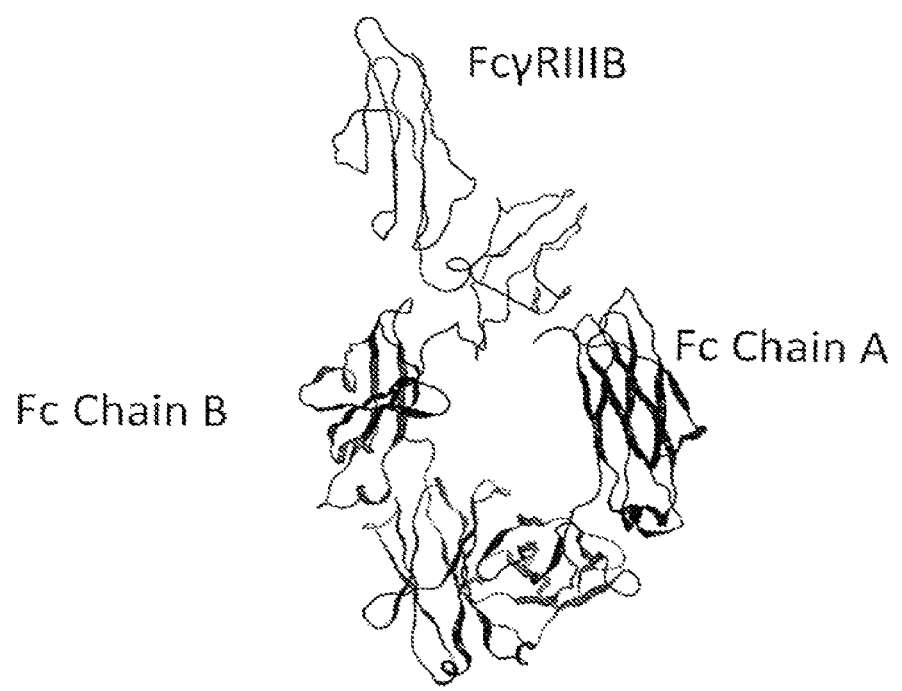
FIG. 1: Diagram of the tertiary structure of FcγRIIIB bound to an Fc region. This figure is a representation of the X-ray crystal structure of the Fc-FcγRIIIB (Protein Data Bank code: 1T83) complex, which includes the extracellular region of FcγRIIIB and a dimeric Fc region. The FcγRIIIB structure is shown in a wire model above. Fc Chain A and Fc Chain B are shown below in ribbon models. The tertiary structures of the extracellular regions of FcγRIIIA and FcγRIIIB are expected to be similar since only five of the 176 amino acids in these two extracellular regions differ. A later-determined structure of an Fc-FcγRIIIA complex (Protein Data Bank code: 3SGK) is very similar to this Fc-FcγRIIIB complex structure.

| Sequence Listing Number | Description of the Sequence |
| --- | --- |
| SEQ ID NO: 1 | Nucleotide sequence encoding a human IgG1 Fc polypeptide chain |
| SEQ ID NO: 2 | Amino acid sequence of a human IgG1 Fc polypeptide chain |
| SEQ ID NO: 3 | Nucleotide sequence encoding a human IgG1 Fc polypeptide chain containing the substitutions K392D and K409D (encoding one Fc polypeptide of variant M04) |
| SEQ ID NO: 4 | Amino acid sequence of the Fc polypeptide chain encoded by SEQ ID NO: 3 |
| SEQ ID NO: 5 | Nucleotide sequence encoding a human IgG1 Fc polypeptide chain containing the substitutions E356K and D399K (encoding one Fc polypeptide of variant M04) |
| SEQ ID NO: 6 | Amino acid sequence of the Fc polypeptide chain encoded by SEQ ID NO: 5 |
| SEQ ID NO: 7 | Nucleotide sequence encoding a human IgG1 Fc polypeptide chain containing the substitutions K392D, K409D, Q311M, and K334V (encoding one Fc polypeptide of variants M75, M77, and M78) |
| SEQ ID NO: 8 | Amino acid sequence of the Fc polypeptide chain encoded by SEQ ID NO: 7 |
| SEQ ID NO: 9 | Nucleotide sequence encoding a human IgG1 Fc polypeptide chain containing the substitutions E356K, D399K, L234Y, E294L, and Y296W (encoding one Fc polypeptide of variants M77, M138, M142, W157, and W160) |
| SEQ ID NO: 10 | Amino acid sequence of the Fc polypeptide chain encoded by SEQ ID NO: 9 |
| SEQ ID NO: 11 | Nucleotide sequence encoding a human IgG1 Fc polypeptide chain containing the substitutions K392D, K409D, E233L, Q311M, and K334V (encoding one Fc polypeptide of variant M138) |
| SEQ ID NO: 12 | Amino acid sequence of the Fc polypeptide chain encoded by SEQ ID NO: 11 |
| SEQ ID NO: 13 | Nucleotide sequence encoding a human IgG1 Fc polypeptide chain containing the substitutions K392D, K409D, L234I, Q311M, and K334V (encoding one Fc polypeptide of variant M142) |
| SEQ ID NO: 14 | Amino acid sequence of the Fc polypeptide chain encoded by SEQ ID NO: 13 |
| SEQ ID NO: 15 | Nucleotide sequence encoding a human IgG1 Fc polypeptide chain containing the substitutions K392D, K409D, S298T, and K334V (encoding one Fc polypeptide of variant W23) |

| Sequence Listing Number | Description of the Sequence |
|---|---|
| SEQ ID NO: 16 | Amino acid sequence of the Fc polypeptide chain encoded by SEQ ID NO: 15 |
| SEQ ID NO: 17 | Nucleotide sequence encoding a human IgG1 Fc polypeptide chain containing the substitutions E356K, D399K, L234Y, K290Y, and Y296W (encoding one Fc polypeptide of variant W23, W141, W144, W165, W168, W187, and W189) |
| SEQ ID NO: 18 | Amino acid sequence of the Fc polypeptide chain encoded by SEQ ID NO: 17 |
| SEQ ID NO: 19 | Nucleotide sequence encoding a human IgG1 Fc polypeptide chain containing the substitutions K392D, K409D, A330M, and K334V (encoding one Fc polypeptide of variant W141) |
| SEQ ID NO: 20 | Amino acid sequence of the Fc polypeptide chain encoded by SEQ ID NO: 19 |
| SEQ ID NO: 21 | Nucleotide sequence encoding a human IgG1 Fc polypeptide chain containing the substitutions K392D, K409D, A330F, and K334V (encoding one Fc polypeptide of variant W144) |
| SEQ ID NO: 22 | Amino acid sequence of the Fc polypeptide chain encoded by SEQ ID NO: 21 |
| SEQ ID NO: 23 | Nucleotide sequence encoding a human IgG1 Fc polypeptide chain containing the substitutions K392D, K409D, Q311M, A330M, and K334V (encoding one Fc polypeptide of variant W157) |
| SEQ ID NO: 24 | Amino acid sequence of the Fc region encoded by SEQ ID NO: 23 |
| SEQ ID NO: 25 | Nucleotide sequence encoding a human IgG1 Fc polypeptide chain containing the substitutions K392D, K409D, Q311M, A330F, and K334V (encoding one Fc polypeptide of variant W160) |
| SEQ ID NO: 26 | Amino acid sequence of the Fc polypeptide chain encoded by SEQ ID NO: 25 |
| SEQ ID NO: 27 | Nucleotide sequence encoding a human IgG1 Fc polypeptide chain containing the substitutions K392D, K409D, S298T, A330M, and K334V (encoding one Fc polypeptide of variant W165) |
| SEQ ID NO: 28 | Amino acid sequence of the Fc polypeptide chain encoded by SEQ ID NO: 27 |
| SEQ ID NO: 29 | Nucleotide sequence encoding a human IgG1 Fc polypeptide chain containing the substitutions K392D, K409D, S298T, A330F, and K334V (encoding one Fc polypeptide of variant W168) |
| SEQ ID NO: 30 | Amino acid sequence of the Fc polypeptide chain encoded by SEQ ID NO: 29 |
| SEQ ID NO: 31 | Nucleotide sequence encoding a human IgG1 Fc polypeptide chain containing the substitutions K392D, K409D, S239D, A330M, and K334V (encoding one Fc polypeptide of variant W187) |
| SEQ ID NO: 32 | Amino acid sequence of the Fc polypeptide chain encoded by SEQ ID NO: 31 |
| SEQ ID NO: 33 | Nucleotide sequence encoding a human IgG1 Fc polypeptide chain containing the substitutions K392D, K409D, S239D, S298T, and K334V (encoding one Fc polypeptide of variant W189) |
| SEQ ID NO: 34 | Amino acid sequence of the Fc polypeptide chain encoded by SEQ ID NO: 33 |
| SEQ ID NO: 35 | Amino acid sequence of the mature human FcγRIIIA-158V protein |
| SEQ ID NO: 36 | Nucleotide sequence encoding a human IgG1 Fc polypeptide chain containing the substitutions A330M, K334V, K392D, and K409D (encoding a variant Fc polypeptide chain that is part of both W117 and W125) |
| SEQ ID NO: 37 | Amino acid sequence of the Fc polypeptide chain encoded by SEQ ID NO: 36 |
| SEQ ID NO: 38 | Nucleotide sequence encoding a human IgG1 Fc polypeptide chain containing the substitutions L234Y, Y296W, E356K, and D399K (encoding one Fc polypeptide of variant W117) |
| SEQ ID NO: 39 | Amino acid sequence of the Fc polypeptide chain encoded by SEQ ID NO: 38 |
| SEQ ID NO: 40 | Nucleotide sequence encoding a human IgG1 Fc polypeptide chain containing the substitutions K290Y, Y296W, E356K, and D399K (encoding one Fc polypeptide of variant W125) |
| SEQ ID NO: 41 | Amino acid sequence of the Fc polypeptide chain encoded by SEQ ID NO: 40 |

DETAILED DESCRIPTION

There is a need in the art for therapeutic polypeptides that bind to a target molecule and that have improved activity as therapeutics due to enhanced effector functions associated with Fc-containing proteins, such as ADCC, CDC, and/or ADCP. Such proteins can be particularly useful in treating cancer, autoimmune and infectious diseases, and/or any condition in which the selective killing of cells expressing a particular target molecule is beneficial. ADCC depends on the interaction of Fcγ receptors (FcγRs), especially FcγRIIIA in humans, with the Fc region of an antibody or Fc-containing protein. As shown in FIG. 1, the interaction of human FcγRIIIA with a human Fc region is asymmetric, that is, FcγRIIIA comes into contact with different amino acid residues on the two Fc polypeptide chains that make up the Fc region. See also Sondermann et al. (2000), Nature 406: 267-273. The binding sites of the FcγRs on an IgG Fc region have been mapped in some detail. Shields et al. (2001), J. Biol. Chem. 276(9): 6591-6604. Specifically, portions of FcγRIIIA are within 5.0 Å of amino acid residues L235, S239, D265, L328, P329, A330, and I332 on one Fc polypeptide chain and amino acid residues L235, P238, S239, D265, S267, D270, Y296, N297, S298, T299, and A327 on the other as determined by X-ray crystallography. Thus, asymmetric alterations in the Fc region may be needed to maximally enhance the interaction of FcγRIIIA with the Fc region of an Fc-containing protein and, thus, enhance ADCC. In another aspect, such heterodimeric Fc regions can also have different binding regions attached to each Fc polypeptide chain, thus creating a molecule that can have different binding specificities on each of its two binding arms. The instant invention provides Fc-containing proteins comprising such asymmetric substitutions in their Fc regions and having increased binding to FcγRIIIA and enhanced ADCC activity. In some cases, such polypeptides can also be bispecific, or multispecific, that is, they may bind to two or more different target molecules.

Definitions

All numbering of amino acid residues in an IgG constant region is done according to the EU numbering system as used Edelman et al. (1969), Proc. Natl. Acad. Sci. 63: 78-85. The portions of this reference describing and/or illustrating this numbering system are incorporated herein by reference. This system is a sequential numbering of the amino acids of a human IgG1 antibody. FIG. 2 shows the sequence of the Fc region of a human IgG1 antibody numbered according to the EU system. Particular amino acid residues in an IgG1 constant region of an antibody are notated using the one letter code for amino acids and the EU numbering system. For example, "D399" refers to an aspartic acid that is present in wild type IgG at position 399. Mutations at a particular residue are notated similarly. For example, "D399K" means that the aspartic acid that is present in a wild type IgG1 at position 399 has been changed to a lysine.

"ADCC" refers to a process called antibody-dependent cellular cytotoxicity, which is an immune response mediated primarily by natural killer (NK) cells in humans. In ADCC, FcγRIII on the surface of an NK cell recognizes the Fc region of antibody that is bound to antigen displayed on the surface of a target cell. This activates the NK cell, which releases perforins and granzymes, leading to lysis and apoptosis of the target cells.

"CDC" refers to a complex process called complement-dependent cytotoxicity that can lead to cell killing through the action of a cascade of proteins that can act through either of two major pathways. See, e.g., Liszewski and Atkinson, Ch. 26 in FUNDAMENTAL IMMUNOLOGY, 3$^{rd}$ ed., Paul, ed., Raven Press, New York, 1993, pp. 917-940, the portions of which describe CDC are incorporated herein by reference.

"ADCP" refers to a process called antibody dependent cell-mediated phagocytosis. In this Fc receptor-mediated process, target cells to which antibodies are bound are engulfed by phagocytic cells, such as macrophage, monocytes, neutrophils, and dendritic cells. Multiple Fc receptors are involved in this process. Richards et al., Mol. Cancer Ther. 7(8): 2517-2527 (2008) describe an in vitro assay for ADCP. The portion of Richards et al. describing this assay is incorporated herein by reference.

An "antibody," as meant herein, is a protein containing at least one heavy or light chain immunoglobulin variable region, in many cases a heavy and a light chain variable region. Thus, the term "antibody" encompasses single chain Fv antibodies (scFv, which contain heavy and light chain variable regions joined by a linker), Fab, F(ab)$_2$', Fab', scFv:Fc antibodies (as described in Carayannopoulos and Capra, Ch. 9 in FUNDAMENTAL IMMUNOLOGY, 3$^{rd}$ ed., Paul, ed., Raven Press, New York, 1993, pp. 284-286) or full length antibodies containing two full length heavy and two full length light chains, such as naturally-occurring IgG antibodies found in mammals. Id. Such IgG antibodies can be of the IgG1, IgG2, IgG3, or IgG4 isotype and can be human antibodies. The portions of Carayannopoulos and Capra that described the structure of antibodies are incorporated herein by reference. Further, the term "antibody" includes dimeric antibodies containing two heavy chains and no light chains such as the naturally-occurring antibodies found in camels and other dromedary species and sharks. See, e.g., Muldermans et al., 2001, J. Biotechnol. 74:277-302; Desmyter et al., 2001, J. Biol. Chem. 276:26285-90; Streltsov et al. (2005), Protein Science 14: 2901-2909. An antibody can be monospecific (that is, binding to only one kind of antigen) or multispecific (that is, binding to more than one kind of antigen). In some embodiments, an antibody can be bispecific (that is, binding to two different kinds of antigen). Further, an antibody can be monovalent, bivalent, or multivalent, meaning that it can bind to one or two or more antigen molecules at once. Some of the possible formats for such antibodies include monospecific or bispecific full length antibodies, monospecific monovalent antibodies (as described in International Application WO 2009/089004 and US Publication 2007/0105199, the relevant portions of which are incorporated herein by reference) that may inhibit or activate the molecule to which they bind, bivalent monospecific or bispecific dimeric Fv-Fc, scFv-Fc, or diabody Fc, monospecific monovalent scFv-Fc/Fc's, and the multispecific binding proteins and dual variable domain immunoglobulins described in US Publication 2009/0311253 (the relevant portions of which are incorporated herein by reference), among many other possible antibody formats.

An "Fc fusion protein," as meant herein, is a protein containing an Fc polypeptide chain fused to another polypeptide, which comprises a binding region that binds to a target molecule, and which does not comprise a heavy or light chain variable region of an antibody. The binding region of an Fc fusion protein can comprise a non-immunoglobulin polypeptide such as a soluble portion of a receptor or one or more peptides that bind to a target molecule (such as, for example, a "monomer domain" as defined in U.S. Pat. No. 7,820,790 that binds to a target protein, which can be selected as discussed in U.S. Pat. No. 7,820,790), or other polypeptides. The portions of U.S. Pat. No. 7,820,790 describing monomer domains and how they are selected are incorporated herein by reference. Other polypeptides that can be part of a binding region of an Fc fusion protein include polypeptides comprising scaffold domains that have been randomized in certain positions and subjected to selection for binding to a certain target molecule. Such scaffold domains include, for example, T-lymphocyte associated protein-4 (CTLA-4; Nuttall et al. (1999), Proteins 36: 217-227), the Z domain of Staphylococcal protein 1 (Nord et al. (1995), Protein Eng. 8: 601-608), green fluorescent protein, and the tenth type III domain of human fibronectin (FN3; Koide et al. (1998), J. Mol. Biol. 284: 1141-1151; Karatan et al. (2004), Chem. & Biol. 11: 835-844). The portions of these references describing the scaffold domains and their use to generate binding domains are incorporated herein by reference. Fc fusion proteins, like other proteins containing Fc polypeptide chains generally form multimers, which can be dimers. Since the Fc regions described herein are generally heterodimeric, such Fc fusion proteins can form heterodimers. In such a case, the polypeptide fused to the Fc polypeptide chain can be different in each of polypeptide chains that, together form the heterodimer. Thus, an Fc fusion protein can be heterodimeric and bispecific or monospecific or multispecific.

A "binding region," as meant herein, is a region of an Fc-containing protein as described herein that binds to a target molecule, such as, for example, a protein that is expressed at high levels on a cancer cell, on a cell mediating an autoimmune or inflammatory condition, on an infected cell, on an infectious agent, or on a cell mediating an immune effector function, for example, an NK cell. A binding region can contain a heavy or light chain immunoglobulin variable region or a non-immunoglobulin polypeptide.

An "scFv-Fc," as meant herein, is a polypeptide that consists of a heavy and a light chain variable region of an antibody joined by a linker, which is followed by an Fc polypeptide chain of an antibody, optionally the Fc region of a human IgG antibody, such as an IgG1, IgG2, IgG3, or IgG4 antibody.

A full length "heavy chain," as meant herein, comprises a heavy chain variable region ($V_H$), a first heavy chain constant domain ($C_H1$), a hinge domain, a second heavy chain constant domain ($C_H2$), and a third heavy chain constant domain ($C_H3$).

A full length "light chain," as meant herein, comprises a light chain variable region ($V_L$) and a light chain constant domain ($C_L$).

As meant herein, an "Fc region" is a dimer consisting of two polypeptide chains joined by one or more disulfide bonds, each chain comprising part or all of a hinge domain plus a $C_H2$ and a $C_H3$ domain. Each of the polypeptide chains is referred to as an "Fc polypeptide chain." To distinguish the two Fc polypeptide chains, one is referred to herein as an "A chain" and the other is referred to as a "B chain." More specifically, the Fc regions contemplated for use with the present invention are IgG Fc regions, which can be mammalian or human IgG1, IgG2, IgG3, or IgG4 Fc regions. Among human IgG1 Fc regions, at least two allelic types are known. One allelic type has the sequence as shown in FIG. 2 (SEQ ID NO:2). Another has two substitutions relative to the sequence in FIG. 2, namely E356D and M358L. In another naturally occurring human IgG1, the alanine at position 431 (corresponding to position 216 in SEQ ID NO:2) is a glycine. A human IgG1 Fc region as meant herein can contain any of these amino acid sequence variations.

An "Fc-containing protein," as meant herein, is a protein comprising an Fc region as described herein and a binding region that binds to a target molecule. The term "Fc-containing protein" encompasses an antibody or an Fc fusion protein that contains an Fc region.

"FcγRIIIA-158V" refers to the allelic variant of human FcγRIIIA that has a valine at position 158 in the amino acid sequence of FcγRIIIA as shown in SEQ ID NO:35. Similarly, "FcγRIIIA-158F" refers to the allelic variant of human FcγRIIIA that has a phenylalanine at position 158 in the amino acid sequence of FcγRIIIA. The sequence of human FcγRIIIA-158F, including the 17 amino acid signal peptide, is reported in NCBI Accession Number NP_001121065, which is incorporated herein by reference. Since this sequence includes the signal peptide, which is absent in the mature protein, position 158 is equivalent to amino acid 176. SEQ ID NO:35 contains the amino acid sequence of the mature form of FcγRIIIA-158V.

A "heterodimeric" Fc region, as meant herein is one in which the A chain and the B chain of the Fc region have different amino acid sequences rather than identical amino acid sequences.

An "scFv-Fc/Fc" is a dimeric protein consisting essentially of an scFv-Fc plus an Fc polypeptide chain (referred to herein as a "dummy Fc"). The scFv-Fc can be linked to the dummy Fc via one or more disulfide bridges. Further, the Fc region can contain "heterodimerizing alterations" in the $C_H3$ domains, such as one, two, three, or more pairs of charge pair substitutions, as described below.

The "$C_H3$-$C_H3$ interface" consists of those amino acids in the $C_H3$ region that come into close contact with residues of the other $C_H3$ region in the context of an Fc region and/or a full length antibody. More specifically these residues are within 4.5 Å of an amino acid residue on the other $C_H3$ region in the context of an Fc region. In an IgG1 antibody, these are the residues at the following positions (with EU residue number followed by position in SEQ ID NO:2 in parenthesis): 347 (132), 349 (134), 350 (135), 351 (136), 352 (137), 353 (138), 354 (139), 355 (140), 356 (141), 357 (142), 360 (145), 364 (149), 366 (151), 368 (153), 370 (155), 390 (175), 392 (177), 393 (178), 394 (179), 395 (180), 397 (182), 398 (183), 399 (184), 400 (185), 405 (190), 407 (192), 408 (193), 409 (194), and 439 (224).

"Chemotherapy," as used herein, means the treatment of a cancer patient with a "chemotherapeutic agent" that has cytotoxic or cytostatic effects on cancer cells. A "chemotherapeutic agent" specifically targets cells engaged in cell division and not cells that are not engaged in cell division. Chemotherapeutic agents directly interfere with processes that are intimately tied to cell division such as, for example, DNA replication, RNA synthesis, protein synthesis, the assembly, disassembly, or function of the mitotic spindle, and/or the synthesis or stability of molecules that play a role in these processes, such as nucleotides or amino acids. A chemotherapeutic agent therefore has cytotoxic or cytostatic effects on both cancer cells and other cells that are engaged in cell division. Chemotherapeutic agents are well-known in the art and include, for example: alkylating agents (e.g. busulfan, temozolomide, cyclophosphamide, lomustine (CCNU), methyllomustine, streptozotocin, cis-diamminedichloroplatinum, aziridinylbenzo-quinone, and thiotepa); inorganic ions (e.g. cisplatin and carboplatin); nitrogen mustards (e.g. melphalan hydrochloride, ifosfamide, chlorambucil, and mechlorethamine HCl); nitrosoureas (e.g. carmustine (BCNU)); anti-neoplastic antibiotics (e.g. adriamycin (doxorubicin), daunomycin, mitomycin C, daunorubicin, idarubicin, mithramycin, and bleomycin); plant derivatives (e.g. vincristine, vinblastine, vinorelbine, paclitaxel, docetaxel, vindesine, VP-16, and VM-26); antimetabolites (e.g. methotrexate with or without leucovorin, 5-fluorouracil with or without leucovorin, 5-fluorodeoxyuridine, 6-mercaptopurine, 6-thioguanine, cytarabine, 5-azacytidine, hydroxyurea, deoxycoformycin, gemcitabine, and fludarabine); podophyllotoxins (e.g. etoposide, irinotecan, and topotecan); as well as actinomycin D, dacarbazine (DTIC), mAMSA, procarbazine, hexamethylmelamine, pentamethylmelamine, L-asparaginase, and mitoxantrone, among many known in the art. See e.g. Cancer: Principles and Practice of Oncology, 4th Edition, DeVita et al., eds., J. B. Lippincott Co., Philadelphia, Pa. (1993), the relevant portions of which are incorporated herein by reference. Alkylating agents and nitrogen mustard act by alkylating DNA, which restricts uncoiling and replication of strands. Methotrexate, cytarabine, 6-mercaptopurine, 5-fluorouracil, and gemcitabine interfere with nucleotide synthesis. Plant derivatives such a paclitaxel and vinblastine are mitotic spindle poisons. The podophyllotoxins inhibit topoisomerases, thus interfering with DNA replication. Antibiotics doxorubicin, bleomycin, and mitomycin interfere with DNA synthesis by intercalating between the bases of DNA (inhibiting uncoiling), causing strand breakage, and alkylating DNA, respectively. Other mechanisms of action include carbamoylation of amino acids (lomustine, carmustine), and depletion of asparagine pools (asparaginase). Merck Manual of Diagnosis and Therapy, 17$^{th}$ Edition, Section 11, Hematology and Oncology, 144. Principles of Cancer Therapy, Table 144-2 (1999). Specifically included among chemotherapeutic agents are those that directly affect the same cellular processes that are directly affected by the chemotherapeutic agents listed above.

"Non-chemotherapeutic anti-neoplastic agents" are chemical agents, compounds, or molecules having cytotoxic or cytostatic effects on cancer cells other than chemotherapeutic agents. Non-chemotherapeutic antineoplastic agents may, however, be targeted to interact directly with molecules that indirectly affect cell division such as cell surface receptors, including receptors for hormones or growth factors. However, non-chemotherapeutic antineoplastic agents do not interfere directly with processes that are intimately linked to cell division such as, for example, DNA replication, RNA synthesis, protein synthesis, or mitotic spindle function, assembly, or disassembly. Examples of non-chemotherapeutic anti-neoplastic agents include inhibitors of Bcl2, inhibitors of farnesyltransferase, anti-estrogenic agents such as tamoxifen, anti-androgenic compounds, interferon, arsenic, retinoic acid, retinoic acid derivatives, antibodies targeted to tumor-specific antigens, and inhibitors of the Bcr-Abl tyrosine kinase (e.g. the small molecule STI-571 marketed under the trade name GLEEVEC™ by Novartis, N.Y. and New Jersey, USA and Basel, Switzerland), among many possible non-chemotherapeutic anti-neoplastic agents.

"Heterodimerizing alterations" generally refer to alterations in the A and B chains of an Fc region that facilitate the formation of heterodimeric Fc regions, that is, Fc regions in which the A chain and the B chain of the Fc region do not have identical amino acid sequences. Heterodimerizing alterations can be asymmetric, that is, a A chain having a certain alteration can pair with a B chain having a different alteration. These alterations facilitate heterodimerization and disfavor homodimerization. Whether hetero- or homodimers have formed can be assessed by size differences as determined by polyacrylamide gel electrophoresis in situations where one polypeptide chain is a dummy Fc and the other is an scFv-Fc. One example of such paired heterodimerizing alterations are the so-called "knobs and holes" substitutions. See, e.g., U.S. Pat. No. 7,695,936 and US Patent Application Publication 2003/0078385, the portions of which describe such mutations are incorporated herein by reference. As meant herein, an Fc region that contains one pair of knobs and holes substitutions, contains one substitution in the A chain and another in the B chain. For example, the following knobs and holes substitutions in the A and B chains of an IgG1 Fc region have been found to increase heterodimer formation as compared with that found with unmodified A and B chains: 1) Y407T in one chain and T366Y in the other; 2) Y407A in one chain and T366W in the other; 3) F405A in one chain and T394W in the other; 4) F405W in one chain and T394S in the other; 5) Y407T in one chain and T366Y in the other; 6) T366Y and F405A in one chain and T394W and Y407I in the other; 7) T366W and F405W in one chain and T394S and Y407A in the other; 8) F405W and Y407A in one chain and T366W and T394S in the other; and 9) T366W in one polypeptide of the Fc and T366S, L368A, and Y407V in the other. Alternatively or in addition to such alterations, substitutions creating new disulfide bridges can facilitate heterodimer formation. See, e.g., US Patent Application Publication 2003/0078385, the portions of which describe such mutations are incorporated herein by reference. Such alterations in an IgG1 Fc region include, for example, the following substitutions: Y349C in one Fc polypeptide chain and S354C in the other; Y349C in one Fc polypeptide chain and E356C in the other; Y349C in one Fc polypeptide chain and E357C in the other; L351C in one Fc polypeptide chain and S354C in the other; T394C in one Fc polypeptide chain and E397C in the other; or D399C in one Fc polypeptide chain and K392C in the other. Similarly, substitutions changing the charge of a one or more residue, for example, in the $C_H3$-$C_H3$ interface, can enhance heterodimer formation as explained in WO 2009/089004, the portions of which describe such substitutions are incorporated herein by reference. Such substitutions are referred to herein as "charge pair substitutions," and an Fc region containing one pair of charge pair substitutions contains one substitution in the A chain and a different substitution in the B chain. General examples of charge pair substitutions include the following: 1) K409D or K409E in one chain plus D399K or D399R in the other; 2) K392D or K392E in one chain plus D399K or D399R in the other; 3) K439D or K439E in one chain plus E356K or E356R in the other; and 4) K370D or K370E in one chain plus E357K or E357R in the other. In addition, the substitutions R355D, R355E, K360D, or K360R in both chains can stabilize heterodimers when used with other heterodimerizing alterations. Specific charge pair substitutions can be used either alone or with other charge pair substitutions. Specific examples of single pairs of charge pair substitutions and combinations thereof include the following: 1) K409E in one chain plus D399K in the other; 2) K409E in one chain plus D399R in the other; 3) K409D in one chain plus D399K in the other; 4) K409D in one chain plus D399R in the other; 5) K392E in one chain plus D399R in the other; 6) K392E in one chain plus D399K in the other; 7) K392D in one chain plus D399R in the other; 8) K392D in one chain plus D399K in the other; 9) K409D and K360D in one chain plus D399K and E356K in the other; 10) K409D and K370D in one chain plus D399K and E357K in the other; 11) K409D and K392D in one chain plus D399K, E356K, and E357K in the other; 12) K409D and K392D on one chain and D399K on the other; 13) K409D and K392D on one chain plus D399K and E356K on the other; 14) K409D and K392D on one chain plus D399K and D357K on the other; 15) K409D and K370D on one chain plus D399K and D357K on the other; 16) D399K on one chain plus K409D and K360D on the other; and 17) K409D and K439D on one chain plus D399K and E356K on the other. Any of the these heterodimerizing alterations can be used in polypeptides comprising the variant F regions described herein, which bind to FcγRIIIA with a lower $K_D$ than does a similar polypeptide with an unaltered Fc region.

A "target molecule," as meant herein, is a molecule to which the binding region of an Fc-containing protein described herein binds. In some embodiments, a target molecule is a protein that is expressed at high levels, for example, on a cancer cell, on a cell mediating an autoimmune or inflammatory condition, on an infected cell, on an infectious agent, or on a cell mediating an immune effector function, for example, an NK cell.

"Tumor burden" refers to the number of viable cancer cells, the number of tumor sites, and/or the size of the tumor(s) in a patient suffering from a cancer. A reduction in tumor burden can be observed, for example, as a reduction in the amount of a tumor-associated antigen or protein in a patient's blood or urine, a reduction in the number of tumor cells or tumor sites, and/or a reduction in the size of one or more tumors.

A "therapeutically effective amount" of a protein comprising a variant Fc region as described herein is an amount that has the effect of, for example, reducing or eliminating the tumor burden of a cancer patient or reducing or eliminating the symptoms of any disease condition that the protein is used to treat. A therapeutically effective amount need not completely eliminate all symptoms of the condition, but may reduce severity of one or more symptoms or delay the onset of more serious symptoms or a more serious disease that can occur with some frequency following the treated condition.

"Treatment" of any disease mentioned herein encompasses an alleviation of at least one symptom of the disease, a reduction in the severity of the disease, or the delay or prevention of disease progression to more serious symptoms that may, in some cases, accompany the disease or lead to at least one other disease. Treatment need not mean that the disease is totally cured. A useful therapeutic agent needs only to reduce the severity of a disease, reduce the severity of one or more symptoms associated with the disease or its treatment, or delay the onset of more serious symptoms or a more serious disease that can occur with some frequency following the treated condition.

Proteins Containing Variant Fc Regions

The present invention encompasses Fc-containing proteins that comprise a binding region that binds to a target molecule and a variant Fc region. These include antibodies and Fc fusion proteins, containing human or non-human IgG Fc regions, which could be IgG1, IgG2, IgG3, or IgG4 Fc regions, that are altered at selected amino acid residues as compared to an unchanged human or non-human Fc region and that bind to FcγRIIIA with enhanced affinity as compared to the unchanged human or non-human Fc region. Since FcγRIIIA interacts with an Fc region in an asymmetric fashion, i.e., contacting different amino acid residues in the two Fc polypeptide chains that make up the Fc region, the asymmetrically altered Fc regions described herein can be particularly effective in enhancing affinity to FcγRIIIA and, thus, ADCC. The altered human Fc regions described herein can be altered such that the sequences of the two Fc polypeptide chains that make up an Fc region, that is, the A chain and the B chain, differ. To facilitate the formation of such asymmetrically altered Fc regions, these Fc regions can also contain heterodimerizing alterations, which are different in the A and B chains, that discourage the formation of homodimeric Fc-containing proteins and encourage the formation of heterodimeric Fc-containing proteins. Proteins containing the altered Fc regions can be more effective at binding to FcγRIIIA and at eliciting.

ADCC as compared to proteins comprising an unaltered Fc region, or to an Fc region containing only heterodimerizing alterations, and can have increased efficacy as therapeutics in vivo, for example in oncologic or neoplastic indications and/or in treating autoimmune or infectious conditions. Included among the antibodies and Fc fusion proteins described herein are heterodimers in which each Fc polypeptide chain is fused to a different protein. Such Fc fusion proteins are bivalent and bispecific. Also included are bivalent and monospecific Fc fusion protein. Similarly, monospecific or bispecific full length antibodies, monovalent antibodies, and bispecific or monospecific scFv-Fc's are among the many kinds of proteins that could contain the altered Fc regions described herein. The invention also encompasses nucleic acids encoding the Fc polypeptide chains in the altered Fc regions and proteins containing these Fc polypeptide chains. Also provided are methods of making these proteins and methods of using these proteins to treat various human conditions.

There are three different classes of human Fc gamma receptors (FcγRs) for IgG antibodies, FcγRI, FcγRII, and FcγRIII. Aloes et al. (2009), Expert Rev. Clin. Immunol. 5(6): 735-747. Seven subclasses have been characterized, that is, FcγRIA, FcγRIB, FcγRIIA, FcγRIIB, FcγRIIC, FcγRIIIA, and FcγRIIIB. Id. These subclasses can be further divided into isoforms resulting from alternative splicing, and several allelic variants having differing capacities to bind various IgG subclasses and trigger effector functions have also been found. Id. Most of these receptors activate cells following their engagement by IgG antibodies, especially IgG1 or IgG3 antibodies, leading to cytotoxicity, cytokine release, and phagocytosis/endocytosis followed by antigen presentation. Activation is mediated through an immunoreceptor tyrosine-based activation motif (ITAM) present either in the intracellular domain of the FcγR or in the intracellular part of an accessory signaling protein. Id. FcγRIIB receptors are the only known human inhibitory FcγR and contain an immunoreceptor tyrosine-based inhibitory motif (ITIM) in the intracellular domain that mediates inhibition of cell activation. Id.

Enhanced affinity of an antibody for FcγRIIIA can be indicative of enhanced clinical efficacy in oncologic indications. Allelic variants of FcγRIIIA having either a valine or a phenylalanine at amino acid 158 have been associated with higher or lower affinity binding to IgG, respectively. Koene et al. (1997), Blood 90(3): 1109-1114. These allelic differences also significantly correlate with clinical efficacy observed in patients with follicular lymphoma treated with rituximab (an IgG1 anti-CD20 monoclonal antibody) and in patients with solid tumors treated with either cetuximab (a chimeric IgG1 anti-epidermal growth factor receptor monoclonal antibody) or trastuzumab (an IgG1 anti-epidermal growth factor receptor 2 monoclonal antibody). Abes et al. (2009), Expert Rev. Clin. Immunol. 5(6): 735-747. Provided herein are Fc-containing proteins that have enhanced affinity for both alleles of FcγRIIIA and therefore could also have enhanced efficacy as therapeutics in oncologic indications.

Each of the Fc polypeptide chains, that is, the A chain and the B chain which together make up an altered Fc region of the invention, can have amino acid sequences that differ because of amino acid substitutions relative to the sequence of a human IgG Fc polypeptide chain. An Fc polypeptide chain can be of a human IgG1 or IgG3 Fc polypeptide. In some embodiments, each Fc polypeptide chain comprises from one to twenty, one to ten, or one to five amino acid substitutions relative to a naturally-occurring human Fc sequence. In other embodiments, an Fc polypeptide chain can comprise zero, one, two, three, four, five, six, seven, eight, nine, or ten amino acid substitutions relative to a naturally-occurring human Fc polypeptide chain. In some embodiments, an Fc polypeptide chain can comprise no more than 2, 3, 4, 5, 6, 7, 8, 9, 10, 11, 12, 13, 14, or 15 amino acid substitutions. The substitutions can occur, for example, at one or more of the following sites in an Fc polypeptide chain: E233, L234, L235, S239, F241, F243, K246, K248, D249, L251, M252, I253, S254, R255, T256, E258, T260, V264, D265, S267, H268, E269, D270, E272, K274, F275, N276, Y278, V279, D280, V282, E283, V284, H285, N286, A287, K288, T289, K290, R292, E293, E294, Q295, Y296, S298, Y300, R301, V302, V303, V305, T307, L309, H310, Q311, D312, W313, L314, N315, K317, E318, K320, K322, S324, K326, A327, L328, A330, I332, E333, K334, T335, I336, S337, K338, A339, K340, R355, E356, D356, E357, K360, K362, K370, K392, D399, K409, D413, and/or K439. Different or the same individual substitutions listed above or combinations of these substitutions can be used in an A chain and a B chain of an Fc region. A variant Fc region can comprise alterations at sites in addition to those listed above.

In particular, the antibodies or Fc fusion proteins described herein, which comprise an Fc region, can contain one or more of the following particular amino acid substitutions in one or both of the A chain and the B chain that make up the Fc region: E233L, L234I, L234Y, L235S, G236Y, S239D, S239E, S239N, S239I, F243M, F243L, F243V, F243I, K246W, K246E, K246S, K246V, K248Y, K248L, M252D, I253V, I253K, R255S, R255N, T256V, T256Q, E258S, E258V, H268E, H268K, A287F, K288T, K288I, K290G, K290F, K290S, K290W, K290Q, K290Y, E294L, Y296W, Y296L, S298A, S298C, S298T, V302Q, T307P, T307S, T307E, T307G, L309C, L309S, L309K, L309E, Q311M, N315A, N315S, A330H, A330F, A330M, I332E, K334L, K334V, K334A, K334M, A339T, K340N, R355D, R355E, E356K, E356R, D356K, D356R, E357K, E357R, K360D, K360E, K370D, K370E, K392D, K392E, D399K, D399R, K409D, K409E, D413N, K439D, and K439E. In addition, any of the above proteins can comprise additional alterations such as heterodimerizing alterations. For example, they can comprise K392D and K409D in one Fc polypeptide chain and E356K and D399K in the other.

More particularly, the proteins of the invention can comprise an Fc region in which the A and B chains comprise the following substitutions: (1) K334V in one Fc polypeptide chain and Y296W plus S298C in the other; (2) K334V in one Fc polypeptide chain and L234Y, Y296W, and S298C in the other; (3) L235S, S239D, and K334V in one Fc polypeptide chain and L234Y, K290Y, and Y296W in the other; (4) L235S, S239D, and K334V in one Fc polypeptide chain and L234Y, Y296W, and S298C in the other; (5) Q311M and K334V in one Fc polypeptide chain and L234Y, F243V, and Y296W in the other; (6) Q311M and K334V in one Fc polypeptide chain and L234Y, E294L, and Y296W in the other, as in, for example, SEQ ID NO:8 and SEQ ID NO:10, respectively; (7) Q311M and K334V in one Fc polypeptide chain and L234Y, Y296W, and S298C in the other; (8) S239D and K334V in one Fc polypeptide chain and L234Y, K290Y, and Y296W in the other; (9) S239D and K334V in one Fc polypeptide chain and L234Y, Y296W, and S298C in the other; (10) F243V and K334V in one Fc polypeptide chain and L234Y, K290Y, and Y296W in the other; (11) F243V and K334V in one Fc polypeptide chain and L234Y, Y296W, and S298C in the other; (12) E294L and K334V in one Fc polypeptide chain and L234Y, K290Y, and Y296W in the other; (13) E294L and K334V in one Fc polypeptide chain and L234Y, Y296W, and S298C in the other; (14) K334V in one Fc polypeptide chain and L234Y and Y296W in the other; (15) K334V in one Fc polypeptide chain and L234Y and S298C in the other; (16) K334V in one Fc polypeptide chain and E294L and Y296W in the other; (17) K334V and S298C in one Fc polypeptide chain and L234Y and Y296W in the other; (18) K334V and S298I in one Fc polypeptide chain and L234Y and Y296W in the other; (19) K334V and S298T in one Fc polypeptide chain and L234Y and Y296W in the other; (20) K334V and S298V in one Fc polypeptide chain and L234Y and Y296W in the other; (21) K334V and S298C in one Fc polypeptide chain and L234Y, Y296W, and K290Y in the other; (22) K334V and S298I in one Fc polypeptide chain and L234Y, Y296W, and K290Y in the other; (23) K334V and S298T in one Fc polypeptide chain and L234Y, Y296W, and K290Y in the other; (24) K334V and S298V in one Fc polypeptide chain and L234Y, Y296W, and K290Y in the other; (25) S298T and K334V in one Fc polypeptide chain and L234Y, K290Y, and Y296W in the other, as in, for example, SEQ ID NO:16 and SEQ ID NO:18, respectively; (26) A330M and K334V in one Fc polypeptide chain and L234Y, K290Y, and Y296W in the other; (27) A330F and K334V in one Fc polypeptide chain and L234Y, K290Y, and Y296W in the other; (28) Q311M and A330M and K334V in one Fc polypeptide chain and L234Y, E294L, and Y296W in the other; (29) Q311M and A330F and K334V in one Fc polypeptide chain and L234Y, E294L, and Y296W in the other; (30) S298T and A330M and K334V in one Fc polypeptide chain and L234Y, K290Y, and Y296W in the other; (31) S298T and A330F and K334V in one Fc polypeptide chain and L234Y, K290Y, and Y296W in the other; (32) S239D and A330M and K334V in one Fc polypeptide chain and L234Y, K290Y, and Y296W in the other; (33) S239D and S298T and K334V in one Fc polypeptide chain and L234Y, K290Y, and Y296W in the other; (34) A330M and K334V in one Fc polypeptide chain and K290Y, and Y296W in the other; (35) A330M and K334V in one Fc polypeptide chain and E294L and Y296W in the other; (36) A330M and K334V in one Fc polypeptide chain and L234Y and Y296W in the other; (37) E233L and Q311M and K334V in one Fc polypeptide chain and L234Y, E294L, and Y296W in the other; (38) L234I and Q311M and K334V in one Fc polypeptide chain and L234Y, E294L, and Y296W in the other; (39) E233L and A330M and K334V in one Fc polypeptide chain and L234Y, K290Y, and Y296W in the other; (40) L234I and Q311M and K334V in one Fc polypeptide chain and L234Y, K290Y, and Y296W in the other; (41) A330M and K334V in one Fc polypeptide chain and L234Y and Y296W in the other; or (42) A330M and K334V in one Fc polypeptide chain and K290Y and Y296W in the other. Any of the above proteins can also comprise heterodimerizing alteration as described above. In some embodiments, they can further comprise K392D and K409D in one Fc polypeptide chain and E356K and D399K in the other.

Examples of amino acid sequences of Fc polypeptide chains, as described herein, include SEQ ID NOs:8, 10, 12, 14, 16, 18, 20, 22, 24, 26, 28, 30, 32, 34, 37, 39, and 41. These sequences contain heterodimerizing alterations and substitutions that enhance binding to FcγRIIIA.

The Fc-containing proteins of the invention can contain heterodimeric human IgG1 Fc regions. That is, the two Fc polypeptide chains that, together, make up the Fc region each have a different amino acid sequence. In some embodiments a heterodimeric Fc region of the invention contains heterodimerizing alterations (as defined above), thus greatly facilitating production of proteins containing the heterodimeric Fc.

An IgG Fc region is generally glycosylated at N297 when it is produced by a mammalian cell, and the absence of fucose in this carbohydrate can increase binding to FcγRIII and the ability of an IgG antibody to elicit ADCC. Malphettes et al. (2010), Biotechnol. Bioeng. 106(5): 774-783. A number of approaches for producing defucosylated antibodies have been explored including the use of CHO cell line Lec13 to produce antibodies, use of a cell line for antibody production in which the alfa-1,6-fucosyltransferase (FUT8) gene or the GDP-fucose transporter (GFT) gene has been disrupted, use of a cell line for antibody production that contains a small interfering RNA against the FUT8 gene or the GDP-mannose 4,6-dehydratase gene, or coexpression in an antibody-producing cell line of β-1,4-N-acetylglucoaminyltransferase III (GnT-III) and Golgi α-mannosidase II (ManII). Ishiguro et al. (2010), Cancer Sci 101: 2227-2233. The Fc-containing proteins, including antibodies and Fc fusion proteins, described herein can be "defucosylated," that is, essentially free of fucose or containing only minor amounts of fucose. As meant herein, at least about 85%, 90%, or 95% of the glycans released from a defucosylated protein preparation do not contain fucose. The terms "defucosylated" and "afucosylated" are used interchangeably herein. Such proteins can be produced as described above, for example, in FUT8$^{-/-}$ or GFT$^{-/-}$ CHO cells. The fucose contents of a protein can be determined by as described by Ishiguro et al. (2010), Cancer Sci 101: 2227-2233, at 2228-2229, the relevant portion of which is incorporated herein by reference.

Many proteins are known to be expressed at high levels on cancer cells, on cells that mediate an autoimmune or inflammatory condition, or on infectious agents or infected cells. Such proteins are potential target molecules for therapeutic Fc-containing proteins described herein. Antibodies or Fc fusion proteins that bind to such potential target proteins are particularly appropriate for use with the present invention. Potential target proteins known to be expressed on human cancer cells include the following human proteins: WT1, MUC1, LMP2, EGFRvIII, HER-2/neu, MAGE-A3, NY-ESO-1, PSMA, GM2/GD2 synthase, CEA, MLANA/MART1, gp100, survivin, prostate-specific antigen (PSA), telomerase reverse transcriptase (hTERT), sarcoma translocation breakpoints, EPHA2, prostatic acid phosphatase (PAP), melanoma inhibitor of apoptosis (ML-IAP), α-fetoprotein (AFP), epithelial cell adhesion molecule (EpCAM), ERG, NA17.A2 peptide (VLPDVFIRC), paired box 3 (PAX3), anaplastic lymphoma kinase (ALK), androgen receptor, cyclin β1, polysialic acid, rho-related GTP-binding protein RhoC, v-myc myelocytomatosis viral related oncogene (MYCN), TRP-2, GD3 ganglioside, fucosyl GM1, mesothelin, prostate stem cell antigen (PSCA), MAGE-A1, CYP1B1, PLAC1, GM3, BORIS, tetranectin (TN), ETV6-AML1 (especially peptides including the breakpoint), NY-BR-1, RGS5, SART3, STn, carbonic anhydrase IX, PAX5, proacrosin binding protein sp32 precursor (OY-TES-1), sperm protein 17 (Sp17), LCK, high molecular weight melanoma-associated antigen (HMWMAA, also known as melanoma chondroitin sulfate proteoglycan), AKAP-4, SSX2, XAGE-1, B7H3 (also known as CD276), legumain, TIE2, prostate-associated gene 4 protein (PAGE-4), vascular endothelial growth factor receptor 2 (VEGFR2), protamine 2 (also known as MAD-CT-1), glomulin (also known as FAP), PDGFR-β, SSX2, SSX5, Fos-related antigen 1, CD20, integrin αvβ3, 5T4 oncofetal antigen, CA IX, CD5, CD19, CD22 (also known as Siglec-2), CD30 (also known as TNFRSF1), CD33 (also known as Siglec-3), CD40, CD44V6, CD55, CD56 (also known as NCAM), CTLA-4 (also known as CD152), EGFR, GD2, HER2, HLA-DR10 (MHC II), IGF1R, IL-6, sialyl Lewis Y, TAG-72, TALE, TRAILR2, VEGF, CD52 (also known as CAMPATH-1), CD4, CD73, CA125 (also known as MUC16), CD66e, CD80 (also known as B7-1), PDGFRβ, prostate specific membrane antigen (PSMA, also known as glutamate carboxypeptidase 2, among many other names). Cancer antigens also include the human herpes virus 4 protein LMP2, the human papillomavirus proteins E6 and E7, and the glycoceramide globo H (as described in Gilewski et al. (2001), Proc. Natl. Acad. Sci. 98(6): 3270-3275, the portions of which describe globo H are incorporated herein by reference), the α4 subunit of the α4β1 and α4β7 integrins, the α4β7 integrin, BAFF, APRIL, CD2, CD3, CD20, CD52, CD73, CD80, CD86, the $C_5$ complement protein, IgE, IL-1β, IL-5, IL-6R, IL-12, IL-23, and tumor necrosis factor α (TNF α).

Other targets include proteins or other molecules displayed on the surface of pathogenic organisms including viruses, bacteria (including the species *Borrelia, Staphylococcus, Escherichia*, among many other species), fungi (including yeast), giardia, amoeba, eukaryotic protists of the genus *Plasmodium*, ciliates, trypanosomes, nematodes, and other eukaryotic parasites.

In embodiments where the Fc-containing protein is monospecific or bispecific or multispecific, the Fc-containing protein can bind one or two or multiple target molecules, which can be identical or different target molecules and can be monomers or multimers, on the same cells or different types of cells, to antagonize or agonize the signaling pathway; or to increase the avidity or specificity of an interaction between a target molecule and another molecule (which may or may not be a target molecule). In another aspect, a bispecific or multispecific Fc-containing protein can bind to a target molecule, such as those mentioned in the paragraphs above, and another molecule, which can also be a target molecule, expressed at high levels on a cell involved in mediating a cytotoxic response by the immune system, such as, for example, NKG2D on NK cells or CD3 or T cell receptor on T cells. As explained above, the target molecule could be, for example, one of the following: (1) a human protein that is selectively expressed on cancer cells; (2) a protein of a virus or other pathogen that is highly expressed on the surface of the pathogen or on the surface of a pathogen-infected host cell; or (3) a human protein that is selectively expressed on the surface of a human cell type that mediates a condition such as an autoimmune or inflammatory disease.

Nucleic Acids Encoding Proteins Containing Altered Fc Regions

Nucleic acids encoding the Fc polypeptide chains of the Fc-containing proteins described herein are also provided. In one aspect, nucleic acids are provided that encode Fc polypeptides, and/or Fc-containing proteins comprising them, comprising one or more of the following amino acid sequences: SEQ ID NOs:8, 10, 12, 14, 16, 18, 20, 22, 24, 26, 28, 30, 32, 34, 37, 39, or 41. Examples of sequences encoding such Fc polypeptide chains include SEQ ID NOs: 7, 9, 11, 13, 15, 17, 19, 21, 23, 25, 27, 29, 31, 33, 36, 38, and 40. These nucleic acids encode the amino acid sequences of SEQ ID NOs:8, 10, 12, 14, 16, 18, 20, 22, 24, 26, 28, 30, 32, 34, 37, 39, and 41, respectively. Many additional nucleic acid sequences, encoding the many variant Fc polypeptide chains described herein, are also encompassed by the instant invention. These nucleic acids are useful for, inter alia, producing recombinant proteins containing altered Fc polypeptide chains, as described herein. These altered Fc polypeptide chains can be part of a heterodimeric Fc region that binds to FcγRIIIA with enhanced affinity, as shown by binding with a lower $K_D$ than a wild type Fc region. Such nucleic acids can also encode a signal sequence that facilitates the secretion of a protein in mammalian cells and/or a binding region that binds to a target molecule. It is understood in the art that signal sequences are cleaved from the remainder of a protein during maturation and are not part of a mature protein, even though they are encoded in a nucleic acid encoding the protein. Signal sequences can be easily identified, e.g., as described by Kertein et al. (2000), Bioinformatics 16(8): 741-742, Nielsen and Krogh (1998), Proc. Sixth Int. Conf. on Intelligent Systems for Molecular Biol (AAAI Press): 122-130, Nielsen et al. (1997), Protein Eng. 10(1): 1-6, and Nielsen et al. (1997), Int. J. Neural Systems 8(5&6): 581-599. The relevant portions of the references are incorporated herein by reference. The nucleic acids of the invention include DNA and RNA in single- and double-stranded forms. In some embodiments, both polypeptide chains of a heterodimeric Fc-containing protein are encoded on a single nucleic acid molecule. In other embodiments, a heterodimeric Fc-containing protein can be encoded on two, three, or more nucleic acid molecules.

An "isolated nucleic acid," as meant herein, is a nucleic acid that has been separated from adjacent sequences present in the genome of the organism from which the nucleic acid was initially isolated. For example, if the nucleic acid encodes an altered human IgG1 Fc region, the adjacent sequences would be the sequences adjacent to the sequences encoding an IgG1 Fc in the human genome. It is to be understood that nucleic acids synthesized chemically or produced enzymatically by PCR are "isolated nucleic acids," as meant herein. An isolated nucleic acid molecule refers to a nucleic acid molecule in the form of a separate fragment or as a component of a larger nucleic acid construct.

Methods of Making Fc-Containing Proteins with Variant Fc Regions

Fc-containing proteins, such as antibodies and fusion proteins, encompassed by the invention can be made by methods known in the art. More specifically, a nucleic acid that encodes an Fc-containing protein including an altered Fc polypeptide chain, as described herein, can be introduced into a vector, which can be introduced into a host cell. Since the heterodimeric, Fc-containing proteins described herein necessarily contain at least two polypeptide chains, nucleic acids encoding these chains may be present on either a single vector or two or more vectors. If more than one vector is used, these vectors can be introduced together into a host cell. Vectors and host cells comprising nucleic acids encoding such a protein are encompassed by the invention. The host cell containing the nucleic acids encoding the Fc-containing protein can be cultured under conditions such that the protein can be expressed. The expressed protein can then be obtained from the medium in which the cells are cultured or from the cells themselves and purified by any of the many appropriate means known in the art. In addition, genetic engineering methods for the production of proteins include the expression of the polynucleotide molecules in cell free expression systems, in cellular hosts, in tissues, and in animal models, according to known methods.

The vector can include a selectable marker and an origin of replication, for propagation in a host. The vector can further include suitable transcriptional or translational regulatory sequences, such as those derived from mammalian, avian, microbial, viral, plant, or insect genes, operably linked to the nucleic acid encoding the protein. Examples of such regulatory sequences include transcriptional promoters, operators, or enhancers, mRNA ribosomal binding sites, and appropriate sequences that control transcription and translation. Nucleotide sequences are operably linked when the regulatory sequence functionally relates to the DNA encoding the target protein. Thus, a promoter nucleotide sequence is operably linked to a nucleic acid sequence if the promoter nucleotide sequence directs the transcription of the nucleic acid sequence.

Suitable host cells for expression of the antibodies or Fc fusion proteins described herein include prokaryotic cells, yeast cells, plant cells, insect cells, and higher eukaryotic cells, including mammalian or avian cells. The regulatory sequences in the vector will be chosen such that they are operable in the host cell. Suitable prokaryotic host cells include bacteria of the genera *Escherichia*, *Bacillus*, and *Salmonella*, as well as members of the genera *Pseudomonas*, *Streptomyces*, and *Staphylococcus*. For expression in prokaryotic cells, for example, in *E. coli*, the polynucleotide molecule encoding the protein preferably includes an N-terminal methionine residue to facilitate expression of the recombinant polypeptide. The N-terminal methionine may optionally be cleaved from the expressed polypeptide. Suitable yeast host cells include cells from genera including *Saccharomyces*, *Pichia*, and *Kluveromyces*. Preferred yeast hosts are *S. cerevisiae* and *P. pastoris*. A suitable system for expression in an insect host cell is described, for example, in the review by Luckow and Summers ((1988), BioTechnology 6: 47), the relevant portions of which are incorporated herein by reference. Suitable mammalian host cells include the COS-7 line of monkey kidney cells (Gluzman et al. (1981), Cell 23: 175-182), baby hamster kidney (BHK) cells, Chinese hamster ovary (CHO) cells (Puck et al. (1958), PNAS USA 60: 1275-1281), CV-1 (Fischer et al. (1970), Int. J. Cancer 5: 21-27), HEK 293 cells from human embryonic kidney (American Type Culture Collection (ATCC®) catalog no. CRL-1573), and human cervical carcinoma cells (HELA) (ATCC® CCL 2). The relevant portions of the references referred to in this paragraph are incorporated herein by reference. Many other host cells are known in the art.

Expression vectors for use in cellular hosts generally comprise one or more phenotypic selectable marker genes. Such genes encode, for example, a protein that confers antibiotic resistance or that supplies an auxotrophic requirement. A wide variety of such vectors are readily available from commercial sources. Examples include pGEM® vectors (Promega), pSPORT vectors, and pPROEX™ vectors (InVitrogen, Life Technologies, Carlsbad, Calif.), Bluescript vectors (Stratagene), and pQE vectors (Qiagen). Yeast vectors will often contain an origin of replication sequence from a 2μ yeast plasmid, an autonomously replicating sequence (ARS), a promoter region, sequences for polyadenylation, sequences for transcription termination, and a selectable marker gene. Vectors replicable in both yeast and *E. coli* (termed shuttle vectors) may also be used. In addition to the above-mentioned features of yeast vectors, a shuttle vector will also include sequences for replication and selection in *E. coli*. Direct secretion of the target polypeptides expressed in yeast hosts may be accomplished by the inclusion of nucleotide sequence encoding the yeast α-factor leader sequence at the 5' end of the Fc-containing protein. Brake (1989), Biotechnology 13: 269-280.

Examples of suitable expression vectors for use in mammalian host cells include pcDNA3.1/Hygro$^+$ (Invitrogen), pDC409 (McMahan et al. (1991), EMBO J. 10: 2821-2832), and pSVL (Pharmacia Biotech). Expression vectors for use in mammalian host cells can include transcriptional and translational control sequences derived from viral genomes. Commonly used promoter sequences and enhancer sequences that can be used to promote transcription of RNA encoding the proteins described herein include, but are not limited to, those derived from human cytomegalovirus (CMV), Adenovirus 2, Polyoma virus, and Simian virus 40 (SV40). Methods for the construction of mammalian expression vectors are disclosed, for example, in Okayama and Berg ((1982) Mol. Cell. Biol. 2:161-170), Cosman et al. ((1986) Mol. Immunol. 23:935-941), Cosman et al. ((1984) Nature 312: 768-771), EP-A-0 367 566, and WO 91/18982. The relevant portions of these references are incorporated herein by reference.

Uses for Fc-containing Proteins with Enhanced FcγRIIIA Binding

Fc-containing proteins of the invention, such as antibodies and Fc fusion proteins, can be used as therapeutics, particularly in disease contexts in which the selective killing of cells on which a particular target molecule is displayed is desirable. However, the Fc-containing proteins of the invention can also be useful for eliminating soluble ligands, viruses, or foreign pathogenic cells. For example, in cancer patients, it is desirable to kill cancer cells, which may selectively express certain proteins that can be targeted by the Fc-containing proteins described herein. Hence, antibodies or Fc fusion proteins that bind to such cancer target proteins and have enhanced cell killing properties can be desirable therapeutics in cancer indications. Further, it can also be useful to bring cancer cells and cytotoxic cells into close proximity to each other using bispecific Fc-containing proteins as described herein that bind to a cancer target protein, that is, a protein expressed on a cancer cell, and a protein expressed on a cytotoxic cell. For example, CD16, which is expressed on NK cells, or NKG2D, which is expressed on cytotoxic T cells and NK cells, are proteins expressed on cytotoxic cells that can be target proteins. In asthma, an inflammatory condition, it can be useful to kill eosinophils, which mediate damage of cells in the airway and induce hyperresponsiveness and mucus hypersecretion. Kolbeck et al. (2010), J. Allergy Clin. Immunol. 125: 1344-1353. Thus, Fc-containing proteins with enhanced cell killing properties against antigens preferentially expressed on eosinophils can be useful in asthma. Similarly, viruses, foreign pathogenic cells, or infected host cells can also be targeted by the antibodies or Fc fusion proteins described herein.

The invention contemplates methods for treating patients suffering from a cell proliferative disease, including various forms of cancer, with the Fc-containing proteins described herein or with combinations including Fc-containing proteins comprising an altered Fc region plus other therapeutic agents. The patient can be a human, but the methods may be applied to any mammal, including domestic animals such as pets and farm animals. Also provided are compositions for use in such methods that include a therapeutically effective amount of a protein containing an altered Fc region and, in some cases, an effective amount of another therapeutic agent, plus a suitable diluent, excipient, or carrier.

The Fc-containing proteins described herein can be administered with a variety of drugs and treatments have been widely employed in cancer treatment such as, for example, chemotherapeutic agents, non-chemotherpeutic, anti-neoplastic agents, and/or radiation. For example, chemotherapy and/or radiation can occur before, during, and/or after any of the treatments described herein. Examples of chemotherapeutic agents include, but are not limited to, cisplatin, taxol, etoposide, mitoxantrone (Novantrone), actinomycin D, cycloheximide, camptothecin (or water soluble derivatives thereof), methotrexate, mitomycin (e.g., mitomycin C), dacarbazine (DTIC), anti-neoplastic antibiotics such as adriamycin (doxorubicin) and daunomycin, and all the chemotherapeutic agents mentioned above.

Among the texts providing guidance for cancer therapy is Cancer, *Principles and Practice of Oncology*, 4th Edition, DeVita et al., Eds. J. B. Lippincott Co., Philadelphia, Pa. (1993). An appropriate therapeutic approach is chosen according to the particular type of cancer, and other factors such as the general condition of the patient, as is recognized in the pertinent field. The treatments described herein using the antibodies or Fc fusion proteins described herein may be added to a therapy regimen using other anti-neoplastic agents in treating a cancer patient.

The Fc-containing proteins described herein can be used to treat cell proliferative diseases, including cancer, which involve the unregulated and/or inappropriate proliferation of cells, sometimes accompanied by destruction of adjacent tissue and growth of new blood vessels, which can allow invasion of cancer cells into new areas, i.e. metastasis. Included within conditions treatable with the proteins described herein are non-malignant conditions that involve inappropriate cell growth, including colorectal polyps, cerebral ischemia, gross cystic disease, polycystic kidney disease, benign prostatic hyperplasia, and endometriosis. Other cell proliferative diseases that can be treated using the proteins of the present invention are, for example, cancers including mesotheliomas, squamous cell carcinomas, myelomas, osteosarcomas, glioblastomas, gliomas, carcinomas, adenocarcinomas, melanomas, sarcomas, acute and chronic leukemias, lymphomas, and meningiomas, Hodgkin's disease, Sézary syndrome, multiple myeloma, and lung, non-small cell lung, small cell lung, laryngeal, breast, head and neck, bladder, ovarian, skin, prostate, cervical, vaginal, gastric, renal cell, kidney, pancreatic, colorectal, endometrial, and esophageal, hepatobiliary, bone, skin, and hematologic cancers, as well as cancers of the nasal cavity and paranasal sinuses, the nasopharynx, the oral cavity, the oropharynx, the larynx, the hypolarynx, the salivary glands, the mediastinum, the stomach, the small intestine, the colon, the rectum and anal region, the ureter, the urethra, the penis, the testis, the vulva, the endocrine system, the central nervous system, and plasma cells.

The Fc-containing proteins described herein can find further use in other kinds of conditions where it is beneficial to deplete certain cell types. For example, depletion of human eosinophils in asthma, excess human B cells in systemic lupus erythematosus, excess human Th2 T cells in autoimmune conditions, or pathogen-infected cells in infectious diseases can be beneficial.

Pharmaceutical Compositions

The invention includes pharmaceutical compositions comprising the Fc-containing proteins described herein, such as antibodies or Fc fusion proteins. Such compositions comprise a therapeutically effective amount of an Fc-containing protein having an altered Fc region with one or more additional components such as a physiologically acceptable carrier, excipient, or diluent. Such additional components can include buffers, carbohydrates, polyols, amino acids, chelating agents, stabilizers, and/or preservatives, among many possibilities.

Dosing and Methods of Administration

Compositions comprising Fc-containing proteins comprising an altered Fc region described above can be administered by any appropriate means including, but not limited to, parenteral, topical, oral, nasal, vaginal, rectal, or pulmonary (by inhalation) administration. If injected, the composition(s) can be administered intra-articularly, intravenously, intraarterially, intramuscularly, intraarticularly, intraperitoneally, subcutaneously by bolus injection or continuous infusion. Localized administration, that is, at the site of disease, such as direct injection into a tumor, is contemplated, as are transdermal delivery and sustained release from implants or skin patches. Delivery by inhalation includes, for example, nasal or oral inhalation, use of a nebulizer, inhalation in aerosol form, and the like. Administration via a suppository inserted into a body cavity can be accomplished, for example, by inserting a solid form of the composition in a chosen body cavity and allowing it to dissolve. Other alternatives include eye drops, oral preparations such as pills, lozenges, syrups, and chewing gum, and topical preparations such as lotions, gels, sprays, and ointments. In most cases, therapeutic molecules that are polypeptides such as those described herein can be administered topically or by injection or inhalation.

The Fc-containing proteins described herein can be administered at any dosage, frequency, and duration that can be effective to treat the condition being treated. The therapeutically effective dosage depends on the molecular nature of the Fc-containing protein and the nature of the disorder being treated. Treatment may be continued as long as necessary to achieve the desired results. The Fc-containing protein can be administered as a single dosage or as a series of dosages given periodically, including multiple times per day, daily, every other day, twice a week, three times per week, weekly, every other week, monthly, every six weeks, every two months, every three, four, five or six months, among other possible dosage regimens. The periodicity of treatment may or may not be constant throughout the duration of the treatment. For example, treatment may initially occur at weekly intervals and later occur every other week or at longer intervals as mentioned above. Treatments having durations of days, weeks, months, or years are encompassed by the invention. Treatment may be discontinued and then restarted. Maintenance doses may be administered after an initial treatment.

Dosage may be measured as milligrams per kilogram of body weight (mg/kg) or as milligrams per square meter of skin surface (mg/m$^2$) or as a fixed dose, irrespective of height or weight. All of these are standard dosage units in the art. A person's skin surface area is calculated from her height and weight using a standard formula. With respect to the proteins containing an altered Fc region described herein, dosages can range from about 0.01 mg/kg to about 70 mg/kg, optionally from about 0.1 mg/kg to about 20 mg/kg, from about 0.1 mg/kg to about 5 mg/kg, from about 0.3 mg/kg to about 3 mg/kg, or about 2.5 mg/kg. Alternatively, patients of all sizes can receive the same dosage, ranging from about 1 mg to about 500 mg, optionally from about 10 mg to about 100 mg, from about 25 mg to about 50 mg, from about 100 mg to about 300 mg, or from about 100 mg to about 200 mg. Alternatively, the dosage may be from about 5 mg/m$^2$ to about 800 mg/m$^2$, from about 10 mg/m$^2$ to about 600 mg/m$^2$, or from about 25 mg/m$^2$ to about 500 mg/m$^2$. Dosages may or may not be constant throughout the duration of the treatment. For example, dosage may steadily escalate throughout the duration of the treatment. Alternatively, a first dose may be higher than subsequent doses. As a further alternative, dosage may be reduced at later stages of the treatment.

The foregoing description of the specific embodiments reveals the general nature of the invention so that others can readily modify and/or adapt such embodiments for various applications without departing from the generic concepts presented herein. Any such adaptions or modifications are intended to be embraced within the meaning and range of equivalents of the disclosed embodiments. The following examples are meant to be exemplary and are not meant to limit the scope of the invention. Phraseology and terminology employed in these examples are for the purpose of description and not of limitation.

EXAMPLES

Example 1: Construction and Screening of Libraries of Altered Fc Regions as Fc Heterodimers Library Construction and Primary Screening Libraries of nucleic acids encoding either an scFv-Fc containing the charge pair substitutions E356K and D399K or an Fc polypeptide chain ("dummy Fc") containing the charge pair substitutions K392D and K409D, with additional alterations at selected sites within the Fc-encoding regions, were created using PCR. For each site within the Fc selected for substitution, the nucleic acid was changed such that Fc regions with all twenty different amino acids at the selected site would be generated. Each codon in the nucleic acid was randomized independently so that the nucleic acid molecules in the resulting library were each potentially modified within only one codon. One group of sites was entirely within the lower hinge region (residues 230, 231, 232, 233, 234, 235, 236, 237, and 238; see FIG. 2). The library containing nucleic acids with mutations at sites encoding these residues was referred to as the "Tier 1" library. Another group of sites were within the $C_H2$ region and were either close to or part of the area that contacts FcγRIIIA (239, 241, 255, 256, 258, 264, 265, 267, 268, 269, 270, 272, 276, 280, 285, 286, 290, 294, 295, 296, 298, 300, 307, 309, 315, 326, 327, 328, 330, 332, 333, 334, 337, and 339; see FIG. 2). The library containing nucleic acids with mutations at sites encoding these residues was referred to as the "Tier 2" library. A third group included sites within the $C_H2$ region that were solvent-exposed, but were not close to or part of the area that contacts FcγRIIIA (243, 246, 248, 249, 251, 252, 253, 254, 260, 274, 275, 278, 279, 282, 283, 284, 287, 288, 289, 292, 293, 301, 302, 303, 305, 310, 311, 312, 313, 314, 317, 318, 320, 322, 324, 335, 336, 338, and 340; see FIG. 2). The library containing nucleic acids with mutations at sites encoding these residues was referred to as the "Tier 3" library. FIG. 2 shows the positions of these sites within a human IgG1 Fc region.

In more detail, a DNA fragment encoding the scFv of the M315 antibody (a rat-anti-mouse NKG2D antibody) fused to a human IgG1 Fc polypeptide with E356K and D399K charge pair mutations in $C_H3$ domain was subcloned into the mammalian expression vector pTT5. Zhang et al. (2009), Protein Expression and Purification 65(1): 77-82. A DNA fragment encoding a hulgG1 Fc polypeptide with K392D and K409D charge pair mutations in the $C_H3$ domain was also subcloned into pTT5. The six small Fc libraries described above were made using splice overhang extension by polymerase chain reaction (SOE by PCR) as described below. See, e.g., Warrens et al. (1997), Gene 186: 29-35, the portions of which describe this method are incorporated herein by reference.

The libraries were made as follows. For each of the 82 selected codons within each Fc-encoding region, an oligonucleotide randomized at the first two positions of the codon and having either a G or a C at third position (an "NNG/C codon") was made (an "NNG/C oligonucleotide"). This NNG/C codon was placed in the middle of the NNG/C oligonucleotide with about 21 bases extending upstream and downstream. The NNG/C oligonucleotide was oriented such that its 5' end was upstream of its 3' end in the Fc-encoding region. Accordingly, "reverse oligonucleotides" that match the upstream 21 bases of the NNG/C oligonucleotides were synthesized individually. A universal downstream primer was combined with each of the NNG/C oligonucleotides and subjected to polymerase chain reaction (PCR) to produce downstream fragments. Similarly, a universal upstream oligonucleotide and each of the reverse oligonucleotides were combined and subjected to PCR reactions to make upstream DNA fragments. Alternatively, the NNG/C oligonucleotide may point upstream, and the reverse primer may point downstream. In this case the initial PCR reactions described above would include the NNG/C oligonucleotide plus the upstream oligonucleotide in one PCR reaction to produce an upstream fragment and the reverse oligonucleotide and the downstream oligonucleotide in another PCR reaction to produce a downstream fragment. The upstream and downstream PCR fragments were purified using agarose gels, and the amounts of these PCR products were quantified. The same molar amounts of individual upstream and downstream DNA fragments were combined with the universal upstream and downstream primers for a second round PCR reaction to assemble the full length PCR product. Full length PCR fragments were then purified from agarose gels, and equal amounts of individual full length fragments from a tier were combined, digested with restriction enzymes Sal I and BamH I, and inserted into an expression vector.

Figure 3:
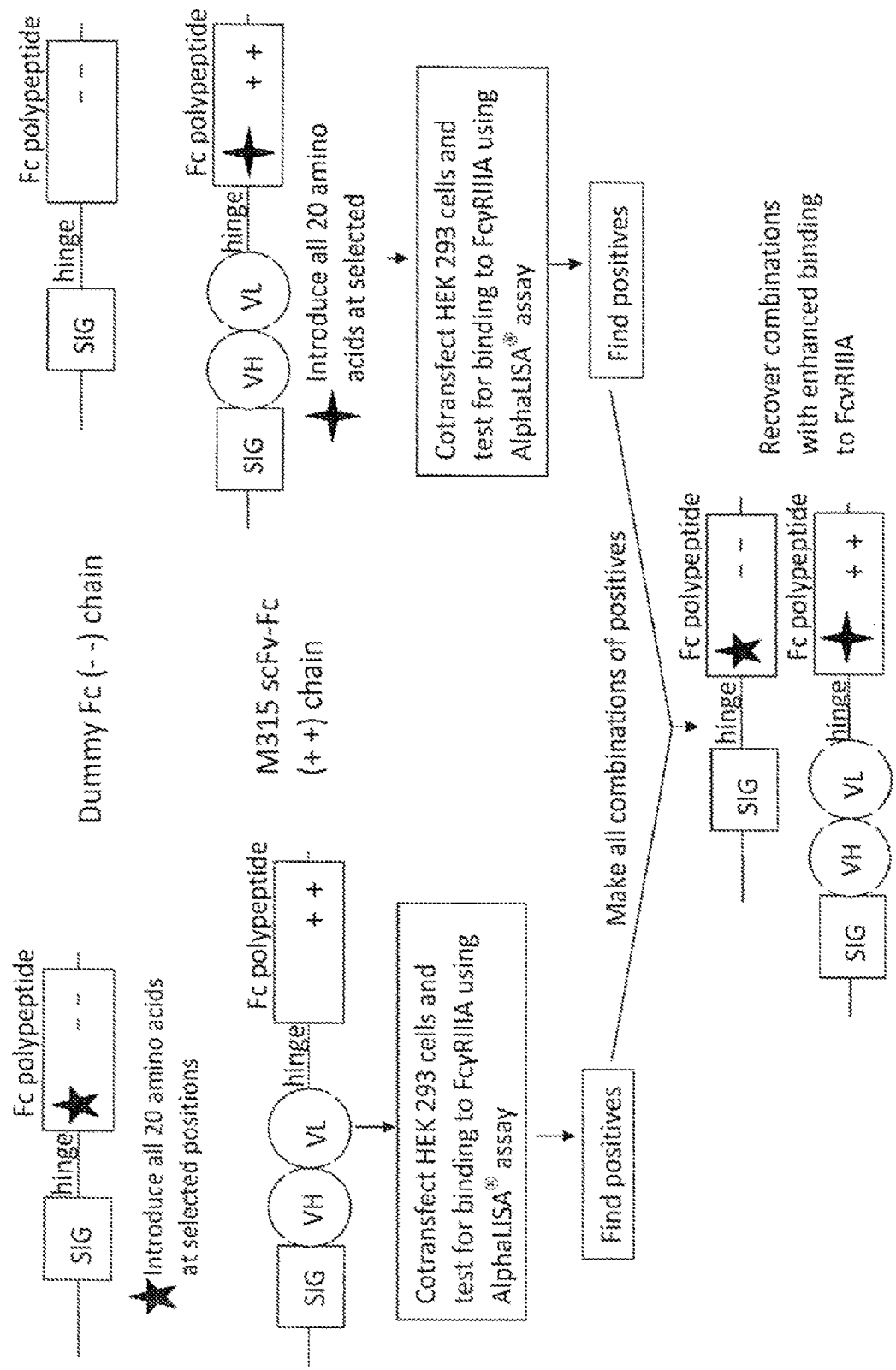
FIG. 3: Diagram showing the primary screening and initial combinatorial screening for substitutions that enhance binding to FcγRIIIA. The rectangle labeled "SIG" represents a polynucleotide encoding a signal sequence, which facilitates protein secretion from mammalian cells. A region encoding a hinge region is represented by a horizontal line labeled "hinge." A rectangle labeled "Fc polypeptide" represents a polynucleotide encoding an Fc polypeptide chain. The five-pointed and four-pointed stars mean that the polynucleotides encoding the Fc polypeptide chains contain one randomized codon in each molecule at selected positions as explained in Example 1. The circles labeled "VH" and "VL" represent regions encoding a heavy chain variable region and a light chain variable region, respectively. The "++" and "−−" signs in the rectangles labeled "Fc polypeptide" mean that these regions include mutations such that the encoded Fc polypeptide chain will have the substitutions E356K, D399K and K392D, K409D, respectively.

A total of six libraries were made. Three libraries, a Tier 1, a Tier 2, and a Tier 3 library, having mutations in a nucleic acid encoding an scFv-Fc were made. Similarly, a Tier 1, a Tier 2, and a Tier 3 library having mutations at the same positions within the Fc-encoding region in a nucleic acid encoding a dummy Fc were made. As illustrated diagrammatically in FIG. 3, initial screening was performed as follows. The libraries were introduced into Escherichia coli, and enough individual colonies were picked such that at least three times as many colonies were picked as there were different variants in the library. For example, each Tier 1 library contained twenty different amino acids at each of nine sites, for a total of 180 different variants. In this case, ten microtiter plates of colonies (96 wells/plate for a total of about 960) were picked and grown. Plasmid DNA was isolated. Each Tier 2 and Tier 3 library contained twenty different amino acids at each of 34 and 39 sites for a total of 680 and 780 different variants, respectively. Accordingly, 45 plates of colonies (for a total of 4320) were picked for each Tier 2 and Tier 3 library, and plasmid DNA was isolated. These mutated plasmid DNAs were combined with unaltered DNAs (if the altered DNA was an scFv-Fc, the unaltered DNA was a dummy Fc, and vice versa, as shown in FIG. 2) and used to transfect HEK 293 cells (a transformed human embryonic kidney cell line). Transfectants were cultured, and the culture medium was assayed using an AlphaLISA assay using reagents purchased from Perkin Elmer (catalog numbers 6760002 and AL109M).

Briefly, the AlphaLISA® assay was performed as follows. Cell culture medium from the transfected HEK 293 cells was added to wells containing streptavidin-coated donor beads (Perkin Elmer catalog number 6760002), a biotinylated human IgG antibody (which binds to the donor beads via the streptavidin-biotin interaction), acceptor beads (Perkin Elmer catalog number AL109M) conjugated to an anti-glutathione S-transferase (GST) antibody, a GST-tagged version of human FcγRIIIA (which binds to the acceptor beads via the GST-anti-GST antibody interaction and which binds to the donor beads via the interaction of FcγRIIIA with the biotinylated human IgG antibody). In the absence of a competitor (such as an scFv-Fc/Fc), when the wells are illuminated with light at 680 nm, the donor beads are activated. If the acceptor beads are in close physical proximity to the activated donor cells, they will be activated by the donor beads to emit fluorescence at about 615 nm. In the presence of a competitor that binds to FcγRIIIA (such as an scFv-Fc/Fc), this signal will be decreased since the donor and acceptor beads will be allowed to drift apart when the competitor, rather than the biotinylated human IgG antibody, binds to FcγRIIIA, particularly if the competitor binds more effectively to FcγRIIIA than the biotinylated human IgG antibody.

The cell culture supernatants that inhibited the signal to a greater extent than did supernatants from cells transfected with unmutated (except for the charge pair mutations which were also included in the libraries) versions of the scFv-Fc and dummy Fc were retested twice more to confirm that they were positive. In the third round of testing, tests were performed in duplicate. The Fc-encoding regions of the plasmids encoding these scFv-Fc's or dummy Fc's that yielded a positive signal were sequenced.

Tables 1 and 2 below show the data only from these positive transfectants resulting from the Tier 1, 2, and 3 libraries that were mutated in the scFv-Fc- and dummy Fc-encoding nucleic acids, respectively.

TABLE 1

| | | Primary positive hits from scFv-Fc libraries | | | | | |
|---|---|---|---|---|---|---|---|
| | | 1st round of primary screen | | 2nd round of screen | | 3rd round of screen | |
| Tier | Substitution | Alpha signal | % inhibition | Alpha signal | % inhibition | Alpha signal | % inhibition |
| | no substitution | 76003 | 0.0 | 80429 | 0.0 | 78582 | 0.0 |
| 1 | L234Y | 55075 | 27.5 | 45915 | 42.9 | 50495 | 35.7 |
| 1 | L235S | 7789 | 89.8 | 6262 | 92.2 | 7025 | 91.1 |
| 1 | G236Y | 64581 | 15.0 | 61733 | 23.2 | 62157 | 20.9 |
| 2 | S239D | 24347 | 68.0 | 16863 | 79.0 | 21421 | 72.7 |
| 2 | S239N | 31926 | 58.0 | 26111 | 67.5 | 24500 | 68.8 |
| 3 | F243L | 46048 | 39.4 | 57412 | 28.6 | 55205 | 29.7 |
| 3 | F243V | 41730 | 45.1 | 42089 | 47.7 | 40375 | 48.6 |
| 3 | F243I | 29972 | 60.6 | 21670 | 73.1 | 21364 | 72.8 |
| 3 | I253K | 57394 | 24.5 | 52131 | 35.2 | 51343 | 34.7 |
| 2 | T256Q | 26517 | 65.1 | 19094 | 76.3 | 20846 | 73.5 |
| 2 | E258V | 23310 | 69.3 | 19494 | 75.8 | 22403 | 71.5 |
| 2 | H268E | 54810 | 27.9 | 56630 | 29.6 | 57069 | 27.4 |

TABLE 1-continued

Primary positive hits from scFv-Fc libraries

| | | 1st round of primary screen | | 2nd round of screen | | 3rd round of screen | |
|---|---|---|---|---|---|---|---|
| Tier | Substitution | Alpha signal | % inhibition | Alpha signal | % inhibition | Alpha signal | % inhibition |
| 2 | H268K | 60627 | 20.2 | 62217 | 22.6 | 61602 | 21.6 |
| 3 | A287F | 39907 | 47.5 | 33473 | 58.4 | 25468 | 67.6 |
| 3 | K288I | 56406 | 25.8 | 57487 | 28.5 | 57289 | 27.1 |
| 2 | K290G | 52396 | 31.1 | 53843 | 33.1 | 55724 | 29.1 |
| 2 | K290S | 57139 | 24.8 | 55906 | 30.5 | 54625 | 30.5 |
| 2 | K290W | 53869 | 29.1 | 52574 | 34.6 | 59537 | 24.2 |
| 2 | K290Q | 37430 | 50.8 | 36682 | 54.4 | 40252 | 48.8 |
| 2 | K290Y | 9168 | 87.9 | 7893 | 90.2 | 10215 | 87.0 |
| 2 | E294L | 24347 | 68.0 | 22911 | 71.5 | 18221 | 76.8 |
| 2 | Y296W | 25317 | 66.7 | 21765 | 72.9 | 24756 | 68.5 |
| 2 | Y296L | 58469 | 23.1 | 60581 | 24.7 | 64317 | 18.2 |
| 2 | S298A | 17868 | 76.5 | 25331 | 68.5 | 27486 | 65.0 |
| 2 | S298C | 12163 | 84.0 | 10352 | 87.1 | 13443 | 82.9 |
| 2 | T307S | 44581 | 41.3 | 46542 | 42.1 | 51427 | 34.6 |
| 2 | T307E | 21667 | 71.5 | 18943 | 76.4 | 25776 | 67.2 |
| 2 | T307G | 32517 | 57.2 | 36732 | 54.3 | 38498 | 51.0 |
| 2 | L309S | 60518 | 20.4 | 61549 | 23.5 | 63542 | 19.1 |
| 2 | L309K | 23426 | 69.2 | 18876 | 76.5 | 27215 | 65.4 |
| 2 | L309E | 25050 | 67.0 | 21115 | 73.7 | 25441 | 67.6 |
| 2 | N315A | 23792 | 68.7 | 19723 | 75.5 | 28619 | 63.6 |
| 2 | N315S | 25958 | 65.8 | 19461 | 75.8 | 28793 | 63.4 |
| 2 | A330M | 55444 | 27.1 | 50996 | 36.6 | 57992 | 26.2 |
| 2 | I332E | 18900 | 75.1 | 20396 | 74.6 | 18450 | 76.5 |
| 2 | K334A | 51677 | 32.0 | 54810 | 31.9 | 56456 | 28.2 |
| 2 | K334M | 22262 | 70.7 | 19782 | 75.4 | 24376 | 69.0 |

TABLE 2

Primary positive hits from dummy Fc libraries

| | | 1st round of primary screen | | 2nd round of screen | | 3rd round of screen | |
|---|---|---|---|---|---|---|---|
| Tier | Substitution | Alpha signal | % inhibition | Alpha signal | % inhibition | Alpha signal | % inhibition |
| | no substitution | 76003 | 0.0 | 80429 | 0.0 | 78582 | 0.0 |
| 2 | S239D | 6120 | 91.9 | 6155 | 92.3 | 9874 | 87.4 |
| 2 | S239E | 32510 | 57.2 | 34836 | 56.7 | 33673 | 57.1 |
| 2 | S239E + K340N | 11484 | 84.9 | 11757 | 85.4 | 26132 | 66.7 |
| 3 | F243M | 43121 | 43.3 | 37720 | 53.1 | 32424 | 58.7 |
| 3 | F243L | 20563 | 72.9 | 18203 | 77.4 | 18794 | 76.1 |
| 3 | F243V | 38776 | 49.0 | 32101 | 60.1 | 29266 | 62.8 |
| 3 | F243I | 29808 | 60.8 | 25768 | 68.0 | 23762 | 69.8 |
| 3 + 2 | F243V + S239T | 11564 | 84.8 | 13705 | 83.0 | 12525 | 84.1 |
| 3 | K246W | 60773 | 20.0 | 57107 | 29.0 | 51701 | 34.2 |
| 3 | K246E | 58947 | 22.4 | 62557 | 22.2 | 53343 | 32.1 |
| 3 | K246S | 45132 | 40.6 | 42377 | 47.3 | 37902 | 51.8 |
| 3 | K246V | 43826 | 42.3 | 44452 | 44.7 | 42791 | 45.5 |
| 3 | K248Y | 52092 | 31.5 | 51035 | 36.5 | 46986 | 40.2 |
| 3 | K248L | 24674 | 67.5 | 23108 | 71.3 | 24831 | 68.4 |
| 3 | M252D | 60526 | 20.4 | 58066 | 27.8 | 60269 | 23.3 |
| 3 | I253V | 58498 | 23.0 | 61503 | 23.5 | 58403 | 25.7 |
| 2 | R255S | 59331 | 21.9 | 49837 | 38.0 | 61045 | 22.3 |
| 2 | R255N | 47547 | 37.4 | 48542 | 39.6 | 44532 | 43.3 |
| 2 | T256V | 30486 | 59.9 | 31764 | 60.5 | 28809 | 63.3 |
| 2 | E258S | 60338 | 20.6 | 57893 | 28.0 | 61591 | 21.6 |
| 3 | K288T | 55695 | 26.7 | 53102 | 34.0 | 50325 | 36.0 |
| 2 | K290G | 20557 | 73.0 | 20088 | 75.0 | 38478 | 51.0 |
| 2 | K290F | 58476 | 23.1 | 55435 | 31.1 | 60116 | 23.5 |
| 2 | E294L | 30129 | 60.4 | 35365 | 56.0 | 32178 | 59.1 |
| 3 | V302Q | 40294 | 47.0 | 35937 | 55.3 | 33446 | 57.4 |
| 2 | T307P | 18993 | 75.0 | 20019 | 75.1 | 14102 | 82.1 |
| 2 | L309C | 59701 | 21.4 | 55632 | 30.8 | 61787 | 21.4 |
| 3 | Q311M | 13143 | 82.7 | 11115 | 86.2 | 9798 | 87.5 |
| 2 | A330V | 56425 | 25.8 | 54114 | 32.7 | 58445 | 25.6 |
| 2 | I332E | 10781 | 85.8 | 9879 | 87.7 | 11532 | 85.3 |
| 2 | K334L | 26701 | 64.9 | 23400 | 70.9 | 25092 | 68.1 |
| 2 | K334V | 27080 | 64.4 | 26926 | 66.5 | 30164 | 61.6 |
| 2 | K334V + D413N | 20192 | 73.4 | 21412 | 73.4 | 25438 | 67.6 |
| 2 | A339T | 56391 | 25.8 | 58448 | 27.3 | 49783 | 36.6 |

By calculation, a total of about 1640 different variants were included in the scFv-Fc-encoding Tier 1, 2, and 3 libraries combined. The same number of variants was included in the dummy Fc-encoding Tier 1, 2, and 3 libraries combined. Given the number of variants tested, it was likely that all variants were represented at least once among the transfectants tested. However, only 37 different scFv-Fc's and 34 different dummy Fc's gave a positive signal in this primary screen. Many of these variants were recovered multiple times. Thus, in total, only about 2% of the 1640 different variants included in the libraries yielded a positive signal.

Combinatorial Screening of Positive Hits

All of the substitutions identified in the primary screen in the dummy Fc libraries (as shown in Table 2) were combined with all substitutions identified in the primary screen of the scFv-Fc libraries (as shown in Table 1) to identify combinations that could bind FcγRIIIA more effectively. Thus, in total 37×34=1258 combinations were tested. Surprisingly, only the following 21 of the 1258 combinations tested showed strong competition to the biotin-huIgG1/FcγIIIA interaction in an AlphaLISA assay: (1) E294L in the dummy Fc and E294L in the scFv-Fc; (2) E294L in the dummy Fc and Y296L in the scFv-Fc; (3) E294L in the dummy Fc and K290G in the scFv-Fc; (4) E294L in the dummy Fc and K290S in the scFv-Fc; (5) E294L in the dummy Fc and S298A in the scFv-Fc; (6) E294L in the dummy Fc and T307G in the scFv-Fc; (7) T307P in the dummy Fc and T307G in the scFv-Fc; (8) T307P in the dummy Fc and K290G in the scFv-Fc; (9) T307P in the dummy Fc and Y296L in the scFv-Fc; (10) T307P in the dummy Fc and K290S in the scFv-Fc; (11) R255S in the dummy Fc and S298C in the scFv-Fc; (12) T307P in the dummy Fc and S298C in the scFv-Fc; (13) E294L in the dummy Fc and S298C in the scFv-Fc; (14) K334V in the dummy Fc and K290Y in the scFv-Fc; (15) T307P in the dummy Fc and L309E in the scFv-Fc; (16) E294L in the dummy Fc and L309E in the scFv-Fc; (17) T307P in the dummy Fc and L234Y in the scFv-Fc; (18) E294L in the dummy Fc and L234Y in the scFv-Fc; (19) Q311M in the dummy Fc and Y296W in the scFv-Fc; (20) Q311M in the dummy Fc and L234Y in the scFv-Fc; and (21) K334V in the dummy Fc and Y296W in the scFv-Fc. Thus, only a very small number of the combinations of Fc mutants tested showed highly synergistic binding to FcγIIIA.

Example 2: Construction and Characterization of Combination Variants in IgG Format To determine whether full length antibodies containing substitutions in their Fc regions would function to bind more effectively to FcγRIIIA, combinations of substitutions were made in a full length human anti-Protein X IgG1 antibody using the techniques described above. All the primary hits (see Tables 1 and 2) were mapped out on the Fc:FcγRIIIB co-crystal structure using Molecular Operating Environment (MOE), a molecular modeling program from Chemical Computing Group, Inc. Montreal Calif. See Protein Data Bank code 1T83. As noted in the legend to FIG. 1 above, the extracellular region of FcγRIIIB that is in this structure (shown in FIG. 1) is very similar in primary amino acid sequence to FcγRIIIA, such that it was considered likely that information from the Fc:FcγRIIIB co-crystal structure would be relevant to the Fc:FcγRIIIA interaction. Candidate substitutions which had mutations at Fc:FcγRIIIB interface (i.e., at Tier 2 positions shown in FIG. 2) were selected for further engineering based on the results of the primary screening and/or computer-assisted molecular modeling. In an effort to further enhance the Fc:FcγRIIIA interaction, additional substitutions in other parts of the Fc polypeptide were added to the Tier 2 substitutions. Specifically, substitutions within N-glycosylation site (N297-S298-T299), and/or near the P329 site in either Fc chain were explored using molecular modeling. Substitutions within both of these areas (i.e., S298C, S298A, A330M, and A330V) had been found in the primary screen. Combinations that appeared to be favorable based on molecular modeling as discussed below were constructed and tested for binding to FcγRIIIA and, in some cases, for activity in an ADCC assay.

In order to arrive at candidate combinations of substitutions and to eliminate substitutions that might create manufacturability issues (e.g., replacing another amino acid with a cysteine), structural analyses were performed using the Fc-FcγRIIIB crystal structures (Protein Data Bank Codes: 1T83, 1T89, and 1E4K), and binding energy calculations were carried out using the Genetic Algorithm for Protein Design (EGAD). Pokala, N and Handel, T M, J Mol Biol. 347(1): 203-227. (2005), the relevant portions of which are incorporated herein by reference. EGAD is a computational protein design algorithm that predicts changes in protein stability upon substitution one or more amino acid residues in a protein.

Substitutions at positions S298, A327, and A330 were identified that might improve Fc binding to FcγRIII using EGAD. Each of the three positions was changed to all other 19 amino acids in silico, and the change in the stability of the Fc-FcγRIII interaction was predicted. EGAD was also used to analyze some of the combinations of mutations that bound well to FcγRs according to the data reported above. Examples of substitutions that EGAD predicted might enhance binding to FcγRIIIA include S298C, S298I, S298V, S298T, A327Y, A327W, A327F, A327H, A330H, A330F, and A330M. AlphaLISA assay confirmed that some of the predicted mutations at positions S298 and A330 showed improved binding to the FcγRs. For example, the combination designated "W23," which has L234Y, K290Y, and Y296W mutations in one chain and S298T and K334V mutations in the other chain resulted from this approach.

Beneficial combinations were selected and incorporated into DNA encoding an anti-human Protein X huIgG1 heavy chain using the SOE by PCR technique described above. Heterodimeric huIgG1s were made by transiently transfecting HEK 293 cells at small scale. The crude supernatants were concentrated, and the buffer was exchanged. In such a way, a panel of heterodimeric huIgG1 antibodies containing novel Fc variants having multiple substitutions was created.

Figure 4:
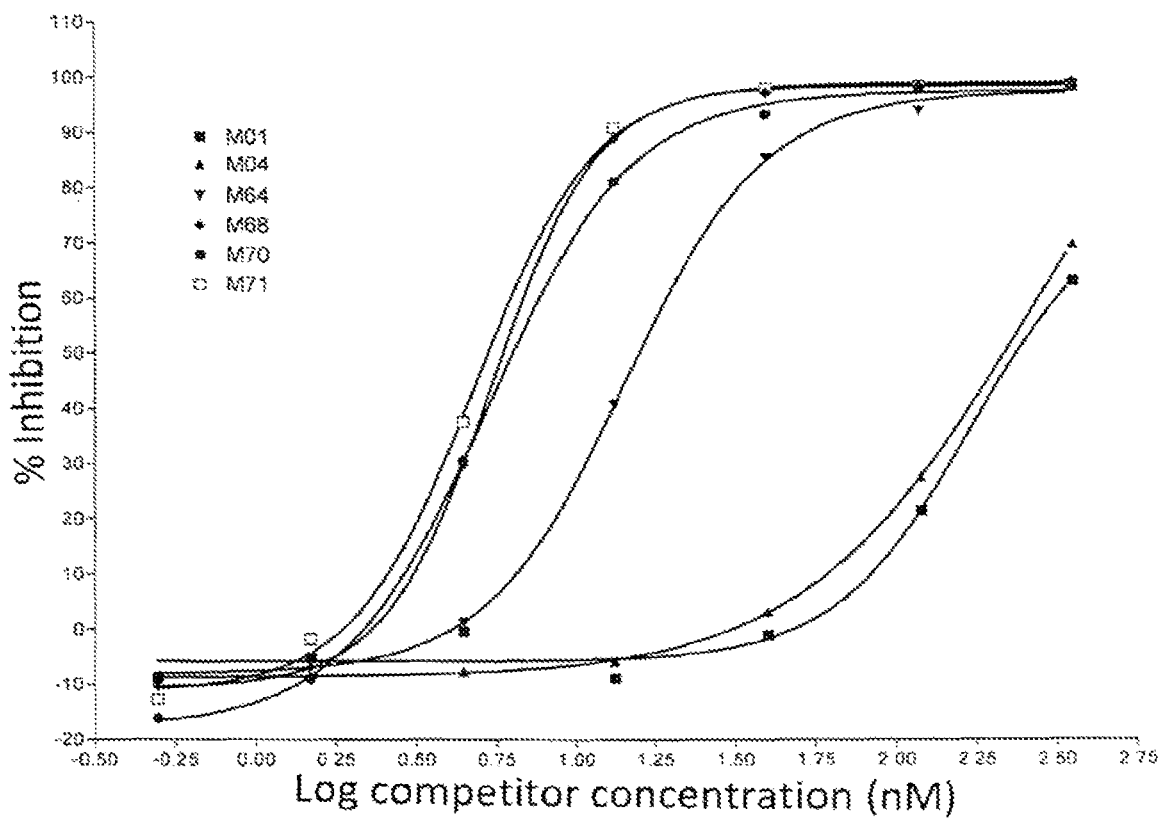
FIG. 4: Percent inhibition of AlphaLISA® signal by full length IgG1 antibodies containing variant Fc regions. The graph shows the percent inhibition of an AlphaLISA signal as a function of concentration of competitor. The various competitors, which are human IgG1 antibodies, are indicated by alias in the graph, and the substitutions contained in each competitor are indicated in Table 3.
Figure 5:
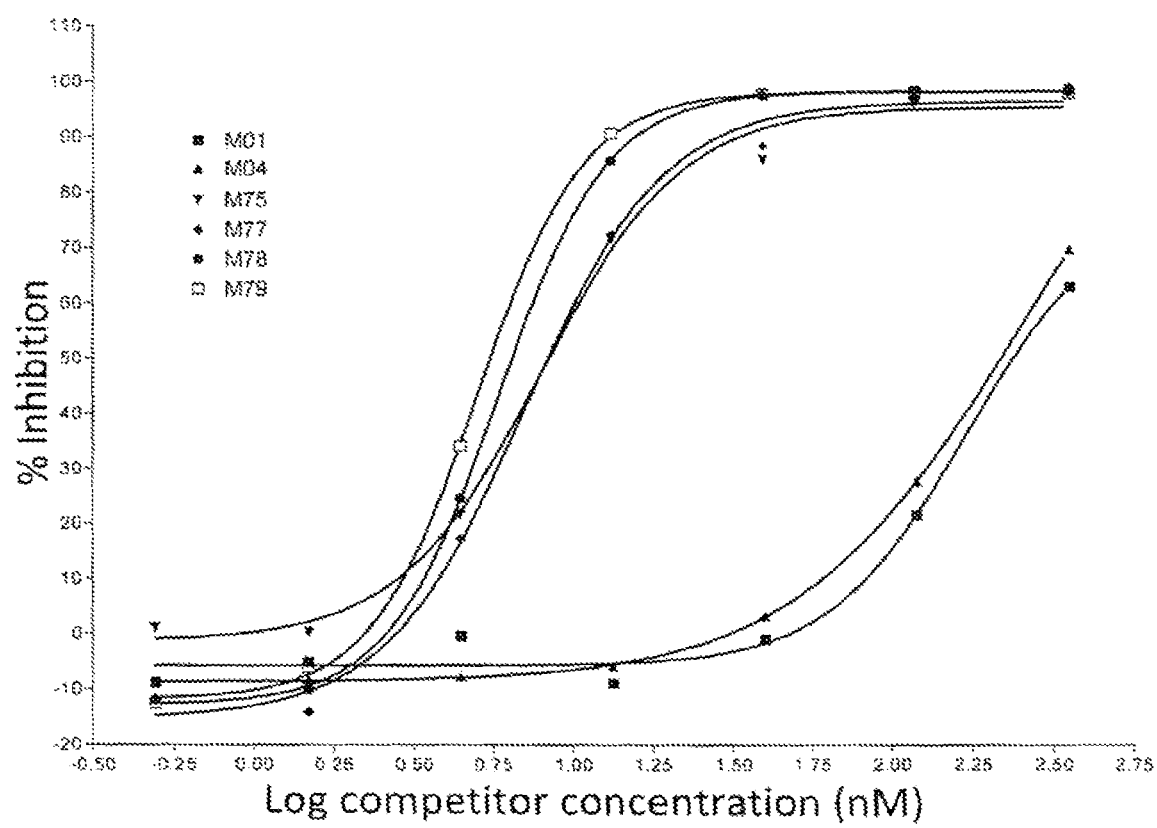
FIG. 5: Percent inhibition of AlphaLISA® signal by full length IgG1 antibodies containing variant Fc regions. The graph shows the percent inhibition of an AlphaLISA® signal as a function of concentration of competitor. The various competitors, which are human IgG1 antibodies, are indicated by alias in the graph, and the substitutions contained in each competitor are indicated in Table 3.
Figure 6:
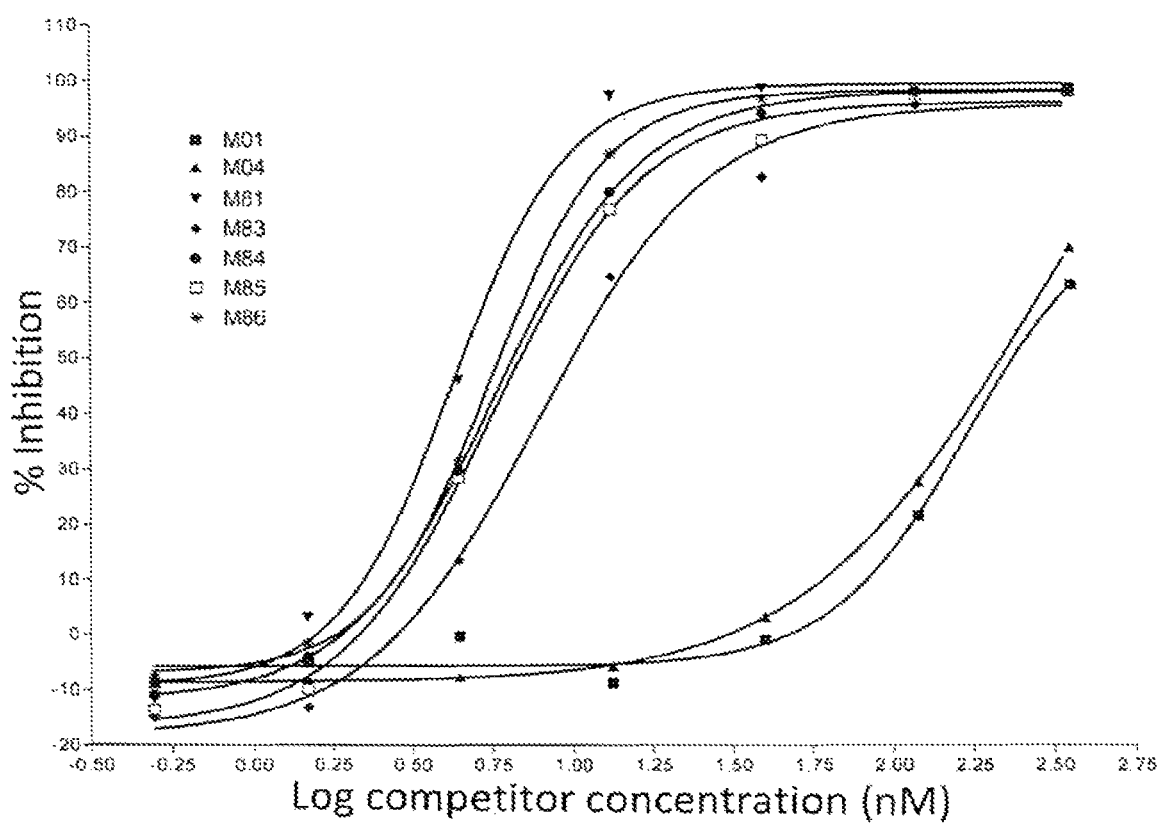
FIG. 6: Percent inhibition of AlphaLISA® signal by full length IgG1 antibodies containing variant Fc regions. The graph shows the percent inhibition of an AlphaLISA® signal as a function of concentration of competitor. The various competitors, which are human IgG1 antibodies, are indicated by alias in the graph, and the substitutions contained in each competitor are indicated in Table 3.

These substituted antibodies were tested for their ability to mediate ADCC in vitro and to bind to FcγRIIIA using the AlphaLISA assay at a variety of concentrations. FIGS. 4-6 show the percent inhibition of AlphaLISA® signal as a function of the concentration of the competitor antibody. In the Tables 3 and 4 below, such data is presented as an "$EC_{50}$", which is the concentration of antibody at which half of the maximal inhibition of the AlphaLISA® signal is achieved.

ADCC assays were performed as follows. Cell lines having high (tumor cell line SKBR3), medium (tumor cell line JIMT1), and low (tumor cell line MCF7) Protein X expression were used. These Protein X-expressing target cells were labeled with carboxyfluorescein succinimidyl ester (CFSE) and then washed once with phosphate buffered saline (PBS) before being deposited into 96-well microtiter plates with V-shaped wells. Purified NK cells from an FcγRIIIA 158F/158F donor were added to each well. The heterodimeric human anti-Protein X IgG1 antibodies and an isotype-matched control antibody were diluted in a 1:3 series and added to each well. The cells were incubated at 37° C. with 5% $CO_2$ for 3.5 hrs. The cells were spun down and re-suspended in 1×FACS buffer (1× phosphate buffered saline (PBS) containing 0.5% fetal bovine serum (FBS)) with the dye TO-PRO®-3 iodide (Molecular Probes, Inc. Corporation, Oregon, USA), which stains dead cells, before analysis by fluorescence activated cell sorting (FACS). The percentage of cell killing was calculated by dividing the number of dead cells (stained TO-PRO®-3 iodide) by number of total cells (stained with CFSE).

Figure 7:
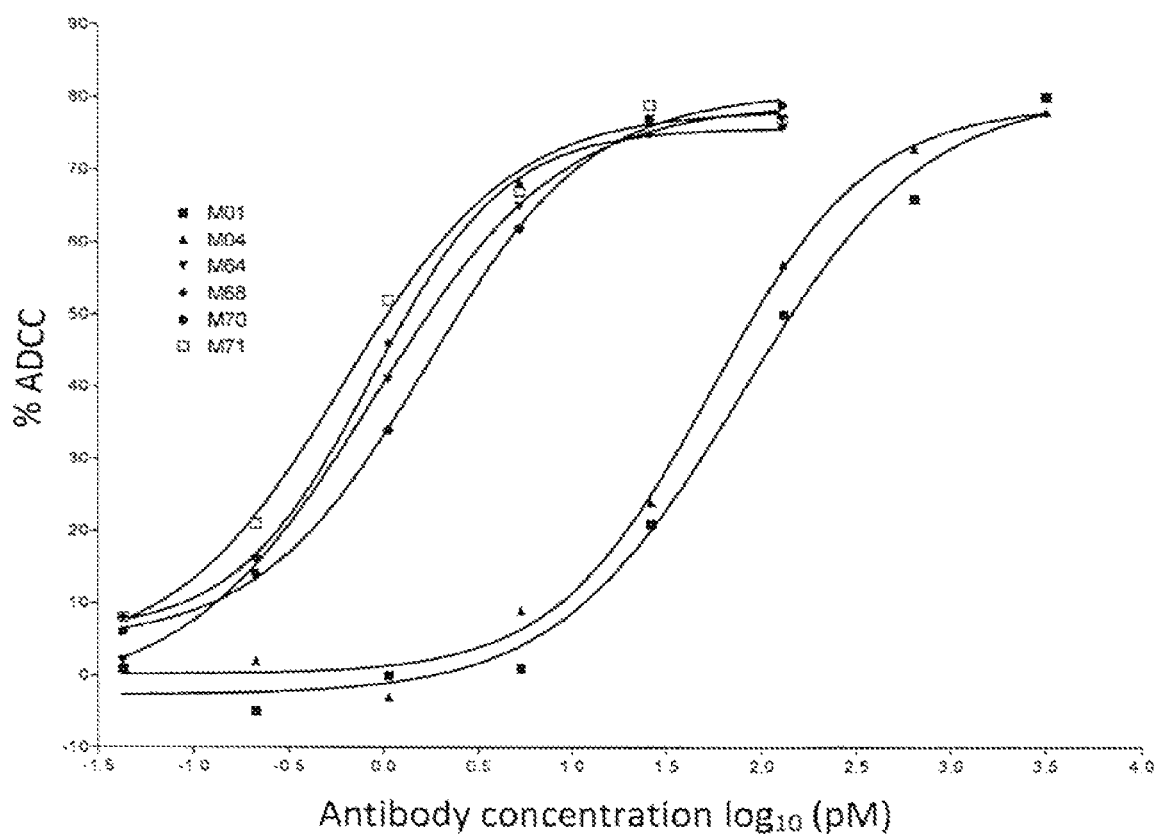
FIG. 7: Percent cell killing by full length IgG1 antibodies containing variant Fc regions. The graph shows the percentage of cells killed in an assay for antibody-dependent cellular cytotoxicity (% ADCC) versus antibody concentration. The various human IgG1 antibodies used in these assays are indicated by alias in the graph, and the substitutions contained in each antibody are indicated in Table 3.
Figure 8:
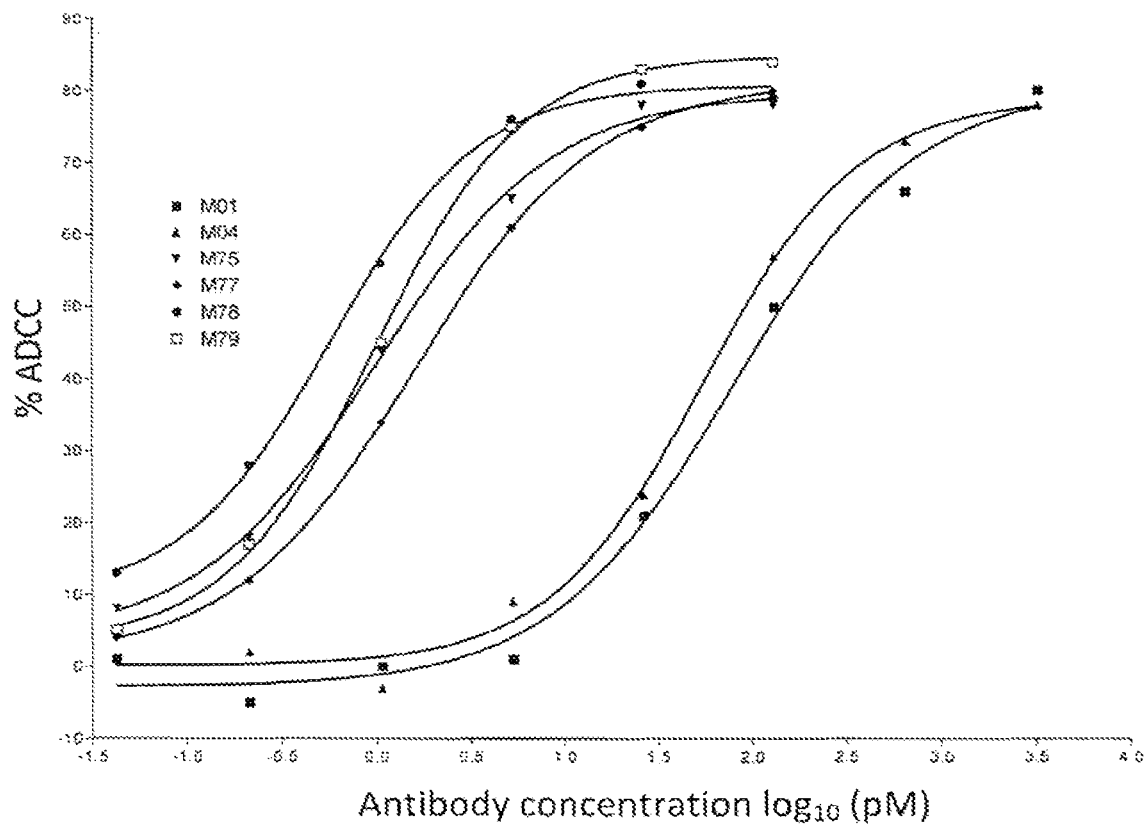
FIG. 8: Percent cell killing by full length IgG1 antibodies containing variant Fc regions. The graph shows the percentage of cells killed in an assay for antibody-dependent cellular cytotoxicity (% ADCC) versus antibody concentration. The various human IgG1 antibodies used in these assays are indicated by alias in the graph, and the substitutions contained in each antibody are indicated in Table 3.
Figure 9:
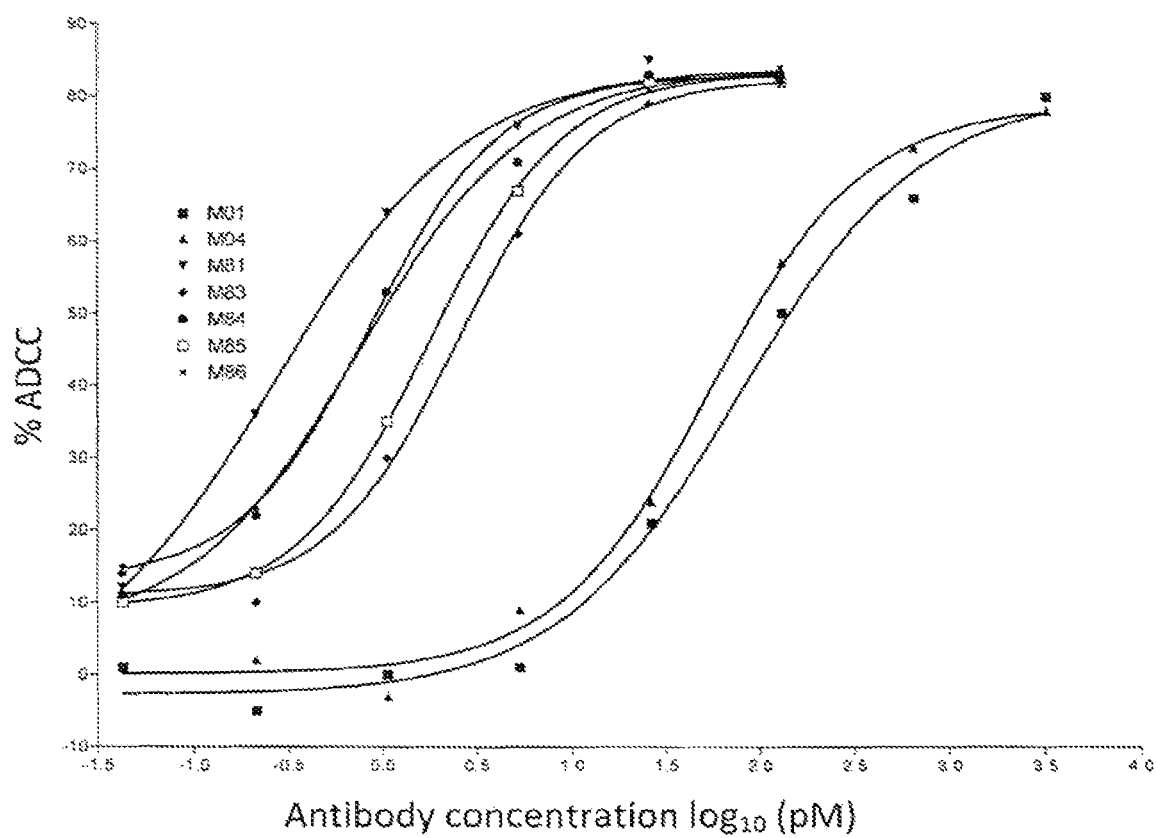
FIG. 9: Percent cell killing by full length IgG1 antibodies containing variant Fc regions. The graph shows the percentage of cells killed in an assay for antibody-dependent cellular cytotoxicity (% ADCC) versus antibody concentration. The various human IgG1 antibodies used in these assays are indicated by alias in the graph, and the substitutions contained in each antibody are indicated in Table 3.

FIGS. 7-9 show the percentage of cells killed as a function of antibody concentration. $EC_{50}$'s determined from such data are shown in Table 3. These data indicated that all fourteen of the antibodies containing variant Fc regions were very potent in killing tumor cells, each having an $EC_{50}$ of about 1 pM, which was much lower than the $EC_{50}$ of an unaltered antibody or an antibody containing only charge pair mutations. Table 3. Further, lower $EC_{50}$'s for ADCC generally correlated with lower $EC_{50}$s for FcγRIIIA binding, which would be expected since binding to FcγRIIIA is a prerequisite for activity in this ADCC assay.

TABLE 3

FcγRIIIA binding and ADCC activity of human IgG1 antibodies containing Fc variants

| Alias | Negative/negative chain (K392D, K409D) | Positive/positive chain (E356K, D399K) | FcγRIIIA (158F) $EC_{50}$ (nM) | ADCC $EC_{50}$ (pM) |
|---|---|---|---|---|
| M01 | wild type (no charge pair substitutions) | wild type (no charge pair substitution) | 103.2 | 75.00 |
| M04 | charge pair substitutions only | charge pair substitutions only | 86.97 | 55.50 |
| M64 | K334V | Y296W + S298C | 18.3 | 0.75 |
| M68 | K334V | L234Y + Y296W + S298C | 5.44 | 0.82 |
| M70 | L235S + S239D + K334V | L234Y + K290Y + Y296W | 5.28 | 1.54 |
| M71 | L235S + S239D + K334V | L234Y + Y296W + S298C | 4.82 | 0.63 |
| M75 | Q311M + K334V (SEQ ID NO: 8) | L234Y + F243V + Y296W | 7.94 | 1.01 |
| M77 | Q311M + K334V (SEQ ID NO: 8) | L234Y + E294L + Y296W (SEQ ID NO: 10) | 7.07 | 1.47 |
| M78 | Q311M + K334V (SEQ ID NO: 8) | L234Y + Y296W + S298C | 5.84 | 0.53 |
| M79 | S239D + K334V | L234Y + K290Y + Y296W | 5.04 | 0.97 |
| M81 | S239D + K334V | L234Y + Y296W + S298C | 4.25 | 0.31 |
| M83 | F243V + K334V | L234Y + K290Y + Y296W | 7.85 | 2.42 |
| M84 | F243V + K334V | L234Y + Y296W + S298C | 5.77 | 0.79 |
| M85 | E294L + K334V | L234Y + K290Y + Y296W | 5.66 | 1.71 |
| M86 | E294L + K334V | L234Y + Y296W + S298C | 5.57 | 0.79 |
| W23 | S298T + K334V (SEQ ID NO: 16) | L234Y + K290Y + Y296W (SEQ ID NO: 18) | 5.23 | 0.68 |

TABLE 4

FcγRIIIA binding of human IgG1 antibodies containing Fc variants

| Alias | Negative/negative chain (K392D, K409D) | Positive/positive chain (E356K, D399K) | FcγRIIIA (158F) $EC_{50}$ (nM) | FcγRIIIA (158V) $EC_{50}$ (nM) |
|---|---|---|---|---|
| M77 | Q311M + K334V (SEQ ID NO: 8) | L234Y + E294L + Y296W (SEQ ID NO: 10) | 13.2 | 10.87 |
| M138 | E233L + Q311M + K334V (SEQ ID NO: 12) | L234Y + E294L + Y296W (SEQ ID NO: 10) | 12.74 | 8.45 |
| M142 | L234I + Q311M + K334V (SEQ ID NO: 14) | L234Y + E294L + Y296W (SEQ ID NO: 10) | 10.37 | 8.25 |
| W23 | S298T + K334V (SEQ ID NO: 16) | L234Y + K290Y + Y296W (SEQ ID NO: 18) | 5.94 | 6.80 |
| W117 | A330M + K334V (SEQ ID NO: 37) | L234Y + Y296W (SEQ ID NO: 39) | 28.92 | 40.04 |
| W125 | A330M + K334V (SEQ ID NO: 37) | K290Y + Y296W (SEQ ID NO: 41) | 59.32 | 76.92 |
| W141 | A330M + K334V (SEQ ID NO: 20) | L234Y + K290Y + Y296W (SEQ ID NO: 18) | 4.30 | 7.02 |
| W144 | A330F + K334V (SEQ ID NO: 22) | L234Y + K290Y + Y296W (SEQ ID NO: 18) | 4.44 | 6.77 |
| W157 | Q311M + A330M + K334V (SEQ ID NO: 24) | L234Y + E294L + Y296W (SEQ ID NO: 10) | 6.76 | 9.10 |

TABLE 4-continued

FcγRIIIA binding of human IgG1 antibodies containing Fc variants

| Alias | Negative/negative chain (K392D, K409D) | Positive/positive chain (E356K, D399K) | FcγRIIIA (158F) EC$_{50}$ (nM) | FcγRIIIA (158V) EC$_{50}$ (nM) |
|---|---|---|---|---|
| W160 | Q311M + A330F + K334V (SEQ ID NO: 26) | L234Y + E294L + Y296W (SEQ ID NO: 10) | 7.04 | 8.42 |
| W165 | S298T + A330M + K334V (SEQ ID NO: 28) | L234Y + K290Y + Y296W (SEQ ID NO: 18) | 5.24 | 7.56 |
| W168 | S298T + A330F + K334V (SEQ ID NO: 30) | L234Y + K290Y + Y296W (SEQ ID NO: 18) | 5.54 | 8.41 |
| W187 | S239D + A330M + K334V (SEQ ID NO: 32) | L234Y + K290Y + Y296W (SEQ ID NO: 18) | 2.25 | 4.69 |
| W189 | S239D + S298T + K334V (SEQ ID NO: 34) | L234Y + K290Y + Y296W (SEQ ID NO: 18) | 4.14 | 5.41 |

Binding of some of the Fc variants to recombinant human and murine FcγRs was tested using Biacore™ technology by capturing His-tagged FcγRs using a murine anti-His antibody attached to a Sensor Chip CM5 (Biacore). In separate experiments, FcγRIIA with a histidine at position 131, FcγRIIIA with a valine at position 158, and FcγRIIIA with a phenylalanine at position 158 were tested. Human IgG1 antibodies containing variant Fc regions were injected over the surface of the Sensor Chip CM5 to which the Fcγ receptor was tethered and allowed to associate and disassociate from the Fcγ receptor for defined times. These data were used to determine the binding constants, that is, $k_{on}$ (1/Ms), $k_{off}$ (1/s) and $K_D$ (nM), which were calculated from global fittings using the 1:1 kinetics binding model on BIAevaluation™ software. Generally, the antibodies containing altered Fc regions had $K_D$ values at low double digit nM to both FcγRIIIA 158F and 158V alleles.

TABLE 5

Kinetic and Equilibrium Binding Data

| Alias | −/− chain (K392D, K409D) | +/+ chain (E356K, D399K) | FcγRIIA (131H) $K_D$ (nM) | FcγRIIA (131R) $K_D$ (nM) | FcγRIIB $K_D$ (nM) | FcγRIIIA (158V) $k_{on}$ (1/Ms) | $k_{off}$ (1/s) | $K_D$ (nM) | FcγRIIIA (158F) $k_{on}$[#] (1/Ms) | $k_{off}$[#] (1/s) | $K_D$ (nM) |
|---|---|---|---|---|---|---|---|---|---|---|---|
| M01 | wild type | wild type | >1000 | >1000 | >1000 | ND* | ND | >500 | ND | ND | >1000 |
| M04 | charge pair substitutions only | charge pair substitutions only | >1000 | >1000 | >1000 | ND | ND | >500 | ND | ND | >1000 |
| M70 | L235S + S239D + K334V | L234Y + K290Y + Y296W | >1000 | >1000 | >1000 | 2.0 × 10$^5$ | 4.0 × 10$^{-3}$ | 20 | 1.7 × 10$^5$ | 6.8 × 10$^{-3}$ | 40 |
| M75 | Q311 + K334V | L234Y + F243V + Y296W | >500 | >1000 | >1000 | 1.5 × 10$^5$ | 3.8 × 10$^{-3}$ | 25 | 1.3 × 10$^5$ | 7.6 × 10$^{-3}$ | 60 |
| M77 | Q311M + K334V | L234Y + E294L + Y296W | >500 | >1000 | >1000 | 1.8 × 10$^5$ | 4.5 × 10$^{-3}$ | 26 | 1.3 × 10$^5$ | 7.9 × 10$^{-3}$ | 62 |
| M81 | S239D + K334V | L234Y + Y296W + S298C | >500 | >1000 | >500 | 2.7 × 10$^5$ | 3.1 × 10$^{-3}$ | 11 | 2.1 × 10$^5$ | 4.1 × 10$^{-3}$ | 19 |
| M85 | E294L + K334V | L234Y + K290Y + Y296W | >500 | >1000 | >1000 | 1.6 × 10$^5$ | 5.1 × 10$^{-3}$ | 32 | 1.1 × 10$^5$ | 7.9 × 10$^{-3}$ | 76 |
| M86 | E294L + K334V | L234Y + Y296 + S298C | 320 | >500 | >1000 | 2.2 × 10$^5$ | 4.3 × 10$^{-3}$ | 20 | 1.7 × 10$^5$ | 5.0 × 10$^{-3}$ | 32 |

*"ND" means not determined

[#]All of these rates were independently determined twice except those for M75, which was determined only once. The values shown for all other samples are the average of the two measurements.

These data indicate that introduction of the charge pair substitutions made no detectable difference in the equilibrium dissociation constant ($K_D$) for binding to any of the FcγRs tested. Compare row M01 to row M04. Further, the various asymmetric Fc alterations tested drastically reduced (more than ten-fold in all cases) the $K_D$ for binding to both allelic variants of FcγRIIIA, but had little or no effect on the $K_D$ for binding to FcγRIIA or FcγRIIB. Thus, the substitutions in the Fc regions of the variant IgG1 antibodies listed in Table 5 dramatically increased the avidity of binding of these Fc regions to FcγRIIIA.

Example 3: Competition Assays of Additional Fc Variants

Figure 10:
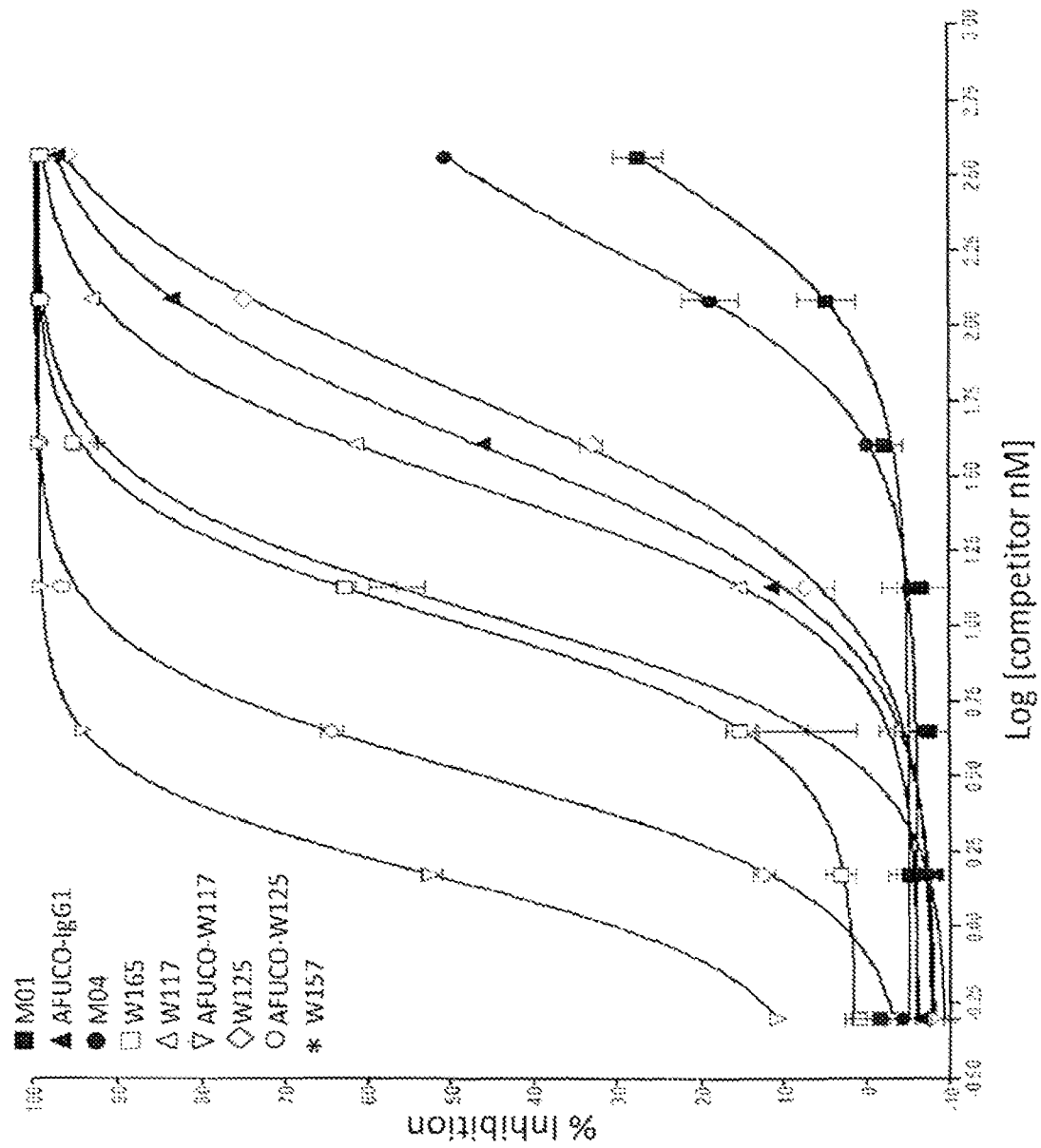
FIG. 10: Percent inhibition of AlphaLISA® signal for binding to human FcγR IIIA (158F) allelic variant by full length IgG1 antibodies containing variant Fc regions. The graph shows the percent inhibition of an AlphaLISA® signal as a function of the log of the competitor concentration. The various competitors, which are human IgG1 antibodies, are indicated by alias in the graph, and the substitutions contained in each competitor are indicated in Tables 3 and 4. The designation "AFUCO" preceding an alias means that the antibody lacks fucose.

To determine the relative binding affinity to the 158V and 158L allelic variants of FcγRIIIA of a number of additional Fc variants, AlphaLISA assays were performed essentially as described above in Example 1. The full length human anti-anti-Protein X IgG1 antibodies assayed were purified from transfected HEK 293 cells supernatants. In some cases the antibody preparations lacked fucose. Results are shown in FIGS. 10 (for the FcγRIIIA 158F allelic variant) and 11 (for the FcγRIIIA 158V allelic variant).

These data indicate that all tested antibodies comprising Fc variants competed with biotinylated IgG1 for binding to FcγRIIIA more effectively than an antibody comprising a wild type Fc. For example, FIG. 10 shows that a human wild type IgG1 Fc (M01) inhibits IgG1 binding to FcγRIIIA (158F) by only about 25% at the highest concentration tested (360 nM). M04, an IgG1 antibody that contains heterodimerizing alterations (K392D+K409D in one Fc polypeptide chain and E356K+D399K in other), was only slightly more effective than M01. As compared to M01 and M04, W117, W125, and an afucosylated wild type human IgG1 competed much more strongly, as evidenced by a shift to the left in the curves. See W117, W125, and AFUCO-M01 in FIG. 10. Afucosylated preparations of W117 and W125 (AFUCO-W117 and AFUCO-W125) showed a very high affinity for the human FcγRIIIA 158F, since these two preparations produced the leftmost curves in FIG. 10. Fc variants W157 and W165 also exhibited strong competition.

Figure 11:
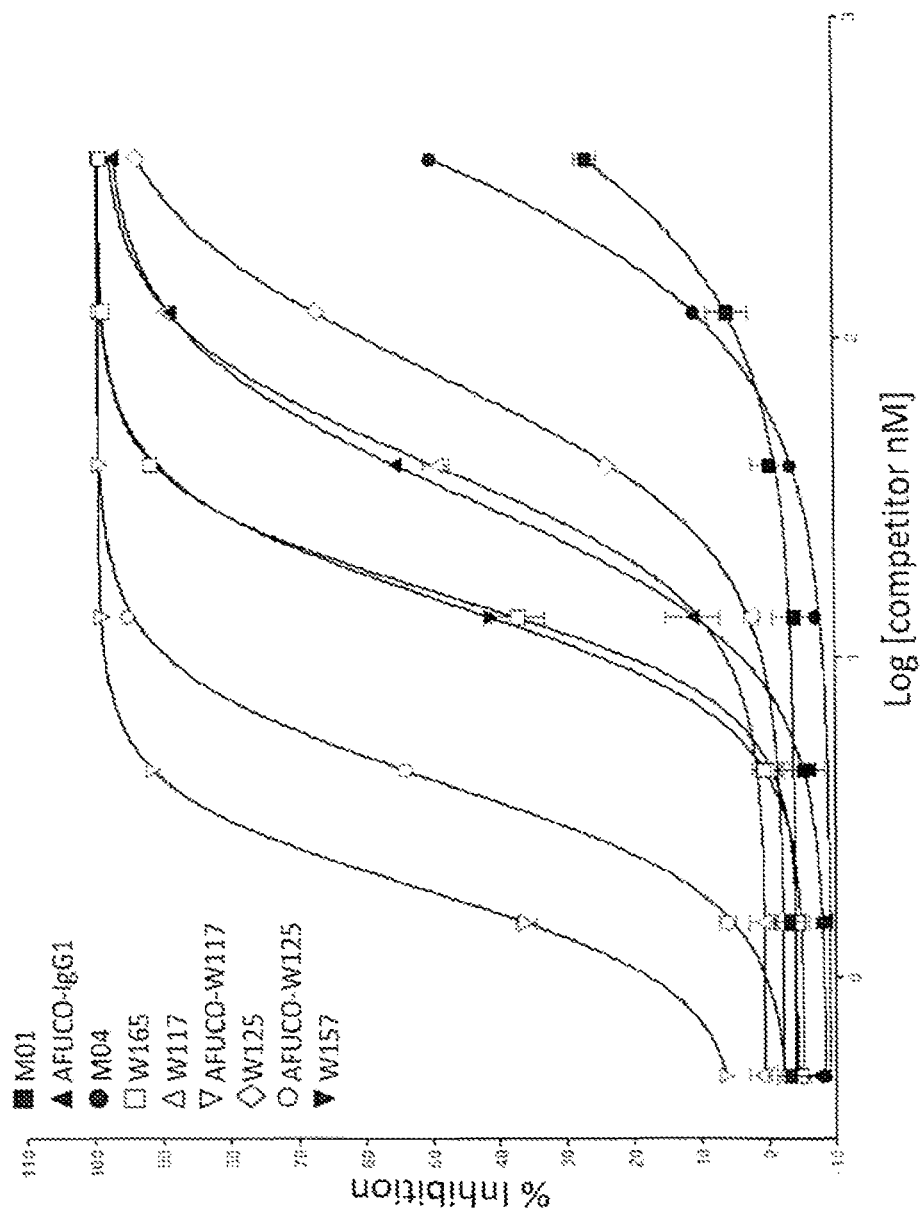
FIG. 11: Percent inhibition of AlphaLISA® signal for binding to human FcγR IIIA (158V) allelic variant by full length IgG1 antibodies containing variant Fc regions. The graph shows the percent inhibition of an AlphaLISA® signal as a function of the log of the competitor concentration. The various competitors, which are human IgG1 antibodies, are indicated by alias in the graph, and the substitutions contained in each competitor are indicated in Tables 3 and 4. The designation "AFUCO" preceding an alias means that the antibody lacks fucose.

Similar results for binding to FcγRIIIA (158V) are shown in FIG. 11. M01 and M04 exhibited weak competition for binding to FcγRIIIA (158V). As in FIG. 10, AFUCO-W117 and AFUCO-W125 were the most effective competitors, followed by W157 and W165. W117 and AFUCO-IgG1, followed by W125, were less effective, but still far more effective than M01 and M04. These data show that a synergistic enhancement of binding to FcγRIIIA can be achieved using defucosylated preparations of IgG1 heterodimeric variants.

Example 4: ADCC Assay of Antibodies Containing Variant Fc Regions

Figure 12:
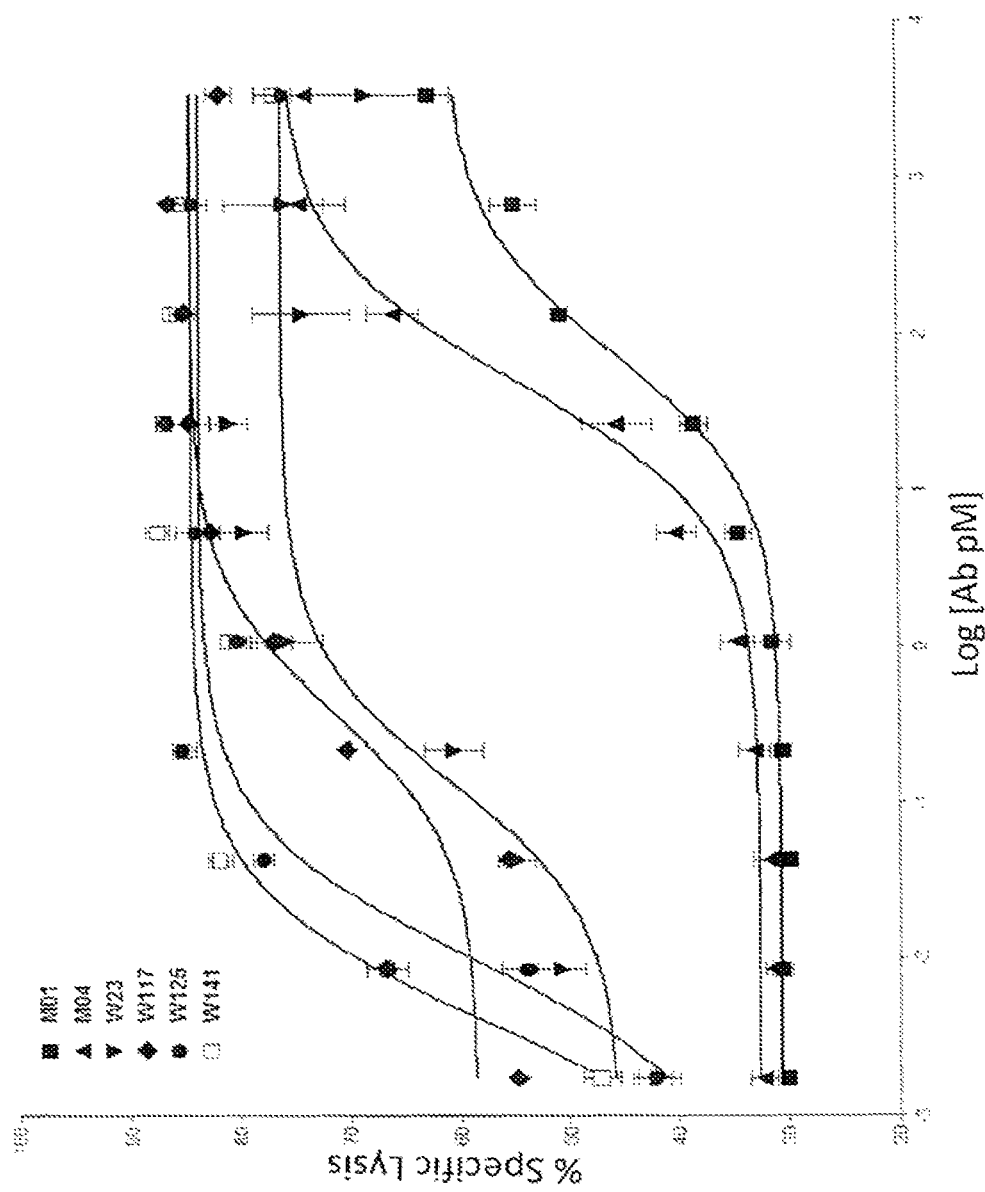
FIG. 12: Percent cell lysis of cells expressing high levels of antigen by full length IgG1 antibodies containing variant Fc regions. The graph shows the percentage of cells killed in an assay for antibody-dependent cellular cytotoxicity (% Specific Lysis) versus the log of the antibody concentration (pM). The various human IgG1 antibodies used in these assays are indicated by alias in the graph, and the substitutions contained in each competitor are indicated in Tables 3 and 4.
Figure 13:
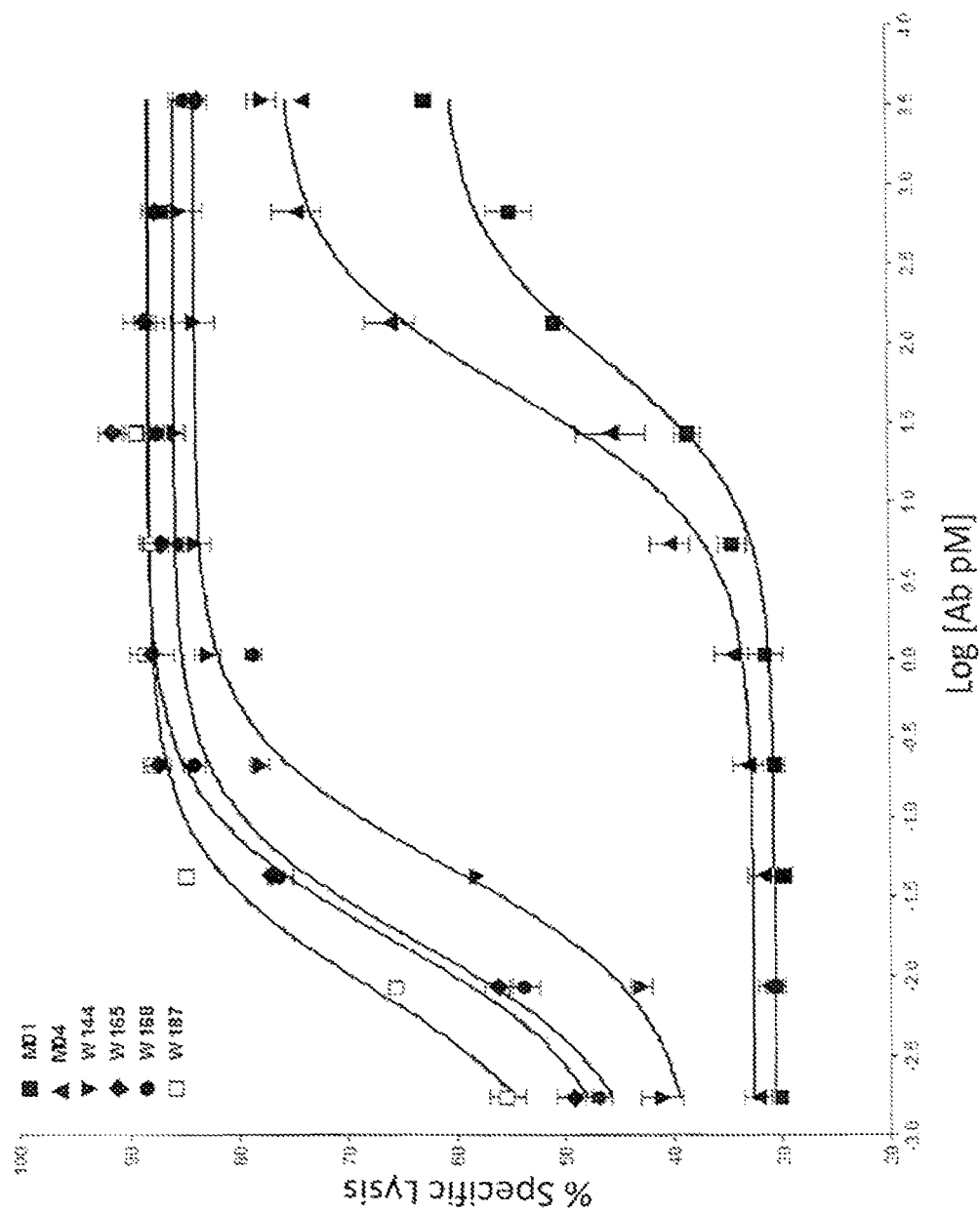
FIG. 13: Percent cell lysis of cells expressing moderate levels of antigen by full length IgG1 antibodies containing variant Fc regions. The graph shows the percentage of cells killed in an assay for antibody-dependent cellular cytotoxicity (% Specific Lysis) versus the log of the antibody concentration (pM). The various human IgG1 antibodies used in these assays are indicated by alias in the graph, and the substitutions contained in each competitor are indicated in Tables 3 and 4.

To determine ADCC activity of full length human anti-Protein X antibodies containing additional variant Fc regions, cell based ADCC assays were carried out using two different cell lines mentioned above as target cells, one expressing high levels of Protein X (SKBR3) and the other expressing moderate levels of Protein X (JIMT1). Assays were performed as described in Example 2. FIGS. 12 and 13 show the results obtained using SKBR3 cells.

Control antibodies M01 (having a wild type Fc region) and M04 (having an Fc region containing only heterodimerizing alterations) exhibited about 60% and 75% killing at the highest concentration of antibody tested (2,667 pM). Cell killing dropped off steeply at lower antibody concentrations of M01 and M04. However, antibodies containing variant Fc regions, including W23, W117, W125, W141, W144, W165, W168, and W187, exhibited higher levels of cell killing than either M01 or M04 at most antibody concentrations. Variant W187 exhibited the highest activity in this assay, correlating with the fact that it also exhibited the highest affinity to human FcγRIIIA. Table 4. Variants W117, W125, W165, and W168 also elicited potent ADCC activity in this assay.

Figure 14:
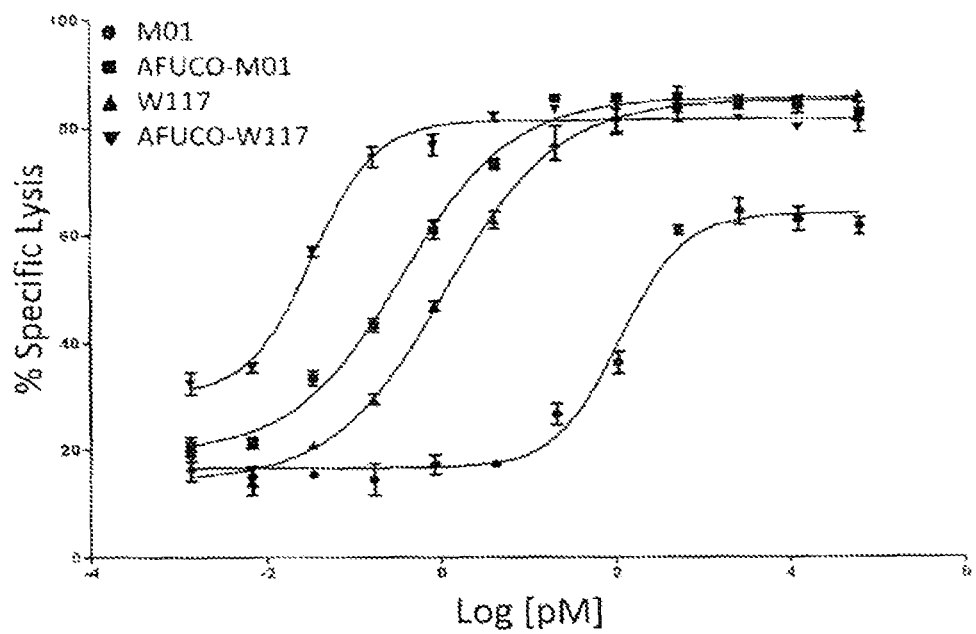
FIG. 14: Comparisons of ADCC activity of fucosylated and defucosylated preparations of IgG1 antibodies containing a wild type or a variant Fc region. The graphs show the percentage of cells killed in an assay for antibody-dependent cellular cytotoxicity (% Specific Lysis) versus the log of the antibody concentration [pM]. In the top panel, a cell line that expresses high levels of the antigen that the antibody binds to was used as a target cell (SKBR3). In the bottom panel, a cell line that expresses moderate levels of the antigen was used as a target cell (JIMT1). The various human IgG1 antibodies used in these assays are indicated in the graph as follows: "M01" indicates an IgG1 antibody containing a wild type Fc region that binds to the antigen; "AFUCO-M01" indicates a preparation of the same IgG1 antibody that contains no fucose; "W117" indicates an IgG1 antibody that binds to the antigen and contains a W117 variant Fc region; "AFUCO-W117" indicates a preparation of W117 that contains no fucose; "W125" indicates an IgG1 antibody that binds to the antigen and contains a W125 variant Fc region; and "AFUCO-W125" indicates a preparation of "W125" that contains no fucose.
Figure 14:
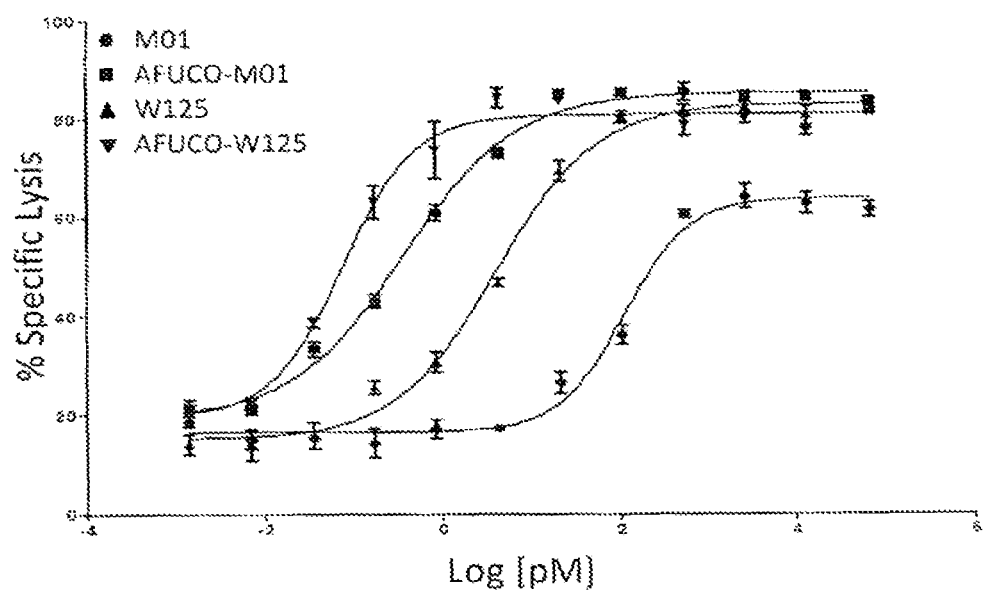

FIG. 14 shows the results (percent specific cell lysis) of an ADCC assay done using full length human IgG1 anti-Protein X antibodies and JIMT1 cells, which express moderate levels of Protein X. M01 antibodies (which contain a wild type Fc region) achieved only about 64 percent cell lysis at the highest antibody concentration tested, and the $EC_{50}$ of an M01 antibody in this assay was 98 pM. A defucosylated preparation of an M01 antibody achieved 86% specific cell lysis at the highest concentration tested and had an $EC_{50}$ of 0.274 pM in this assay. An antibody containing Fc variant W117 exhibited enhanced ADCC killing compared to M01 antibody, reaching a maximum specific lysis of about 85% and having an 85.5-fold lower of $EC_{50}$ (1.15 pM). A defucosylated preparation of the same antibody (AFUCO-W117) showed even higher killing activity and had a very low $EC_{50}$ (0.015 pM) in this assay. FIG. 14, top panel.

A similar increase in ADCC activity was observed in a defucosylated preparation of an antibody containing a W125 variant Fc region ($EC_{50}$ was 0.061 pM) as compared to a fucosylated preparation ($EC_{50}$ was 3.99 pM). FIG. 14, bottom panel. Since the defucoyslated versions of IgG1 antibodies containing either a W117 or a W125 Fc region both had much higher activity than the fucosylated versions of these antibodies, these data indicate a synergistic improvement in ADCC activity when the Fc region of an IgG1 antibody is defucosylated and also contains amino acid changes that increase its affinity to FcγRIIIA.

Example 5: Binding Constants of Antibodies Containing Additional Variant Fc Regions On and off rates for binding of a number of human IgG1 antibodies having additional variant Fc regions to the 158V and 158F allelic variants of human FcγRIIIA and to murine FcγRIV were determined using Biacore™ technology as described in Example 2. Briefly, the FcγRs, which were tagged with poly histidine, were captured on a CM5 Sensor Chip (Biacore™). The human IgG1 antibodies were injected over the surface of the CM5 chip to which the FcγRs were tethered and allowed to associate and dissociate from the Fcγs for defined times. The resulting data were used to determine the binding constants reported in Table 6 from BIAevaluation™ software. These data are shown in Table 6 below.

TABLE 6

On and Off Rates of Human IgG1 antibodies Containing Variant Fc Regions

| | Kinetic Affinity | | | | | | | | |
|---|---|---|---|---|---|---|---|---|---|
| | huFcγRIIIa-158V | | | huFcγRIIIa-158F | | | muFcγR IV | | |
| Sample | kon (1/Ms) | kd (1/s) | $K_D$ (nM) | kon (1/Ms) | kd (1/s) | $K_D$ (nM) | kon (1/Ms) | kd (1/s) | $K_D$ (nM) |
| huIgG1 (W23 Fc) | $1.6 \times 10^5$ | $4.8 \times 10^{-3}$ | 30 | $1.3 \times 10^5$ | $7.7 \times 10^{-3}$ | 61 | $1.8 \times 10^5$ | $1.4 \times 10^{-2}$ | 75 |
| huIgG1 (W141 Fc) | $1.4 \times 10^5$ | $4.8 \times 10^{-3}$ | 34 | $1.1 \times 10^5$ | $6.4 \times 10^{-3}$ | 59 | $1.6 \times 10^5$ | $1.2 \times 10^{-2}$ | 72 |
| huIgG1 (W144 Fc) | $1.5 \times 10^5$ | $4.6 \times 10^{-3}$ | 32 | $1.0 \times 10^5$ | $6.3 \times 10^{-3}$ | 62 | $1.0 \times 10^5$ | $1.3 \times 10^{-2}$ | 128 |
| huIgG1 (W157 Fc) | $1.2 \times 10^5$ | $4.3 \times 10^{-3}$ | 35 | $9.8 \times 10^4$ | $5.5 \times 10^{-3}$ | 56 | $1.1 \times 10^5$ | $8.4 \times 10^{-3}$ | 78 |
| huIgG1 (W165 Fc) | $1.6 \times 10^5$ | $4.8 \times 10^{-3}$ | 30 | $1.1 \times 10^5$ | $6.1 \times 10^{-3}$ | 54 | $1.7 \times 10^5$ | $1.2 \times 10^{-2}$ | 69 |
| huIgG1 (W168 Fc) | $1.7 \times 10^5$ | $4.5 \times 10^{-3}$ | 27 | $1.2 \times 10^5$ | $6.0 \times 10^{-3}$ | 48 | $1.2 \times 10^5$ | $1.1 \times 10^{-2}$ | 97 |
| huIgG1 (W187 Fc) | $2.9 \times 10^5$ | $4.8 \times 10^{-3}$ | 16 | $2.2 \times 10^5$ | $4.9 \times 10^{-3}$ | 22 | $2.9 \times 10^5$ | $8.0 \times 10^{-3}$ | 28 |
| huIgG1 (B50 Fc)* | $1.0 \times 10^5$ | $4.5 \times 10^{-3}$ | 44 | $8.2 \times 10^4$ | $6.4 \times 10^{-3}$ | 78 | $4.9 \times 10^4$ | $1.5 \times 10^{-2}$ | 301 |
| huIgG1 (W117 Fc) | $1.5 \times 10^5$ | $6.6 \times 10^{-3}$ | 43 | $1.1 \times 10^5$ | $1.1 \times 10^{-2}$ | 105 | $2.5 \times 10^5$ | $2.2 \times 10^{-2}$ | 90 |
| huIgG1 (W125 Fc) | $1.3 \times 10^5$ | $7.1 \times 10^{-3}$ | 57 | $5.5 \times 10^4$ | $7.9 \times 10^{-3}$ | 143 | $1.4 \times 10^5$ | $1.3 \times 10^{-2}$ | 89 |
| huIgG1 (afuco-W117 Fc) | $3.9 \times 10^5$ | $2.5 \times 10^{-3}$ | 6.4 | $3.5 \times 10^5$ | $3.2 \times 10^{-3}$ | 9.0 | $3.1 \times 10^5$ | $4.6 \times 10^{-3}$ | 15 |
| huIgG1 (afuco-W125 Fc) | $3.6 \times 10^5$ | $3.1 \times 10^{-3}$ | 8.8 | $3.0 \times 10^5$ | $4.4 \times 10^{-3}$ | 15 | $2.7 \times 10^5$ | $4.9 \times 10^{-3}$ | 18 |

*The B50 variant Fc region has the alterations K392D, K409D, L234I, A330M, and K334V in one Fc polypeptide and E356K, D399K, L234Y, K290Y, and Y296W in the other.

Antibodies containing variant Fc regions had $K_D$ values for binding to human FcγRIIIA, including the 158F and 158V allelic variants, ranging from 6.4 nM to 143 nM. These data, combined with the ADCC assay discussed above, show that increased cell killing in an ADCC assay by defucosylated preparations of antibodies containing a W125 or a W117 Fc region, as compared to fucosylated preparations, correlates with increased on rates and decreased off rates, i.e., a decreased $K_D$. Taken together with the data in Example 4, an approximately 10 fold decrease in $K_D$ for binding to human FcγRIIIA (158F) for defucosylated as compared to fucosylated W125 antibody (compare 15.0 nM to 143 nM) correlated with an approximately 50 fold decrease in $EC_{50}$ in the ADCC assay described in Example 4 (compare 0.061 pM to 3.99 pM). Similarly for a W117 antibody, a defucosylated preparation had a $K_D$ for binding to human FcγRIIIA (158F) about eleven fold lower than that of a fucosylated preparation (compare 9.0 nM to 105 nM) and had an $EC_{50}$ in the ADCC assay described in Example 4 that was about 100 fold lower (compare 0.015 pM to 1.15 pM). Thus, the increases in activity in the ADCC assay of the defucosylated versus fucosylated preparations of the W117 and W125 antibodies were synergistic since they exceeded expectations based on the increases in binding affinity to FcγRIIIA (158F). Similarly, the fact that the defucosylated preparations of W117 and W125 had much higher activity in the ADCC assay described in Example 4 than did fucosylated preparations of these antibodies or a defucoylated preparation of an antibody having a wild type Fc region (M01), was a further indication of synergistic activity.

What is claimed is:

1. An IgG1 Fc-containing protein comprising a heterodimeric human IgG1 Fc region and a binding region, wherein the IgG1 Fc region comprises an A chain and a B chain,
wherein the A chain and B chain comprise the following amino acid substitutions relative to a wild type human IgG1 Fc polypeptide chain, numbered according to the EU system:
(a) the A chain comprises Q311M and K334V substitutions and the B chain comprises L234Y, E294L, and Y296W substitutions or vice versa;
(b) the A chain comprises L235S, S239D, and K334V substitutions and the B chain comprises L234Y, K290Y, and Y296W substitutions or vice versa;
(c) the A chain comprises Q311M and K334V substitutions and the B chain comprises L234Y, F243V, and Y296W substitutions or vice versa;
(d) the A chain comprises S239D and K334V substitutions and the B chain comprises L234Y, Y296W, and S298C substitutions or vice versa;
(e) the A chain comprises E294L and K334V substitutions and the B chain comprises L234Y, K290Y, and Y296W substitutions or vice versa; and
(f) the A chain comprises E294L and K334V substitutions and the B chain comprises L234Y, Y296W, and S298C substitutions or vice versa;
wherein the IgG1 Fc-containing protein binds to human FcγRIIIA-158F and/or FcγRIIIA-158V with a $K_D$ of less than or equal to one fifth of the $K_D$ with which a second protein binds to human FcγRIIIA-158F and/or FcγRIIIA-158V, wherein the second protein is the same as the IgG1 Fc-containing protein except that it contains a wild type human IgG1 IgG Fc region without substitutions.

2. A pharmaceutical composition comprising a pharmaceutically acceptable carrier and a therapeutically effective amount of an IgG1 Fc-containing protein comprising a heterodimeric human IgG1 Fc region and a binding region, wherein the IgG1 Fc region comprises an A chain and a B chain, and
wherein the A chain and B chain comprise the following amino acid substitutions relative to a wild type human IgG1 Fc polypeptide chain, numbered according to the EU system:
(a) the A chain comprises Q311M and K334V substitutions and the B chain comprises L234Y, E294L, and Y296W substitutions or vice versa;
(b) the A chain comprises L235S, S239D, and K334V substitutions and the B chain comprises L234Y, K290Y, and Y296W substitutions or vice versa;
(c) the A chain comprises Q311M and K334V substitutions and the B chain comprises L234Y, F243V, and Y296W substitutions or vice versa;
(d) the A chain comprises S239D and K334V substitutions and the B chain comprises L234Y, Y296W, and S298C substitutions or vice versa;
(e) the A chain comprises E294L and K334V substitutions and the B chain comprises L234Y, K290Y, and Y296W substitutions or vice versa; and
(f) the A chain comprises E294L and K334V substitutions and the B chain comprises L234Y, Y296W, and S298C substitutions or vice versa;
wherein the IgG1 Fc-containing protein binds to human FcγRIIIA-158F and/or FcγRIIIA-158V with a $K_D$ of less than or equal to one fifth of the $K_D$ with which a second protein binds to human FcγRIIIA-158F and/or FcγRIIIA-158V, wherein the second protein is the same as the IgG1 Fc-containing protein except that it contains a wild type human IgG1 IgG Fc region without substitutions.

3. The IgG1 Fc-containing protein of claim 1, wherein the IgG1 Fc-containing protein binds to human FcγRIIIA-158F and/or FcγRIIIA-158V with a $K_D$ of less than or equal to one tenth of the $K_D$ with which the second protein binds to human FcγRIIIA-158F and/or FcγRIIIA-158V.

4. The IgG1 Fc-containing protein according to claim 1 or 3, wherein the A chain comprises the amino acid sequence of SEQ ID NO: 8; and the B chain comprises the amino acid sequence of SEQ ID NO: 10 or 18; or vice versa.

5. The IgG1 Fc-containing protein according to claim 1 or 3, wherein said IgG1 Fc-containing protein comprises the pair of amino acid sequences selected from the group consisting of: SEQ ID NO: 8 and SEQ ID NO:10; SEQ ID NO: 16 and SEQ ID NO:18; SEQ ID NO: 12 and SEQ ID NO:10; SEQ ID NO: 14 and SEQ ID NO:10; SEQ ID NO: 20 and SEQ ID NO:18; SEQ ID NO: 22 and SEQ ID NO:18; SEQ ID NO: 2[1]1 and SEQ ID NO:10; SEQ ID NO: 26 and SEQ ID NO:10; SEQ ID NO: 28 and SEQ ID NO:18; SEQ ID NO: 30 and SEQ ID NO:18; SEQ ID NO: 32 and SEQ ID NO:18; SEQ ID NO: 34 and SEQ ID NO:18; SEQ NO:37 and SEQ ID NO:39; and SEQ NO:37 and SEQ ID NO:[1]11.

6. The IgG1 Fc-containing protein according to claim 1 or 3, wherein the IgG1 Fc-containing protein is defucosylated.

7. The IgG1 Fc-containing protein according to claim 1 or 3, wherein the IgG1 Fc-containing protein is made in a CHO cell.

8. The IgG1 Fc-containing protein according to claim 1 or 3, wherein the IgG1 Fc-containing protein is an antibody.

9. The IgG1 Fc-containing protein of according to claim 1 or 3, wherein the IgG1 Fc-containing protein is an IgG1 Fc fusion protein.

10. The Fc-containing protein according to claim 1 or 3, wherein the IgG1 Fc-containing protein is a bispecific antibody and/or is a full length human IgG1 antibody.

* * * * *

SEQUENCE LISTING

```
<160> NUMBER OF SEQ ID NOS: 41

<210> SEQ ID NO 1
<211> LENGTH: 699
<212> TYPE: DNA
<213> ORGANISM: Homo sapiens
<220> FEATURE:
<221> NAME/KEY: CDS
<222> LOCATION: (1)..(699)

<400> SEQUENCE: 1 gag ccc aaa tct tgt gac aaa act cac aca tgc cca ccg tgc cca gca      48
Glu Pro Lys Ser Cys Asp Lys Thr His Thr Cys Pro Pro Cys Pro Ala
1               5                   10                  15 cct gaa ctc ctg ggg gga ccg tca gtc ttc ctc ttc ccc cca aaa ccc      96
Pro Glu Leu Leu Gly Gly Pro Ser Val Phe Leu Phe Pro Pro Lys Pro
            20                  25                  30 aag gac acc ctc atg atc tcc cgg acc cct gag gtc aca tgc gtg gtg     144
Lys Asp Thr Leu Met Ile Ser Arg Thr Pro Glu Val Thr Cys Val Val
        35                  40                  45 gtg gac gtg agc cac gaa gac cct gag gtc aag ttc aac tgg tac gtg     192
Val Asp Val Ser His Glu Asp Pro Glu Val Lys Phe Asn Trp Tyr Val
    50                  55                  60 gac ggc gtg gag gtg cat aat gcc aag aca aag ccg cgg gag gag cag     240
```

```
Asp Gly Val Glu Val His Asn Ala Lys Thr Lys Pro Arg Glu Glu Gln
65                  70                  75                  80 tac aac agc acg tac cgt gtg gtc agc gtc ctc acc gtc ctg cac cag    288
Tyr Asn Ser Thr Tyr Arg Val Val Ser Val Leu Thr Val Leu His Gln
                85                  90                  95 gac tgg ctg aat ggc aag gag tac aag tgc aag gtc tcc aac aaa gcc    336
Asp Trp Leu Asn Gly Lys Glu Tyr Lys Cys Lys Val Ser Asn Lys Ala
            100                 105                 110 ctc cca gcc ccc atc gag aaa acc atc tcc aaa gcc aaa ggg cag ccc    384
Leu Pro Ala Pro Ile Glu Lys Thr Ile Ser Lys Ala Lys Gly Gln Pro
        115                 120                 125 cga gaa cca cag gtg tac acc ctg ccc cca tcc cgg gag gag atg acc    432
Arg Glu Pro Gln Val Tyr Thr Leu Pro Pro Ser Arg Glu Glu Met Thr
    130                 135                 140 aag aac cag gtc agc ctg acc tgc ctg gtc aaa ggc ttc tat ccc agc    480
Lys Asn Gln Val Ser Leu Thr Cys Leu Val Lys Gly Phe Tyr Pro Ser
145                 150                 155                 160 gac atc gcc gtg gag tgg gag agc aat ggg cag ccg gag aac aac tac    528
Asp Ile Ala Val Glu Trp Glu Ser Asn Gly Gln Pro Glu Asn Asn Tyr
                165                 170                 175 aag acc acg cct ccc gtg ctg gac tcc gac ggc tcc ttc ttc ctc tat    576
Lys Thr Thr Pro Pro Val Leu Asp Ser Asp Gly Ser Phe Phe Leu Tyr
            180                 185                 190 agc aag ctc acc gtg gac aag agc agg tgg cag cag ggg aac gtc ttc    624
Ser Lys Leu Thr Val Asp Lys Ser Arg Trp Gln Gln Gly Asn Val Phe
        195                 200                 205 tca tgc tcc gtg atg cat gag gct ctg cac aac cac tac acg cag aag    672
Ser Cys Ser Val Met His Glu Ala Leu His Asn His Tyr Thr Gln Lys
    210                 215                 220 agc ctc tcc ctg tct ccg ggt aaa tga                                699
Ser Leu Ser Leu Ser Pro Gly Lys
225                 230

<210> SEQ ID NO 2
<211> LENGTH: 232
<212> TYPE: PRT
<213> ORGANISM: Homo sapiens

<400> SEQUENCE: 2

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Thr Cys Leu Val Lys Gly Phe Tyr Pro Ser
```

```
                145                 150                 155                 160
Asp Ile Ala Val Glu Trp Glu Ser Asn Gly Gln Pro Glu Asn Asn Tyr
                    165                 170                 175

Lys Thr Thr Pro Pro Val Leu Asp Ser Asp Gly Ser Phe Phe Leu Tyr
                    180                 185                 190

Ser Lys Leu Thr Val Asp Lys Ser Arg Trp Gln Gln Gly Asn Val Phe
                    195                 200                 205

Ser Cys Ser Val Met His Glu Ala Leu His Asn His Tyr Thr Gln Lys
            210                 215                 220

Ser Leu Ser Leu Ser Pro Gly Lys
225                 230

<210> SEQ ID NO 3
<211> LENGTH: 699
<212> TYPE: DNA
<213> ORGANISM: Homo sapiens
<220> FEATURE:
<221> NAME/KEY: CDS
<222> LOCATION: (1)..(699)
<220> FEATURE:
<221> NAME/KEY: mutation
<222> LOCATION: (529)..(529)
<220> FEATURE:
<221> NAME/KEY: mutation
<222> LOCATION: (531)..(531)
<220> FEATURE:
<221> NAME/KEY: mutation
<222> LOCATION: (580)..(580)
<220> FEATURE:
<221> NAME/KEY: mutation
<222> LOCATION: (582)..(582)
<223> OTHER INFORMATION: Nucleotide sequence encoding a human IgG1 Fc
      polypeptide chain containing the substitutions K392D and K409D

<400> SEQUENCE: 3 gag ccc aaa tct tgt gac aaa act cac aca tgc cca ccg tgc cca gca        48
Glu Pro Lys Ser Cys Asp Lys Thr His Thr Cys Pro Pro Cys Pro Ala
1               5                   10                  15 cct gaa ctc ctg ggg gga ccg tca gtc ttc ctc ttc ccc cca aaa ccc        96
Pro Glu Leu Leu Gly Gly Pro Ser Val Phe Leu Phe Pro Pro Lys Pro
                20                  25                  30 aag gac acc ctc atg atc tcc cgg acc cct gag gtc aca tgc gtg gtg       144
Lys Asp Thr Leu Met Ile Ser Arg Thr Pro Glu Val Thr Cys Val Val
            35                  40                  45 gtg gac gtg agc cac gaa gac cct gag gtc aag ttc aac tgg tac gtg       192
Val Asp Val Ser His Glu Asp Pro Glu Val Lys Phe Asn Trp Tyr Val
        50                  55                  60 gac ggc gtg gag gtg cat aat gcc aag aca aag ccg cgg gag gag cag       240
Asp Gly Val Glu Val His Asn Ala Lys Thr Lys Pro Arg Glu Glu Gln
65                  70                  75                  80 tac aac agc acg tac cgt gtg gtc agc gtc ctc acc gtc ctg cac cag       288
Tyr Asn Ser Thr Tyr Arg Val Val Ser Val Leu Thr Val Leu His Gln
                85                  90                  95 gac tgg ctg aat ggc aag gag tac aag tgc aag gtc tcc aac aaa gcc       336
Asp Trp Leu Asn Gly Lys Glu Tyr Lys Cys Lys Val Ser Asn Lys Ala
                100                 105                 110 ctc cca gcc ccc atc gag aaa acc atc tcc aaa gcc aaa ggg cag ccc       384
Leu Pro Ala Pro Ile Glu Lys Thr Ile Ser Lys Ala Lys Gly Gln Pro
            115                 120                 125 cga gaa cca cag gtg tac acc ctg ccc cca tcc cgg gag gag atg acc       432
Arg Glu Pro Gln Val Tyr Thr Leu Pro Pro Ser Arg Glu Glu Met Thr
        130                 135                 140 aag aac cag gtc agc ctg acc tgc ctg gtc aaa ggc ttc tat ccc agc       480
Lys Asn Gln Val Ser Leu Thr Cys Leu Val Lys Gly Phe Tyr Pro Ser
```

| | | | | | | | | | | | | | |
|---|---|---|---|---|---|---|---|---|---|---|---|---|---|
| Lys | Asn | Gln | Val | Ser | Leu | Thr | Cys | Leu | Val | Lys | Gly | Phe | Tyr | Pro | Ser |
| 145 | | | | 150 | | | | | 155 | | | | | 160 |

```
gac  atc  gcc  gtg  gag  tgg  gag  agc  aat  ggg  cag  ccg  gag  aac  aac  tac        528
Asp  Ile  Ala  Val  Glu  Trp  Glu  Ser  Asn  Gly  Gln  Pro  Glu  Asn  Asn  Tyr
               165                      170                      175 gac  acc  acg  cct  ccc  gtg  ctg  gac  tcc  gac  ggc  tcc  ttc  ttc  ctc  tat        576
Asp  Thr  Thr  Pro  Pro  Val  Leu  Asp  Ser  Asp  Gly  Ser  Phe  Phe  Leu  Tyr
               180                      185                      190 agc  gac  ctc  acc  gtg  gac  aag  agc  agg  tgg  cag  cag  ggg  aac  gtc  ttc        624
Ser  Asp  Leu  Thr  Val  Asp  Lys  Ser  Arg  Trp  Gln  Gln  Gly  Asn  Val  Phe
               195                      200                      205 tca  tgc  tcc  gtg  atg  cat  gag  gct  ctg  cac  aac  cac  tac  acg  cag  aag        672
Ser  Cys  Ser  Val  Met  His  Glu  Ala  Leu  His  Asn  His  Tyr  Thr  Gln  Lys
210                      215                      220 agc  ctc  tcc  ctg  tct  ccg  ggt  aaa  tga                                            699
Ser  Leu  Ser  Leu  Ser  Pro  Gly  Lys
225                      230

<210> SEQ ID NO 4
<211> LENGTH: 232
<212> TYPE: PRT
<213> ORGANISM: Homo sapiens

<400> SEQUENCE: 4

Glu  Pro  Lys  Ser  Cys  Asp  Lys  Thr  His  Thr  Cys  Pro  Pro  Cys  Pro  Ala
1                 5                       10                      15

Pro  Glu  Leu  Leu  Gly  Gly  Pro  Ser  Val  Phe  Leu  Phe  Pro  Pro  Lys  Pro
                  20                      25                      30

Lys  Asp  Thr  Leu  Met  Ile  Ser  Arg  Thr  Pro  Glu  Val  Thr  Cys  Val  Val
              35                      40                      45

Val  Asp  Val  Ser  His  Glu  Asp  Pro  Glu  Val  Lys  Phe  Asn  Trp  Tyr  Val
50                      55                      60

Asp  Gly  Val  Glu  Val  His  Asn  Ala  Lys  Thr  Lys  Pro  Arg  Glu  Glu  Gln
65                      70                      75                      80

Tyr  Asn  Ser  Thr  Tyr  Arg  Val  Val  Ser  Val  Leu  Thr  Val  Leu  His  Gln
                  85                      90                      95

Asp  Trp  Leu  Asn  Gly  Lys  Glu  Tyr  Lys  Cys  Lys  Val  Ser  Asn  Lys  Ala
              100                     105                     110

Leu  Pro  Ala  Pro  Ile  Glu  Lys  Thr  Ile  Ser  Lys  Ala  Lys  Gly  Gln  Pro
         115                     120                     125

Arg  Glu  Pro  Gln  Val  Tyr  Thr  Leu  Pro  Pro  Ser  Arg  Glu  Glu  Met  Thr
130                     135                     140

Lys  Asn  Gln  Val  Ser  Leu  Thr  Cys  Leu  Val  Lys  Gly  Phe  Tyr  Pro  Ser
145                     150                     155                     160

Asp  Ile  Ala  Val  Glu  Trp  Glu  Ser  Asn  Gly  Gln  Pro  Glu  Asn  Asn  Tyr
                  165                     170                     175

Asp  Thr  Thr  Pro  Pro  Val  Leu  Asp  Ser  Asp  Gly  Ser  Phe  Phe  Leu  Tyr
              180                     185                     190

Ser  Asp  Leu  Thr  Val  Asp  Lys  Ser  Arg  Trp  Gln  Gln  Gly  Asn  Val  Phe
         195                     200                     205

Ser  Cys  Ser  Val  Met  His  Glu  Ala  Leu  His  Asn  His  Tyr  Thr  Gln  Lys
210                     215                     220

Ser  Leu  Ser  Leu  Ser  Pro  Gly  Lys
225                     230

<210> SEQ ID NO 5
<211> LENGTH: 699
```

<212> TYPE: DNA
<213> ORGANISM: Homo sapiens
<220> FEATURE:
<221> NAME/KEY: CDS
<222> LOCATION: (1)..(699)
<220> FEATURE:
<221> NAME/KEY: mutation
<222> LOCATION: (421)..(421)
<220> FEATURE:
<221> NAME/KEY: mutation
<222> LOCATION: (550)..(550)
<220> FEATURE:
<221> NAME/KEY: mutation
<222> LOCATION: (552)..(552)
<223> OTHER INFORMATION: Nucleotide sequence encoding a human IgG1 Fc polypeptide chain containing the substitutions E356K and D399K

<400> SEQUENCE: 5

```
gag ccc aaa tct tgt gac aaa act cac aca tgc cca ccg tgc cca gca      48
Glu Pro Lys Ser Cys Asp Lys Thr His Thr Cys Pro Pro Cys Pro Ala
1               5                   10                  15 cct gaa ctc ctg ggg gga ccg tca gtc ttc ctc ttc ccc cca aaa ccc      96
Pro Glu Leu Leu Gly Gly Pro Ser Val Phe Leu Phe Pro Pro Lys Pro
            20                  25                  30 aag gac acc ctc atg atc tcc cgg acc cct gag gtc aca tgc gtg gtg     144
Lys Asp Thr Leu Met Ile Ser Arg Thr Pro Glu Val Thr Cys Val Val
        35                  40                  45 gtg gac gtg agc cac gaa gac cct gag gtc aag ttc aac tgg tac gtg     192
Val Asp Val Ser His Glu Asp Pro Glu Val Lys Phe Asn Trp Tyr Val
50                  55                  60 gac ggc gtg gag gtg cat aat gcc aag aca aag ccg cgg gag gag cag     240
Asp Gly Val Glu Val His Asn Ala Lys Thr Lys Pro Arg Glu Glu Gln
65                  70                  75                  80 tac aac agc acg tac cgt gtg gtc agc gtc ctc acc gtc ctg cac cag     288
Tyr Asn Ser Thr Tyr Arg Val Val Ser Val Leu Thr Val Leu His Gln
                85                  90                  95 gac tgg ctg aat ggc aag gag tac aag tgc aag gtc tcc aac aaa gcc     336
Asp Trp Leu Asn Gly Lys Glu Tyr Lys Cys Lys Val Ser Asn Lys Ala
            100                 105                 110 ctc cca gcc ccc atc gag aaa acc atc tcc aaa gcc aaa ggg cag ccc     384
Leu Pro Ala Pro Ile Glu Lys Thr Ile Ser Lys Ala Lys Gly Gln Pro
        115                 120                 125 cga gaa cca cag gtg tac acc ctg ccc cca tcc cgg aag gag atg acc     432
Arg Glu Pro Gln Val Tyr Thr Leu Pro Pro Ser Arg Lys Glu Met Thr
130                 135                 140 aag aac cag gtc agc ctg acc tgc ctg gtc aaa ggc ttc tat ccc agc     480
Lys Asn Gln Val Ser Leu Thr Cys Leu Val Lys Gly Phe Tyr Pro Ser
145                 150                 155                 160 gac atc gcc gtg gag tgg gag agc aat ggg cag ccg gag aac aac tac     528
Asp Ile Ala Val Glu Trp Glu Ser Asn Gly Gln Pro Glu Asn Asn Tyr
                165                 170                 175 aag acc acg cct ccc gtg ctg aag tcc gac ggc tcc ttc ttc ctc tat     576
Lys Thr Thr Pro Pro Val Leu Lys Ser Asp Gly Ser Phe Phe Leu Tyr
            180                 185                 190 agc aag ctc acc gtg gac aag agc agg tgg cag cag ggg aac gtc ttc     624
Ser Lys Leu Thr Val Asp Lys Ser Arg Trp Gln Gln Gly Asn Val Phe
        195                 200                 205 tca tgc tcc gtg atg cat gag gct ctg cac aac cac tac acg cag aag     672
Ser Cys Ser Val Met His Glu Ala Leu His Asn His Tyr Thr Gln Lys
210                 215                 220 agc ctc tcc ctg tct ccg ggt aaa tga                                 699
Ser Leu Ser Leu Ser Pro Gly Lys
225                 230
```

-continued

<210> SEQ ID NO 6
<211> LENGTH: 232
<212> TYPE: PRT
<213> ORGANISM: Homo sapiens

<400> SEQUENCE: 6

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Lys Glu Met Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Lys Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
210                 215                 220

Ser Leu Ser Leu Ser Pro Gly Lys
225                 230

<210> SEQ ID NO 7
<211> LENGTH: 699
<212> TYPE: DNA
<213> ORGANISM: Homo sapiens
<220> FEATURE:
<221> NAME/KEY: CDS
<222> LOCATION: (1)..(699)
<220> FEATURE:
<221> NAME/KEY: mutation
<222> LOCATION: (286)..(286)
<220> FEATURE:
<221> NAME/KEY: mutation
<222> LOCATION: (287)..(287)
<220> FEATURE:
<221> NAME/KEY: mutation
<222> LOCATION: (355)..(355)
<220> FEATURE:
<221> NAME/KEY: mutation
<222> LOCATION: (356)..(356)
<220> FEATURE:
<221> NAME/KEY: mutation
<222> LOCATION: (357)..(357)
<220> FEATURE:
<221> NAME/KEY: mutation
<222> LOCATION: (529)..(529)

<220> FEATURE:
<221> NAME/KEY: mutation
<222> LOCATION: (531)..(531)
<220> FEATURE:
<221> NAME/KEY: mutation
<222> LOCATION: (580)..(580)
<220> FEATURE:
<221> NAME/KEY: mutation
<222> LOCATION: (582)..(582)
<223> OTHER INFORMATION: Nucleotide sequence encoding a human IgG1 Fc polypeptide chain containing the substitutions K392D, K409D, Q311M, and K334V

<400> SEQUENCE: 7

```
gag ccc aaa tct tgt gac aaa act cac aca tgc cca ccg tgc cca gca      48
Glu Pro Lys Ser Cys Asp Lys Thr His Thr Cys Pro Pro Cys Pro Ala
1               5                   10                  15 cct gaa ctc ctg ggg gga ccg tca gtc ttc ctc ttc ccc cca aaa ccc      96
Pro Glu Leu Leu Gly Gly Pro Ser Val Phe Leu Phe Pro Pro Lys Pro
            20                  25                  30 aag gac acc ctc atg atc tcc cgg acc cct gag gtc aca tgc gtg gtg     144
Lys Asp Thr Leu Met Ile Ser Arg Thr Pro Glu Val Thr Cys Val Val
        35                  40                  45 gtg gac gtg agc cac gaa gac cct gag gtc aag ttc aac tgg tac gtg     192
Val Asp Val Ser His Glu Asp Pro Glu Val Lys Phe Asn Trp Tyr Val
50                  55                  60 gac ggc gtg gag gtg cat aat gcc aag aca aag ccg cgg gag gag cag     240
Asp Gly Val Glu Val His Asn Ala Lys Thr Lys Pro Arg Glu Glu Gln
65                  70                  75                  80 tac aac agc acg tac cgt gtg gtc agc gtc ctc acc gtc ctg cac atg     288
Tyr Asn Ser Thr Tyr Arg Val Val Ser Val Leu Thr Val Leu His Met
                85                  90                  95 gac tgg ctg aat ggc aag gag tac aag tgc aag gtc tcc aac aaa gcc     336
Asp Trp Leu Asn Gly Lys Glu Tyr Lys Cys Lys Val Ser Asn Lys Ala
            100                 105                 110 ctc cca gcc ccc atc gag gtg acc atc tcc aaa gcc aaa ggg cag ccc     384
Leu Pro Ala Pro Ile Glu Val Thr Ile Ser Lys Ala Lys Gly Gln Pro
        115                 120                 125 cga gaa cca cag gtg tac acc ctg ccc cca tcc cgg gag gag atg acc     432
Arg Glu Pro Gln Val Tyr Thr Leu Pro Pro Ser Arg Glu Glu Met Thr
130                 135                 140 aag aac cag gtc agc ctg acc tgc ctg gtc aaa ggc ttc tat ccc agc     480
Lys Asn Gln Val Ser Leu Thr Cys Leu Val Lys Gly Phe Tyr Pro Ser
145                 150                 155                 160 gac atc gcc gtg gag tgg gag agc aat ggg cag ccg gag aac aac tac     528
Asp Ile Ala Val Glu Trp Glu Ser Asn Gly Gln Pro Glu Asn Asn Tyr
                165                 170                 175 gac acc acg cct ccc gtg ctg gac tcc gac ggc tcc ttc ttc ctc tat     576
Asp Thr Thr Pro Pro Val Leu Asp Ser Asp Gly Ser Phe Phe Leu Tyr
            180                 185                 190 agc gac ctc acc gtg gac aag agc agg tgg cag cag ggg aac gtc ttc     624
Ser Asp Leu Thr Val Asp Lys Ser Arg Trp Gln Gln Gly Asn Val Phe
        195                 200                 205 tca tgc tcc gtg atg cat gag gct ctg cac aac cac tac acg cag aag     672
Ser Cys Ser Val Met His Glu Ala Leu His Asn His Tyr Thr Gln Lys
210                 215                 220 agc ctc tcc ctg tct ccg ggt aaa tga                                 699
Ser Leu Ser Leu Ser Pro Gly Lys
225                 230
```

<210> SEQ ID NO 8
<211> LENGTH: 232
<212> TYPE: PRT

<213> ORGANISM: Homo sapiens

<400> SEQUENCE: 8

```
Glu Pro Lys Ser Cys Asp Lys Thr His Thr Cys Pro Pro Cys Pro Ala
1               5                   10                  15
Pro Glu Leu Leu Gly Gly Pro Ser Val Phe Leu Phe Pro Pro Lys Pro
            20                  25                  30
Lys Asp Thr Leu Met Ile Ser Arg Thr Pro Glu Val Thr Cys Val Val
        35                  40                  45
Val Asp Val Ser His Glu Asp Pro Glu Val Lys Phe Asn Trp Tyr Val
    50                  55                  60
Asp Gly Val Glu Val His Asn Ala Lys Thr Lys Pro Arg Glu Glu Gln
65                  70                  75                  80
Tyr Asn Ser Thr Tyr Arg Val Val Ser Val Leu Thr Val Leu His Met
                85                  90                  95
Asp Trp Leu Asn Gly Lys Glu Tyr Lys Cys Lys Val Ser Asn Lys Ala
            100                 105                 110
Leu Pro Ala Pro Ile Glu Val Thr Ile Ser Lys Ala Lys Gly Gln Pro
        115                 120                 125
Arg Glu Pro Gln Val Tyr Thr Leu Pro Pro Ser Arg Glu Glu Met Thr
130                 135                 140
Lys Asn Gln Val Ser Leu Thr Cys Leu Val Lys Gly Phe Tyr Pro Ser
145                 150                 155                 160
Asp Ile Ala Val Glu Trp Glu Ser Asn Gly Gln Pro Glu Asn Asn Tyr
                165                 170                 175
Asp Thr Thr Pro Pro Val Leu Asp Ser Asp Gly Ser Phe Phe Leu Tyr
            180                 185                 190
Ser Asp Leu Thr Val Asp Lys Ser Arg Trp Gln Gln Gly Asn Val Phe
        195                 200                 205
Ser Cys Ser Val Met His Glu Ala Leu His Asn His Tyr Thr Gln Lys
210                 215                 220
Ser Leu Ser Leu Ser Pro Gly Lys
225                 230
```

<210> SEQ ID NO 9
<211> LENGTH: 699
<212> TYPE: DNA
<213> ORGANISM: Homo sapiens
<220> FEATURE:
<221> NAME/KEY: CDS
<222> LOCATION: (1)..(699)
<220> FEATURE:
<221> NAME/KEY: mutation
<222> LOCATION: (55)..(55)
<220> FEATURE:
<221> NAME/KEY: mutation
<222> LOCATION: (56)..(56)
<220> FEATURE:
<221> NAME/KEY: mutation
<222> LOCATION: (57)..(57)
<220> FEATURE:
<221> NAME/KEY: mutation
<222> LOCATION: (235)..(235)
<220> FEATURE:
<221> NAME/KEY: mutation
<222> LOCATION: (236)..(236)
<220> FEATURE:
<221> NAME/KEY: mutation
<222> LOCATION: (242)..(242)
<220> FEATURE:
<221> NAME/KEY: mutation
<222> LOCATION: (243)..(243)
<220> FEATURE:

<221> NAME/KEY: mutation
<222> LOCATION: (421)..(421)
<220> FEATURE:
<221> NAME/KEY: mutation
<222> LOCATION: (550)..(550)
<220> FEATURE:
<221> NAME/KEY: mutation
<222> LOCATION: (552)..(552)
<223> OTHER INFORMATION: Nucleotide sequence encoding a human IgG1 Fc
    polypeptide chain containing the substitutions E356K, D399K,
    L234Y, E294L, and Y296W

<400> SEQUENCE: 9

```
gag ccc aaa tct tgt gac aaa act cac aca tgc cca ccg tgc cca gca      48
Glu Pro Lys Ser Cys Asp Lys Thr His Thr Cys Pro Pro Cys Pro Ala
1               5                   10                  15 cct gaa tat ctg ggg gga ccg tca gtc ttc ctc ttc ccc cca aaa ccc      96
Pro Glu Tyr Leu Gly Gly Pro Ser Val Phe Leu Phe Pro Pro Lys Pro
            20                  25                  30 aag gac acc ctc atg atc tcc cgg acc cct gag gtc aca tgc gtg gtg     144
Lys Asp Thr Leu Met Ile Ser Arg Thr Pro Glu Val Thr Cys Val Val
        35                  40                  45 gtg gac gtg agc cac gaa gac cct gag gtc aag ttc aac tgg tac gtg     192
Val Asp Val Ser His Glu Asp Pro Glu Val Lys Phe Asn Trp Tyr Val
    50                  55                  60 gac ggc gtg gag gtg cat aat gcc aag aca aag ccg cgg gag ctg cag     240
Asp Gly Val Glu Val His Asn Ala Lys Thr Lys Pro Arg Glu Leu Gln
65                  70                  75                  80 tgg aac agc acg tac cgt gtg gtc agc gtc ctc acc gtc ctg cac cag     288
Trp Asn Ser Thr Tyr Arg Val Val Ser Val Leu Thr Val Leu His Gln
                85                  90                  95 gac tgg ctg aat ggc aag gag tac aag tgc aag gtc tcc aac aaa gcc     336
Asp Trp Leu Asn Gly Lys Glu Tyr Lys Cys Lys Val Ser Asn Lys Ala
            100                 105                 110 ctc cca gcc ccc atc gag aaa acc atc tcc aaa gcc aaa ggg cag ccc     384
Leu Pro Ala Pro Ile Glu Lys Thr Ile Ser Lys Ala Lys Gly Gln Pro
        115                 120                 125 cga gaa cca cag gtg tac acc ctg ccc cca tcc cgg aag gag atg acc     432
Arg Glu Pro Gln Val Tyr Thr Leu Pro Pro Ser Arg Lys Glu Met Thr
    130                 135                 140 aag aac cag gtc agc ctg acc tgc ctg gtc aaa ggc ttc tat ccc agc     480
Lys Asn Gln Val Ser Leu Thr Cys Leu Val Lys Gly Phe Tyr Pro Ser
145                 150                 155                 160 gac atc gcc gtg gag tgg gag agc aat ggg cag ccg gag aac aac tac     528
Asp Ile Ala Val Glu Trp Glu Ser Asn Gly Gln Pro Glu Asn Asn Tyr
                165                 170                 175 aag acc acg cct ccc gtg ctg aag tcc gac ggc tcc ttc ttc ctc tat     576
Lys Thr Thr Pro Pro Val Leu Lys Ser Asp Gly Ser Phe Phe Leu Tyr
            180                 185                 190 agc aag ctc acc gtg gac aag agc agg tgg cag cag ggg aac gtc ttc     624
Ser Lys Leu Thr Val Asp Lys Ser Arg Trp Gln Gln Gly Asn Val Phe
        195                 200                 205 tca tgc tcc gtg atg cat gag gct ctg cac aac cac tac acg cag aag     672
Ser Cys Ser Val Met His Glu Ala Leu His Asn His Tyr Thr Gln Lys
    210                 215                 220 agc ctc tcc ctg tct ccg ggt aaa tga                                  699
Ser Leu Ser Leu Ser Pro Gly Lys
225                 230
```

<210> SEQ ID NO 10
<211> LENGTH: 232
<212> TYPE: PRT
<213> ORGANISM: Homo sapiens -continued

<400> SEQUENCE: 10

Glu Pro Lys Ser Cys Asp Lys Thr His Thr Cys Pro Pro Cys Pro Ala
1               5                   10                  15

Pro Glu Tyr Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Leu Gln
65                  70                  75                  80

Trp Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Lys Glu Met Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 11
<211> LENGTH: 699
<212> TYPE: DNA
<213> ORGANISM: Homo sapiens
<220> FEATURE:
<221> NAME/KEY: CDS
<222> LOCATION: (1)..(699)
<220> FEATURE:
<221> NAME/KEY: mutation
<222> LOCATION: (52)..(52)
<220> FEATURE:
<221> NAME/KEY: mutation
<222> LOCATION: (53)..(53)
<220> FEATURE:
<221> NAME/KEY: mutation
<222> LOCATION: (54)..(54)
<220> FEATURE:
<221> NAME/KEY: mutation
<222> LOCATION: (286)..(286)
<220> FEATURE:
<221> NAME/KEY: mutation
<222> LOCATION: (287)..(287)
<220> FEATURE:
<221> NAME/KEY: mutation
<222> LOCATION: (355)..(355)
<220> FEATURE:
<221> NAME/KEY: mutation
<222> LOCATION: (356)..(356)
<220> FEATURE:
<221> NAME/KEY: mutation

```
<222> LOCATION: (357)..(357)
<220> FEATURE:
<221> NAME/KEY: mutation
<222> LOCATION: (529)..(529)
<220> FEATURE:
<221> NAME/KEY: mutation
<222> LOCATION: (531)..(531)
<220> FEATURE:
<221> NAME/KEY: mutation
<222> LOCATION: (580)..(580)
<220> FEATURE:
<221> NAME/KEY: mutation
<222> LOCATION: (582)..(582)
<223> OTHER INFORMATION: Nucleotide sequence encoding a human IgG1 Fc
      polypeptide chain containing the substitutions K392D, K409D,
      E233L, Q311M, and K334V

<400> SEQUENCE: 11 gag ccc aaa tct tgt gac aaa act cac aca tgc cca ccg tgc cca gca      48
Glu Pro Lys Ser Cys Asp Lys Thr His Thr Cys Pro Pro Cys Pro Ala
1               5                   10                  15 cct ctg ctc ctg ggg gga ccg tca gtc ttc ctc ttc ccc cca aaa ccc      96
Pro Leu Leu Leu Gly Gly Pro Ser Val Phe Leu Phe Pro Pro Lys Pro
            20                  25                  30 aag gac acc ctc atg atc tcc cgg acc cct gag gtc aca tgc gtg gtg     144
Lys Asp Thr Leu Met Ile Ser Arg Thr Pro Glu Val Thr Cys Val Val
        35                  40                  45 gtg gac gtg agc cac gaa gac cct gag gtc aag ttc aac tgg tac gtg     192
Val Asp Val Ser His Glu Asp Pro Glu Val Lys Phe Asn Trp Tyr Val
    50                  55                  60 gac ggc gtg gag gtg cat aat gcc aag aca aag ccg cgg gag gag cag     240
Asp Gly Val Glu Val His Asn Ala Lys Thr Lys Pro Arg Glu Glu Gln
65                  70                  75                  80 tac aac agc acg tac cgt gtg gtc agc gtc ctc acc gtc ctg cac atg     288
Tyr Asn Ser Thr Tyr Arg Val Val Ser Val Leu Thr Val Leu His Met
                85                  90                  95 gac tgg ctg aat ggc aag gag tac aag tgc aag gtc tcc aac aaa gcc     336
Asp Trp Leu Asn Gly Lys Glu Tyr Lys Cys Lys Val Ser Asn Lys Ala
            100                 105                 110 ctc cca gcc ccc atc gag gtg acc atc tcc aaa gcc aaa ggg cag ccc     384
Leu Pro Ala Pro Ile Glu Val Thr Ile Ser Lys Ala Lys Gly Gln Pro
        115                 120                 125 cga gaa cca cag gtg tac acc ctg ccc cca tcc cgg gag gag atg acc     432
Arg Glu Pro Gln Val Tyr Thr Leu Pro Pro Ser Arg Glu Glu Met Thr
130                 135                 140 aag aac cag gtc agc ctg acc tgc ctg gtc aaa ggc ttc tat ccc agc     480
Lys Asn Gln Val Ser Leu Thr Cys Leu Val Lys Gly Phe Tyr Pro Ser
145                 150                 155                 160 gac atc gcc gtg gag tgg gag agc aat ggg cag ccg gag aac aac tac     528
Asp Ile Ala Val Glu Trp Glu Ser Asn Gly Gln Pro Glu Asn Asn Tyr
                165                 170                 175 gac acc acg cct ccc gtg ctg gac tcc gac ggc tcc ttc ttc ctc tat     576
Asp Thr Thr Pro Pro Val Leu Asp Ser Asp Gly Ser Phe Phe Leu Tyr
            180                 185                 190 agc gac ctc acc gtg gac aag agc agg tgg cag cag ggg aac gtc ttc     624
Ser Asp Leu Thr Val Asp Lys Ser Arg Trp Gln Gln Gly Asn Val Phe
        195                 200                 205 tca tgc tcc gtg atg cat gag gct ctg cac aac cac tac acg cag aag     672
Ser Cys Ser Val Met His Glu Ala Leu His Asn His Tyr Thr Gln Lys
210                 215                 220 agc ctc tcc ctg tct ccg ggt aaa tga                                  699
Ser Leu Ser Leu Ser Pro Gly Lys
225                 230
```

<210> SEQ ID NO 12
<211> LENGTH: 232
<212> TYPE: PRT
<213> ORGANISM: Homo sapiens

<400> SEQUENCE: 12

Glu Pro Lys Ser Cys Asp Lys Thr His Thr Cys Pro Pro Cys Pro Ala
1               5                   10                  15

Pro Leu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Met
                85                  90                  95

Asp Trp Leu Asn Gly Lys Glu Tyr Lys Cys Lys Val Ser Asn Lys Ala
            100                 105                 110

Leu Pro Ala Pro Ile Glu Val Thr Ile Ser Lys Ala Lys Gly Gln Pro
        115                 120                 125

Arg Glu Pro Gln Val Tyr Thr Leu Pro Pro Ser Arg Glu Glu Met Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Asp Thr Thr Pro Pro Val Leu Asp Ser Asp Gly Ser Phe Phe Leu Tyr
            180                 185                 190

Ser Asp Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
210                 215                 220

Ser Leu Ser Leu Ser Pro Gly Lys
225                 230

<210> SEQ ID NO 13
<211> LENGTH: 699
<212> TYPE: DNA
<213> ORGANISM: Homo sapiens
<220> FEATURE:
<221> NAME/KEY: CDS
<222> LOCATION: (1)..(699)
<220> FEATURE:
<221> NAME/KEY: mutation
<222> LOCATION: (55)..(55)
<220> FEATURE:
<221> NAME/KEY: mutation
<222> LOCATION: (286)..(286)
<220> FEATURE:
<221> NAME/KEY: mutation
<222> LOCATION: (287)..(287)
<220> FEATURE:
<221> NAME/KEY: mutation
<222> LOCATION: (355)..(355)
<220> FEATURE:
<221> NAME/KEY: mutation
<222> LOCATION: (356)..(356)
<220> FEATURE:
<221> NAME/KEY: mutation
<222> LOCATION: (357)..(357)

```
<220> FEATURE:
<221> NAME/KEY: mutation
<222> LOCATION: (529)..(529)
<220> FEATURE:
<221> NAME/KEY: mutation
<222> LOCATION: (531)..(531)
<220> FEATURE:
<221> NAME/KEY: mutation
<222> LOCATION: (580)..(580)
<220> FEATURE:
<221> NAME/KEY: mutation
<222> LOCATION: (582)..(582)
<223> OTHER INFORMATION: Nucleotide sequence encoding a human IgG1 Fc
      polypeptide chain containing the substitutions K392D, K409D,
      L234I, Q311M, and K334V

<400> SEQUENCE: 13
```

| | | | | | | | | | | | | | | | | |
|---|---|---|---|---|---|---|---|---|---|---|---|---|---|---|---|---|
| gag | ccc | aaa | tct | tgt | gac | aaa | act | cac | aca | tgc | cca | ccg | tgc | cca | gca | 48 |
| Glu | Pro | Lys | Ser | Cys | Asp | Lys | Thr | His | Thr | Cys | Pro | Pro | Cys | Pro | Ala | |
| 1 | | | | 5 | | | | | 10 | | | | | 15 | | |
| cct | gaa | atc | ctg | ggg | gga | ccg | tca | gtc | ttc | ctc | ttc | ccc | cca | aaa | ccc | 96 |
| Pro | Glu | Ile | Leu | Gly | Gly | Pro | Ser | Val | Phe | Leu | Phe | Pro | Pro | Lys | Pro | |
| | | | 20 | | | | | 25 | | | | | 30 | | | |
| aag | gac | acc | ctc | atg | atc | tcc | cgg | acc | cct | gag | gtc | aca | tgc | gtg | gtg | 144 |
| Lys | Asp | Thr | Leu | Met | Ile | Ser | Arg | Thr | Pro | Glu | Val | Thr | Cys | Val | Val | |
| | | 35 | | | | | 40 | | | | | 45 | | | | |
| gtg | gac | gtg | agc | cac | gaa | gac | cct | gag | gtc | aag | ttc | aac | tgg | tac | gtg | 192 |
| Val | Asp | Val | Ser | His | Glu | Asp | Pro | Glu | Val | Lys | Phe | Asn | Trp | Tyr | Val | |
| 50 | | | | | 55 | | | | | 60 | | | | | | |
| gac | ggc | gtg | gag | gtg | cat | aat | gcc | aag | aca | aag | ccg | cgg | gag | gag | cag | 240 |
| Asp | Gly | Val | Glu | Val | His | Asn | Ala | Lys | Thr | Lys | Pro | Arg | Glu | Glu | Gln | |
| 65 | | | | 70 | | | | | 75 | | | | | 80 | | |
| tac | aac | agc | acg | tac | cgt | gtg | gtc | agc | gtc | ctc | acc | gtc | ctg | cac | atg | 288 |
| Tyr | Asn | Ser | Thr | Tyr | Arg | Val | Val | Ser | Val | Leu | Thr | Val | Leu | His | Met | |
| | | | 85 | | | | | 90 | | | | | 95 | | | |
| gac | tgg | ctg | aat | ggc | aag | gag | tac | aag | tgc | aag | gtc | tcc | aac | aaa | gcc | 336 |
| Asp | Trp | Leu | Asn | Gly | Lys | Glu | Tyr | Lys | Cys | Lys | Val | Ser | Asn | Lys | Ala | |
| | | | 100 | | | | | 105 | | | | | 110 | | | |
| ctc | cca | gcc | ccc | atc | gag | gtg | acc | atc | tcc | aaa | gcc | aaa | ggg | cag | ccc | 384 |
| Leu | Pro | Ala | Pro | Ile | Glu | Val | Thr | Ile | Ser | Lys | Ala | Lys | Gly | Gln | Pro | |
| | | 115 | | | | | 120 | | | | | 125 | | | | |
| cga | gaa | cca | cag | gtg | tac | acc | ctg | ccc | cca | tcc | cgg | gag | gag | atg | acc | 432 |
| Arg | Glu | Pro | Gln | Val | Tyr | Thr | Leu | Pro | Pro | Ser | Arg | Glu | Glu | Met | Thr | |
| | 130 | | | | | 135 | | | | | 140 | | | | | |
| aag | aac | cag | gtc | agc | ctg | acc | tgc | ctg | gtc | aaa | ggc | ttc | tat | ccc | agc | 480 |
| Lys | Asn | Gln | Val | Ser | Leu | Thr | Cys | Leu | Val | Lys | Gly | Phe | Tyr | Pro | Ser | |
| 145 | | | | | 150 | | | | | 155 | | | | | 160 | |
| gac | atc | gcc | gtg | gag | tgg | gag | agc | aat | ggg | cag | ccg | gag | aac | aac | tac | 528 |
| Asp | Ile | Ala | Val | Glu | Trp | Glu | Ser | Asn | Gly | Gln | Pro | Glu | Asn | Asn | Tyr | |
| | | | 165 | | | | | 170 | | | | | 175 | | | |
| gac | acc | acg | cct | ccc | gtg | ctg | gac | tcc | gac | ggc | tcc | ttc | ttc | ctc | tat | 576 |
| Asp | Thr | Thr | Pro | Pro | Val | Leu | Asp | Ser | Asp | Gly | Ser | Phe | Phe | Leu | Tyr | |
| | | | 180 | | | | | 185 | | | | | 190 | | | |
| agc | gac | ctc | acc | gtg | gac | aag | agc | agg | tgg | cag | cag | ggg | aac | gtc | ttc | 624 |
| Ser | Asp | Leu | Thr | Val | Asp | Lys | Ser | Arg | Trp | Gln | Gln | Gly | Asn | Val | Phe | |
| | | 195 | | | | | 200 | | | | | 205 | | | | |
| tca | tgc | tcc | gtg | atg | cat | gag | gct | ctg | cac | aac | cac | tac | acg | cag | aag | 672 |
| Ser | Cys | Ser | Val | Met | His | Glu | Ala | Leu | His | Asn | His | Tyr | Thr | Gln | Lys | |
| | 210 | | | | | 215 | | | | | 220 | | | | | |
| agc | ctc | tcc | ctg | tct | ccg | ggt | aaa | tga | | | | | | | | 699 |
| Ser | Leu | Ser | Leu | Ser | Pro | Gly | Lys | | | | | | | | | |
| 225 | | | | 230 | | | | | | | | | | | | |

```
<210> SEQ ID NO 14
<211> LENGTH: 232
<212> TYPE: PRT
<213> ORGANISM: Homo sapiens

<400> SEQUENCE: 14

Glu Pro Lys Ser Cys Asp Lys Thr His Thr Cys Pro Pro Cys Pro Ala
1               5                   10                  15

Pro Glu Ile Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Met
                85                  90                  95

Asp Trp Leu Asn Gly Lys Glu Tyr Lys Cys Lys Val Ser Asn Lys Ala
            100                 105                 110

Leu Pro Ala Pro Ile Glu Val Thr Ile Ser Lys Ala Lys Gly Gln Pro
        115                 120                 125

Arg Glu Pro Gln Val Tyr Thr Leu Pro Pro Ser Arg Glu Glu Met Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Asp Thr Thr Pro Pro Val Leu Asp Ser Asp Gly Ser Phe Phe Leu Tyr
            180                 185                 190

Ser Asp Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
210                 215                 220

Ser Leu Ser Leu Ser Pro Gly Lys
225                 230

<210> SEQ ID NO 15
<211> LENGTH: 699
<212> TYPE: DNA
<213> ORGANISM: Homo sapiens
<220> FEATURE:
<221> NAME/KEY: CDS
<222> LOCATION: (1)..(699)
<220> FEATURE:
<221> NAME/KEY: mutation
<222> LOCATION: (248)..(248)
<220> FEATURE:
<221> NAME/KEY: mutation
<222> LOCATION: (355)..(355)
<220> FEATURE:
<221> NAME/KEY: mutation
<222> LOCATION: (356)..(356)
<220> FEATURE:
<221> NAME/KEY: mutation
<222> LOCATION: (357)..(357)
<220> FEATURE:
<221> NAME/KEY: mutation
<222> LOCATION: (529)..(529)
<220> FEATURE:
<221> NAME/KEY: mutation
<222> LOCATION: (531)..(531)
<220> FEATURE:
```

```
<221> NAME/KEY: mutation
<222> LOCATION: (580)..(580)
<220> FEATURE:
<221> NAME/KEY: mutation
<222> LOCATION: (582)..(582)
<223> OTHER INFORMATION: Nucleotide sequence encoding a human IgG1 Fc
      polypeptide chain containing the substitutions K392D, K409D,
      S298T, and K334V

<400> SEQUENCE: 15
```

| | | | | | | | | | | | | | | | | |
|---|---|---|---|---|---|---|---|---|---|---|---|---|---|---|---|---|
| gag | ccc | aaa | tct | tgt | gac | aaa | act | cac | aca | tgc | cca | ccg | tgc | cca | gca | 48 |
| Glu | Pro | Lys | Ser | Cys | Asp | Lys | Thr | His | Thr | Cys | Pro | Pro | Cys | Pro | Ala | |
| 1 | | | | 5 | | | | | 10 | | | | | 15 | | |
| cct | gaa | ctc | ctg | ggg | gga | ccg | tca | gtc | ttc | ctc | ttc | ccc | cca | aaa | ccc | 96 |
| Pro | Glu | Leu | Leu | Gly | Gly | Pro | Ser | Val | Phe | Leu | Phe | Pro | Pro | Lys | Pro | |
| | | | 20 | | | | | 25 | | | | | 30 | | | |
| aag | gac | acc | ctc | atg | atc | tcc | cgg | acc | cct | gag | gtc | aca | tgc | gtg | gtg | 144 |
| Lys | Asp | Thr | Leu | Met | Ile | Ser | Arg | Thr | Pro | Glu | Val | Thr | Cys | Val | Val | |
| | | 35 | | | | | 40 | | | | | 45 | | | | |
| gtg | gac | gtg | agc | cac | gaa | gac | cct | gag | gtc | aag | ttc | aac | tgg | tac | gtg | 192 |
| Val | Asp | Val | Ser | His | Glu | Asp | Pro | Glu | Val | Lys | Phe | Asn | Trp | Tyr | Val | |
| 50 | | | | | 55 | | | | | 60 | | | | | | |
| gac | ggc | gtg | gag | gtg | cat | aat | gcc | aag | aca | aag | ccg | cgg | gag | gag | cag | 240 |
| Asp | Gly | Val | Glu | Val | His | Asn | Ala | Lys | Thr | Lys | Pro | Arg | Glu | Glu | Gln | |
| 65 | | | | 70 | | | | | 75 | | | | | 80 | | |
| tac | aac | acc | acg | tac | cgt | gtg | gtc | agc | gtc | ctc | acc | gtc | ctg | cac | cag | 288 |
| Tyr | Asn | Thr | Thr | Tyr | Arg | Val | Val | Ser | Val | Leu | Thr | Val | Leu | His | Gln | |
| | | | | 85 | | | | | 90 | | | | | 95 | | |
| gac | tgg | ctg | aat | ggc | aag | gag | tac | aag | tgc | aag | gtc | tcc | aac | aaa | gcc | 336 |
| Asp | Trp | Leu | Asn | Gly | Lys | Glu | Tyr | Lys | Cys | Lys | Val | Ser | Asn | Lys | Ala | |
| | | | 100 | | | | | 105 | | | | | 110 | | | |
| ctc | cca | gcc | ccc | atc | gag | gtg | acc | atc | tcc | aaa | gcc | aaa | ggg | cag | ccc | 384 |
| Leu | Pro | Ala | Pro | Ile | Glu | Val | Thr | Ile | Ser | Lys | Ala | Lys | Gly | Gln | Pro | |
| | | 115 | | | | | 120 | | | | | 125 | | | | |
| cga | gaa | cca | cag | gtg | tac | acc | ctg | ccc | cca | tcc | cgg | gag | gag | atg | acc | 432 |
| Arg | Glu | Pro | Gln | Val | Tyr | Thr | Leu | Pro | Pro | Ser | Arg | Glu | Glu | Met | Thr | |
| 130 | | | | | 135 | | | | | 140 | | | | | | |
| aag | aac | cag | gtc | agc | ctg | acc | tgc | ctg | gtc | aaa | ggc | ttc | tat | ccc | agc | 480 |
| Lys | Asn | Gln | Val | Ser | Leu | Thr | Cys | Leu | Val | Lys | Gly | Phe | Tyr | Pro | Ser | |
| 145 | | | | | 150 | | | | | 155 | | | | | 160 | |
| gac | atc | gcc | gtg | gag | tgg | gag | agc | aat | ggg | cag | ccg | gag | aac | aac | tac | 528 |
| Asp | Ile | Ala | Val | Glu | Trp | Glu | Ser | Asn | Gly | Gln | Pro | Glu | Asn | Asn | Tyr | |
| | | | | 165 | | | | | 170 | | | | | 175 | | |
| gac | acc | acg | cct | ccc | gtg | ctg | gac | tcc | gac | ggc | tcc | ttc | ttc | ctc | tat | 576 |
| Asp | Thr | Thr | Pro | Pro | Val | Leu | Asp | Ser | Asp | Gly | Ser | Phe | Phe | Leu | Tyr | |
| | | | 180 | | | | | 185 | | | | | 190 | | | |
| agc | gac | ctc | acc | gtg | gac | aag | agc | agg | tgg | cag | cag | ggg | aac | gtc | ttc | 624 |
| Ser | Asp | Leu | Thr | Val | Asp | Lys | Ser | Arg | Trp | Gln | Gln | Gly | Asn | Val | Phe | |
| | | 195 | | | | | 200 | | | | | 205 | | | | |
| tca | tgc | tcc | gtg | atg | cat | gag | gct | ctg | cac | aac | cac | tac | acg | cag | aag | 672 |
| Ser | Cys | Ser | Val | Met | His | Glu | Ala | Leu | His | Asn | His | Tyr | Thr | Gln | Lys | |
| | 210 | | | | | 215 | | | | | 220 | | | | | |
| agc | ctc | tcc | ctg | tct | ccg | ggt | aaa | tga | | | | | | | | 699 |
| Ser | Leu | Ser | Leu | Ser | Pro | Gly | Lys | | | | | | | | | |
| 225 | | | | | 230 | | | | | | | | | | | |

```
<210> SEQ ID NO 16
<211> LENGTH: 232
<212> TYPE: PRT
<213> ORGANISM: Homo sapiens

<400> SEQUENCE: 16
```

```
Glu Pro Lys Ser Cys Asp Lys Thr His Thr Cys Pro Pro Cys Pro Ala
 1               5                  10                  15
Pro Glu Leu Leu Gly Gly Pro Ser Val Phe Leu Phe Pro Pro Lys Pro
             20                  25                  30
Lys Asp Thr Leu Met Ile Ser Arg Thr Pro Glu Val Thr Cys Val Val
         35                  40                  45
Val Asp Val Ser His Glu Asp Pro Glu Val Lys Phe Asn Trp Tyr Val
 50                  55                  60
Asp Gly Val Glu Val His Asn Ala Lys Thr Lys Pro Arg Glu Glu Gln
 65                  70                  75                  80
Tyr Asn Thr Thr Tyr Arg Val Val Ser Val Leu Thr Val Leu His Gln
                 85                  90                  95
Asp Trp Leu Asn Gly Lys Glu Tyr Lys Cys Lys Val Ser Asn Lys Ala
                100                 105                 110
Leu Pro Ala Pro Ile Glu Val Thr Ile Ser Lys Ala Lys Gly Gln Pro
            115                 120                 125
Arg Glu Pro Gln Val Tyr Thr Leu Pro Pro Ser Arg Glu Glu Met Thr
        130                 135                 140
Lys Asn Gln Val Ser Leu Thr Cys Leu Val Lys Gly Phe Tyr Pro Ser
145                 150                 155                 160
Asp Ile Ala Val Glu Trp Glu Ser Asn Gly Gln Pro Glu Asn Asn Tyr
                165                 170                 175
Asp Thr Thr Pro Pro Val Leu Asp Ser Asp Gly Ser Phe Phe Leu Tyr
            180                 185                 190
Ser Asp Leu Thr Val Asp Lys Ser Arg Trp Gln Gln Gly Asn Val Phe
        195                 200                 205
Ser Cys Ser Val Met His Glu Ala Leu His Asn His Tyr Thr Gln Lys
210                 215                 220
Ser Leu Ser Leu Ser Pro Gly Lys
225                 230

<210> SEQ ID NO 17
<211> LENGTH: 699
<212> TYPE: DNA
<213> ORGANISM: Homo sapiens
<220> FEATURE:
<221> NAME/KEY: CDS
<222> LOCATION: (1)..(699)
<220> FEATURE:
<221> NAME/KEY: mutation
<222> LOCATION: (55)..(55)
<220> FEATURE:
<221> NAME/KEY: mutation
<222> LOCATION: (56)..(56)
<220> FEATURE:
<221> NAME/KEY: mutation
<222> LOCATION: (57)..(57)
<220> FEATURE:
<221> NAME/KEY: mutation
<222> LOCATION: (223)..(223)
<220> FEATURE:
<221> NAME/KEY: mutation
<222> LOCATION: (225)..(225)
<220> FEATURE:
<221> NAME/KEY: mutation
<222> LOCATION: (242)..(242)
<220> FEATURE:
<221> NAME/KEY: mutation
<222> LOCATION: (243)..(243)
<220> FEATURE:
<221> NAME/KEY: mutation
<222> LOCATION: (421)..(421)
<220> FEATURE:
<221> NAME/KEY: mutation
```

<222> LOCATION: (550)..(550)
<220> FEATURE:
<221> NAME/KEY: mutation
<222> LOCATION: (552)..(552)
<223> OTHER INFORMATION: Nucleotide sequence encoding a human IgG1 Fc polypeptide chain containing the substitutions E356K, D399K, L234Y, K290Y, and Y296W

<400> SEQUENCE: 17

```
gag ccc aaa tct tgt gac aaa act cac aca tgc cca ccg tgc cca gca      48
Glu Pro Lys Ser Cys Asp Lys Thr His Thr Cys Pro Pro Cys Pro Ala
1               5                   10                  15 cct gaa tat ctg ggg gga ccg tca gtc ttc ctc ttc ccc cca aaa ccc      96
Pro Glu Tyr Leu Gly Gly Pro Ser Val Phe Leu Phe Pro Pro Lys Pro
            20                  25                  30 aag gac acc ctc atg atc tcc cgg acc cct gag gtc aca tgc gtg gtg     144
Lys Asp Thr Leu Met Ile Ser Arg Thr Pro Glu Val Thr Cys Val Val
        35                  40                  45 gtg gac gtg agc cac gaa gac cct gag gtc aag ttc aac tgg tac gtg     192
Val Asp Val Ser His Glu Asp Pro Glu Val Lys Phe Asn Trp Tyr Val
    50                  55                  60 gac ggc gtg gag gtg cat aat gcc aag aca tat ccg cgg gag gag cag     240
Asp Gly Val Glu Val His Asn Ala Lys Thr Tyr Pro Arg Glu Glu Gln
65                  70                  75                  80 tgg aac agc acg tac cgt gtg gtc agc gtc ctc acc gtc ctg cac cag     288
Trp Asn Ser Thr Tyr Arg Val Val Ser Val Leu Thr Val Leu His Gln
                85                  90                  95 gac tgg ctg aat ggc aag gag tac aag tgc aag gtc tcc aac aaa gcc     336
Asp Trp Leu Asn Gly Lys Glu Tyr Lys Cys Lys Val Ser Asn Lys Ala
            100                 105                 110 ctc cca gcc ccc atc gag aaa acc atc tcc aaa gcc aaa ggg cag ccc     384
Leu Pro Ala Pro Ile Glu Lys Thr Ile Ser Lys Ala Lys Gly Gln Pro
        115                 120                 125 cga gaa cca cag gtg tac acc ctg ccc cca tcc cgg aag gag atg acc     432
Arg Glu Pro Gln Val Tyr Thr Leu Pro Pro Ser Arg Lys Glu Met Thr
    130                 135                 140 aag aac cag gtc agc ctg acc tgc ctg gtc aaa ggc ttc tat ccc agc     480
Lys Asn Gln Val Ser Leu Thr Cys Leu Val Lys Gly Phe Tyr Pro Ser
145                 150                 155                 160 gac atc gcc gtg gag tgg gag agc aat ggg cag ccg gag aac aac tac     528
Asp Ile Ala Val Glu Trp Glu Ser Asn Gly Gln Pro Glu Asn Asn Tyr
                165                 170                 175 aag acc acg cct ccc gtg ctg aag tcc gac ggc tcc ttc ttc ctc tat     576
Lys Thr Thr Pro Pro Val Leu Lys Ser Asp Gly Ser Phe Phe Leu Tyr
            180                 185                 190 agc aag ctc acc gtg gac aag agc agg tgg cag cag ggg aac gtc ttc     624
Ser Lys Leu Thr Val Asp Lys Ser Arg Trp Gln Gln Gly Asn Val Phe
        195                 200                 205 tca tgc tcc gtg atg cat gag gct ctg cac aac cac tac acg cag aag     672
Ser Cys Ser Val Met His Glu Ala Leu His Asn His Tyr Thr Gln Lys
    210                 215                 220 agc ctc tcc ctg tct ccg ggt aaa tga                                  699
Ser Leu Ser Leu Ser Pro Gly Lys
225                 230
```

<210> SEQ ID NO 18
<211> LENGTH: 232
<212> TYPE: PRT
<213> ORGANISM: Homo sapiens

<400> SEQUENCE: 18

Glu Pro Lys Ser Cys Asp Lys Thr His Thr Cys Pro Pro Cys Pro Ala

```
              1               5                  10                 15
        Pro Glu Tyr Leu Gly Gly Pro Ser Val Phe Leu Phe Pro Lys Pro
                        20                  25                  30
        Lys Asp Thr Leu Met Ile Ser Arg Thr Pro Glu Val Thr Cys Val Val
                        35                  40                  45
        Val Asp Val Ser His Glu Asp Pro Glu Val Lys Phe Asn Trp Tyr Val
                        50                  55                  60
        Asp Gly Val Glu Val His Asn Ala Lys Thr Tyr Pro Arg Glu Glu Gln
        65                      70                  75                  80
        Trp Asn Ser Thr Tyr Arg Val Val Ser Val Leu Thr Val Leu His Gln
                        85                  90                  95
        Asp Trp Leu Asn Gly Lys Glu Tyr Lys Cys Lys Val Ser Asn Lys Ala
                        100                 105                 110
        Leu Pro Ala Pro Ile Glu Lys Thr Ile Ser Lys Ala Lys Gly Gln Pro
                        115                 120                 125
        Arg Glu Pro Gln Val Tyr Thr Leu Pro Pro Ser Arg Lys Glu Met Thr
                        130                 135                 140
        Lys Asn Gln Val Ser Leu Thr Cys Leu Val Lys Gly Phe Tyr Pro Ser
        145                     150                 155                 160
        Asp Ile Ala Val Glu Trp Glu Ser Asn Gly Gln Pro Glu Asn Asn Tyr
                        165                 170                 175
        Lys Thr Thr Pro Pro Val Leu Ser Asp Gly Ser Phe Phe Leu Tyr
                        180                 185                 190
        Ser Lys Leu Thr Val Asp Lys Ser Arg Trp Gln Gln Gly Asn Val Phe
                        195                 200                 205
        Ser Cys Ser Val Met His Glu Ala Leu His Asn His Tyr Thr Gln Lys
                        210                 215                 220
        Ser Leu Ser Leu Ser Pro Gly Lys
        225                     230

<210> SEQ ID NO 19
<211> LENGTH: 699
<212> TYPE: DNA
<213> ORGANISM: Homo sapiens
<220> FEATURE:
<221> NAME/KEY: CDS
<222> LOCATION: (1)..(699)
<220> FEATURE:
<221> NAME/KEY: mutation
<222> LOCATION: (343)..(343)
<220> FEATURE:
<221> NAME/KEY: mutation
<222> LOCATION: (344)..(344)
<220> FEATURE:
<221> NAME/KEY: mutation
<222> LOCATION: (345)..(345)
<220> FEATURE:
<221> NAME/KEY: mutation
<222> LOCATION: (355)..(355)
<220> FEATURE:
<221> NAME/KEY: mutation
<222> LOCATION: (356)..(356)
<220> FEATURE:
<221> NAME/KEY: mutation
<222> LOCATION: (357)..(357)
<220> FEATURE:
<221> NAME/KEY: mutation
<222> LOCATION: (529)..(529)
<220> FEATURE:
<221> NAME/KEY: mutation
<222> LOCATION: (531)..(531)
<220> FEATURE:
<221> NAME/KEY: mutation
<222> LOCATION: (580)..(580)
```

```
<220> FEATURE:
<221> NAME/KEY: mutation
<222> LOCATION: (582)..(582)
<223> OTHER INFORMATION: Nucleotide sequence encoding a human IgG1 Fc
      polypeptide chain containing the substitutions K392D, K409D,
      A330M, and K334V

<400> SEQUENCE: 19 gag ccc aaa tct tgt gac aaa act cac aca tgc cca ccg tgc cca gca      48
Glu Pro Lys Ser Cys Asp Lys Thr His Thr Cys Pro Pro Cys Pro Ala
1               5                   10                  15 cct gaa ctc ctg ggg gga ccg tca gtc ttc ctc ttc ccc cca aaa ccc      96
Pro Glu Leu Leu Gly Gly Pro Ser Val Phe Leu Phe Pro Pro Lys Pro
            20                  25                  30 aag gac acc ctc atg atc tcc cgg acc cct gag gtc aca tgc gtg gtg     144
Lys Asp Thr Leu Met Ile Ser Arg Thr Pro Glu Val Thr Cys Val Val
        35                  40                  45 gtg gac gtg agc cac gaa gac cct gag gtc aag ttc aac tgg tac gtg     192
Val Asp Val Ser His Glu Asp Pro Glu Val Lys Phe Asn Trp Tyr Val
    50                  55                  60 gac ggc gtg gag gtg cat aat gcc aag aca aag ccg cgg gag gag cag     240
Asp Gly Val Glu Val His Asn Ala Lys Thr Lys Pro Arg Glu Glu Gln
65                  70                  75                  80 tac aac agc acg tac cgt gtg gtc agc gtc ctc acc gtc ctg cac cag     288
Tyr Asn Ser Thr Tyr Arg Val Val Ser Val Leu Thr Val Leu His Gln
                85                  90                  95 gac tgg ctg aat ggc aag gag tac aag tgc aag gtc tcc aac aaa gcc     336
Asp Trp Leu Asn Gly Lys Glu Tyr Lys Cys Lys Val Ser Asn Lys Ala
            100                 105                 110 ctc cca atg ccc atc gag gtg acc atc tcc aaa gcc aaa ggg cag ccc     384
Leu Pro Met Pro Ile Glu Val Thr Ile Ser Lys Ala Lys Gly Gln Pro
        115                 120                 125 cga gaa cca cag gtg tac acc ctg ccc cca tcc cgg gag gag atg acc     432
Arg Glu Pro Gln Val Tyr Thr Leu Pro Pro Ser Arg Glu Glu Met Thr
    130                 135                 140 aag aac cag gtc agc ctg acc tgc ctg gtc aaa ggc ttc tat ccc agc     480
Lys Asn Gln Val Ser Leu Thr Cys Leu Val Lys Gly Phe Tyr Pro Ser
145                 150                 155                 160 gac atc gcc gtg gag tgg gag agc aat ggg cag ccg gag aac aac tac     528
Asp Ile Ala Val Glu Trp Glu Ser Asn Gly Gln Pro Glu Asn Asn Tyr
                165                 170                 175 gac acc acg cct ccc gtg ctg gac tcc gac ggc tcc ttc ttc ctc tat     576
Asp Thr Thr Pro Pro Val Leu Asp Ser Asp Gly Ser Phe Phe Leu Tyr
            180                 185                 190 agc gac ctc acc gtg gac aag agc agg tgg cag cag ggg aac gtc ttc     624
Ser Asp Leu Thr Val Asp Lys Ser Arg Trp Gln Gln Gly Asn Val Phe
        195                 200                 205 tca tgc tcc gtg atg cat gag gct ctg cac aac cac tac acg cag aag     672
Ser Cys Ser Val Met His Glu Ala Leu His Asn His Tyr Thr Gln Lys
    210                 215                 220 agc ctc tcc ctg tct ccg ggt aaa tga                                 699
Ser Leu Ser Leu Ser Pro Gly Lys
225                 230

<210> SEQ ID NO 20
<211> LENGTH: 232
<212> TYPE: PRT
<213> ORGANISM: Homo sapiens

<400> SEQUENCE: 20

Glu Pro Lys Ser Cys Asp Lys Thr His Thr Cys Pro Pro Cys Pro Ala
1               5                   10                  15
```

```
Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
                35                  40                  45

Val Asp Val Ser His Glu Asp Pro Glu Val Lys Phe Asn Trp Tyr Val
 50                  55                  60

Asp Gly Val Glu Val His Asn Ala Lys Thr Lys Pro Arg Glu Glu Gln
 65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
                100                 105                 110

Leu Pro Met Pro Ile Glu Val Thr Ile Ser Lys Ala Lys Gly Gln Pro
                115                 120                 125

Arg Glu Pro Gln Val Tyr Thr Leu Pro Pro Ser Arg Glu Glu Met Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Asp Thr Thr Pro Pro Val Leu Asp Ser Asp Gly Ser Phe Phe Leu Tyr
                180                 185                 190

Ser Asp Leu Thr Val Asp Lys Ser Arg Trp Gln Gln Gly Asn Val Phe
                195                 200                 205

Ser Cys Ser Val Met His Glu Ala Leu His Asn His Tyr Thr Gln Lys
                210                 215                 220

Ser Leu Ser Leu Ser Pro Gly Lys
225                 230

<210> SEQ ID NO 21
<211> LENGTH: 699
<212> TYPE: DNA
<213> ORGANISM: Homo sapiens
<220> FEATURE:
<221> NAME/KEY: CDS
<222> LOCATION: (1)..(699)
<220> FEATURE:
<221> NAME/KEY: mutation
<222> LOCATION: (343)..(343)
<220> FEATURE:
<221> NAME/KEY: mutation
<222> LOCATION: (344)..(344)
<220> FEATURE:
<221> NAME/KEY: mutation
<222> LOCATION: (355)..(355)
<220> FEATURE:
<221> NAME/KEY: mutation
<222> LOCATION: (356)..(356)
<220> FEATURE:
<221> NAME/KEY: mutation
<222> LOCATION: (357)..(357)
<220> FEATURE:
<221> NAME/KEY: mutation
<222> LOCATION: (529)..(529)
<220> FEATURE:
<221> NAME/KEY: mutation
<222> LOCATION: (531)..(531)
<220> FEATURE:
<221> NAME/KEY: mutation
<222> LOCATION: (580)..(580)
<220> FEATURE:
<221> NAME/KEY: mutation
<222> LOCATION: (582)..(582)
<223> OTHER INFORMATION: Nucleotide sequence encoding a human IgG1 Fc
``` polypeptide chain containing the substitutions K392D, K409D, A330F, and K334V

<400> SEQUENCE: 21

```
gag ccc aaa tct tgt gac aaa act cac aca tgc cca ccg tgc cca gca      48
Glu Pro Lys Ser Cys Asp Lys Thr His Thr Cys Pro Pro Cys Pro Ala
1               5                   10                  15 cct gaa ctc ctg ggg gga ccg tca gtc ttc ctc ttc ccc cca aaa ccc      96
Pro Glu Leu Leu Gly Gly Pro Ser Val Phe Leu Phe Pro Pro Lys Pro
            20                  25                  30 aag gac acc ctc atg atc tcc cgg acc cct gag gtc aca tgc gtg gtg     144
Lys Asp Thr Leu Met Ile Ser Arg Thr Pro Glu Val Thr Cys Val Val
        35                  40                  45 gtg gac gtg agc cac gaa gac cct gag gtc aag ttc aac tgg tac gtg     192
Val Asp Val Ser His Glu Asp Pro Glu Val Lys Phe Asn Trp Tyr Val
50                  55                  60 gac ggc gtg gag gtg cat aat gcc aag aca aag ccg cgg gag gag cag     240
Asp Gly Val Glu Val His Asn Ala Lys Thr Lys Pro Arg Glu Glu Gln
65                  70                  75                  80 tac aac agc acg tac cgt gtg gtc agc gtc ctc acc gtc ctg cac cag     288
Tyr Asn Ser Thr Tyr Arg Val Val Ser Val Leu Thr Val Leu His Gln
                85                  90                  95 gac tgg ctg aat ggc aag gag tac aag tgc aag gtc tcc aac aaa gcc     336
Asp Trp Leu Asn Gly Lys Glu Tyr Lys Cys Lys Val Ser Asn Lys Ala
            100                 105                 110 ctc cca ttc ccc atc gag gtg acc atc tcc aaa gcc aaa ggg cag ccc     384
Leu Pro Phe Pro Ile Glu Val Thr Ile Ser Lys Ala Lys Gly Gln Pro
        115                 120                 125 cga gaa cca cag gtg tac acc ctg ccc cca tcc cgg gag gag atg acc     432
Arg Glu Pro Gln Val Tyr Thr Leu Pro Pro Ser Arg Glu Glu Met Thr
130                 135                 140 aag aac cag gtc agc ctg acc tgc ctg gtc aaa ggc ttc tat ccc agc     480
Lys Asn Gln Val Ser Leu Thr Cys Leu Val Lys Gly Phe Tyr Pro Ser
145                 150                 155                 160 gac atc gcc gtg gag tgg gag agc aat ggg cag ccg gag aac aac tac     528
Asp Ile Ala Val Glu Trp Glu Ser Asn Gly Gln Pro Glu Asn Asn Tyr
                165                 170                 175 gac acc acg cct ccc gtg ctg gac tcc gac ggc tcc ttc ttc ctc tat     576
Asp Thr Thr Pro Pro Val Leu Asp Ser Asp Gly Ser Phe Phe Leu Tyr
            180                 185                 190 agc gac ctc acc gtg gac aag agc agg tgg cag cag ggg aac gtc ttc     624
Ser Asp Leu Thr Val Asp Lys Ser Arg Trp Gln Gln Gly Asn Val Phe
        195                 200                 205 tca tgc tcc gtg atg cat gag gct ctg cac aac cac tac acg cag aag     672
Ser Cys Ser Val Met His Glu Ala Leu His Asn His Tyr Thr Gln Lys
    210                 215                 220 agc ctc tcc ctg tct ccg ggt aaa tga                                 699
Ser Leu Ser Leu Ser Pro Gly Lys
225                 230
```

<210> SEQ ID NO 22
<211> LENGTH: 232
<212> TYPE: PRT
<213> ORGANISM: Homo sapiens

<400> SEQUENCE: 22

```
Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30
```

-continued

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
 50                  55                  60

Asp Gly Val Glu Val His Asn Ala Lys Thr Lys Pro Arg Glu Glu Gln
 65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Phe Pro Ile Glu Val Thr Ile Ser Lys Ala Lys Gly Gln Pro
        115                 120                 125

Arg Glu Pro Gln Val Tyr Thr Leu Pro Pro Ser Arg Glu Glu Met Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Asp Thr Thr Pro Pro Val Leu Asp Ser Asp Gly Ser Phe Phe Leu Tyr
            180                 185                 190

Ser Asp Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
210                 215                 220

Ser Leu Ser Leu Ser Pro Gly Lys
225                 230

<210> SEQ ID NO 23
<211> LENGTH: 699
<212> TYPE: DNA
<213> ORGANISM: Homo sapiens
<220> FEATURE:
<221> NAME/KEY: CDS
<222> LOCATION: (1)..(699)
<220> FEATURE:
<221> NAME/KEY: mutation
<222> LOCATION: (286)..(286)
<220> FEATURE:
<221> NAME/KEY: mutation
<222> LOCATION: (287)..(287)
<220> FEATURE:
<221> NAME/KEY: mutation
<222> LOCATION: (343)..(343)
<220> FEATURE:
<221> NAME/KEY: mutation
<222> LOCATION: (344)..(344)
<220> FEATURE:
<221> NAME/KEY: mutation
<222> LOCATION: (345)..(345)
<220> FEATURE:
<221> NAME/KEY: mutation
<222> LOCATION: (355)..(355)
<220> FEATURE:
<221> NAME/KEY: mutation
<222> LOCATION: (356)..(356)
<220> FEATURE:
<221> NAME/KEY: mutation
<222> LOCATION: (357)..(357)
<220> FEATURE:
<221> NAME/KEY: mutation
<222> LOCATION: (529)..(529)
<220> FEATURE:
<221> NAME/KEY: mutation
<222> LOCATION: (531)..(531)
<220> FEATURE:
<221> NAME/KEY: mutation

```
<222> LOCATION: (580)..(580)
<220> FEATURE:
<221> NAME/KEY: mutation
<222> LOCATION: (582)..(582)
<223> OTHER INFORMATION: Nucleotide sequence encoding a human IgG1 Fc
      polypeptide chain containing the substitutions K392D, K409D,
      Q311M, A330M, and K334V

<400> SEQUENCE: 23 gag ccc aaa tct tgt gac aaa act cac aca tgc cca ccg tgc cca gca         48
Glu Pro Lys Ser Cys Asp Lys Thr His Thr Cys Pro Pro Cys Pro Ala
1               5                   10                  15 cct gaa ctc ctg ggg gga ccg tca gtc ttc ctc ttc ccc cca aaa ccc         96
Pro Glu Leu Leu Gly Gly Pro Ser Val Phe Leu Phe Pro Pro Lys Pro
            20                  25                  30 aag gac acc ctc atg atc tcc cgg acc cct gag gtc aca tgc gtg gtg        144
Lys Asp Thr Leu Met Ile Ser Arg Thr Pro Glu Val Thr Cys Val Val
        35                  40                  45 gtg gac gtg agc cac gaa gac cct gag gtc aag ttc aac tgg tac gtg        192
Val Asp Val Ser His Glu Asp Pro Glu Val Lys Phe Asn Trp Tyr Val
    50                  55                  60 gac ggc gtg gag gtg cat aat gcc aag aca aag ccg cgg gag gag cag        240
Asp Gly Val Glu Val His Asn Ala Lys Thr Lys Pro Arg Glu Glu Gln
65                  70                  75                  80 tac aac agc acg tac cgt gtg gtc agc gtc ctc acc gtc ctg cac atg        288
Tyr Asn Ser Thr Tyr Arg Val Val Ser Val Leu Thr Val Leu His Met
                85                  90                  95 gac tgg ctg aat ggc aag gag tac aag tgc aag gtc tcc aac aaa gcc        336
Asp Trp Leu Asn Gly Lys Glu Tyr Lys Cys Lys Val Ser Asn Lys Ala
            100                 105                 110 ctc cca atg ccc atc gag gtc acc atc tcc aaa gcc aaa ggg cag ccc        384
Leu Pro Met Pro Ile Glu Val Thr Ile Ser Lys Ala Lys Gly Gln Pro
        115                 120                 125 cga gaa cca cag gtg tac acc ctg ccc cca tcc cgg gag gag atg acc        432
Arg Glu Pro Gln Val Tyr Thr Leu Pro Pro Ser Arg Glu Glu Met Thr
    130                 135                 140 aag aac cag gtc agc ctg acc tgc ctg gtc aaa ggc ttc tat ccc agc        480
Lys Asn Gln Val Ser Leu Thr Cys Leu Val Lys Gly Phe Tyr Pro Ser
145                 150                 155                 160 gac atc gcc gtg gag tgg gag agc aat ggg cag ccg gag aac aac tac        528
Asp Ile Ala Val Glu Trp Glu Ser Asn Gly Gln Pro Glu Asn Asn Tyr
                165                 170                 175 gac acc acg cct ccc gtg ctg gac tcc gac ggc tcc ttc ttc ctc tat        576
Asp Thr Thr Pro Pro Val Leu Asp Ser Asp Gly Ser Phe Phe Leu Tyr
            180                 185                 190 agc gac ctc acc gtg gac aag agc agg tgg cag cag ggg aac gtc ttc        624
Ser Asp Leu Thr Val Asp Lys Ser Arg Trp Gln Gln Gly Asn Val Phe
        195                 200                 205 tca tgc tcc gtg atg cat gag gct ctg cac aac cac tac acg cag aag        672
Ser Cys Ser Val Met His Glu Ala Leu His Asn His Tyr Thr Gln Lys
    210                 215                 220 agc ctc tcc ctg tct ccg ggt aaa tga                                    699
Ser Leu Ser Leu Ser Pro Gly Lys
225                 230

<210> SEQ ID NO 24
<211> LENGTH: 232
<212> TYPE: PRT
<213> ORGANISM: Homo sapiens

<400> SEQUENCE: 24

Glu Pro Lys Ser Cys Asp Lys Thr His Thr Cys Pro Pro Cys Pro Ala
```

```
               1               5                   10                  15
           Pro Glu Leu Leu Gly Gly Pro Ser Val Phe Leu Phe Pro Pro Lys Pro
                           20                  25                  30

Lys Asp Thr Leu Met Ile Ser Arg Thr Pro Glu Val Thr Cys Val Val
                       35                  40                  45

Val Asp Val Ser His Glu Asp Pro Glu Val Lys Phe Asn Trp Tyr Val
                   50                  55                  60

Asp Gly Val Glu Val His Asn Ala Lys Thr Lys Pro Arg Glu Glu Gln
           65                  70                  75                  80

Tyr Asn Ser Thr Tyr Arg Val Val Ser Val Leu Thr Val Leu His Met
                           85                  90                  95

Asp Trp Leu Asn Gly Lys Glu Tyr Lys Cys Lys Val Ser Asn Lys Ala
                           100                 105                 110

Leu Pro Met Pro Ile Glu Val Thr Ile Ser Lys Ala Lys Gly Gln Pro
                           115                 120                 125

Arg Glu Pro Gln Val Tyr Thr Leu Pro Pro Ser Arg Glu Glu Met Thr
                   130                 135                 140

Lys Asn Gln Val Ser Leu Thr Cys Leu Val Lys Gly Phe Tyr Pro Ser
           145                 150                 155                 160

Asp Ile Ala Val Glu Trp Glu Ser Asn Gly Gln Pro Glu Asn Asn Tyr
                           165                 170                 175

Asp Thr Thr Pro Pro Val Leu Asp Ser Asp Gly Ser Phe Phe Leu Tyr
                       180                 185                 190

Ser Asp Leu Thr Val Asp Lys Ser Arg Trp Gln Gln Gly Asn Val Phe
                       195                 200                 205

Ser Cys Ser Val Met His Glu Ala Leu His Asn His Tyr Thr Gln Lys
                   210                 215                 220

Ser Leu Ser Leu Ser Pro Gly Lys
           225                 230

<210> SEQ ID NO 25
<211> LENGTH: 699
<212> TYPE: DNA
<213> ORGANISM: Homo sapiens
<220> FEATURE:
<221> NAME/KEY: CDS
<222> LOCATION: (1)..(699)
<220> FEATURE:
<221> NAME/KEY: mutation
<222> LOCATION: (286)..(286)
<220> FEATURE:
<221> NAME/KEY: mutation
<222> LOCATION: (287)..(287)
<220> FEATURE:
<221> NAME/KEY: mutation
<222> LOCATION: (343)..(343)
<220> FEATURE:
<221> NAME/KEY: mutation
<222> LOCATION: (344)..(344)
<220> FEATURE:
<221> NAME/KEY: mutation
<222> LOCATION: (355)..(355)
<220> FEATURE:
<221> NAME/KEY: mutation
<222> LOCATION: (356)..(356)
<220> FEATURE:
<221> NAME/KEY: mutation
<222> LOCATION: (357)..(357)
<220> FEATURE:
<221> NAME/KEY: mutation
<222> LOCATION: (529)..(529)
<220> FEATURE:
<221> NAME/KEY: mutation
<222> LOCATION: (531)..(531)
```

```
<220> FEATURE:
<221> NAME/KEY: mutation
<222> LOCATION: (580)..(580)
<220> FEATURE:
<221> NAME/KEY: mutation
<222> LOCATION: (582)..(582)
<223> OTHER INFORMATION: Nucleotide sequence encoding a human IgG1 Fc
      polypeptide chain containing the substitutions K392D, K409D,
      Q311M, A330F, and K334V

<400> SEQUENCE: 25
```

| | | | | | | | | | | | | | | | | |
|---|---|---|---|---|---|---|---|---|---|---|---|---|---|---|---|---|
| gag | ccc | aaa | tct | tgt | gac | aaa | act | cac | aca | tgc | cca | ccg | tgc | cca | gca | 48 |
| Glu | Pro | Lys | Ser | Cys | Asp | Lys | Thr | His | Thr | Cys | Pro | Pro | Cys | Pro | Ala | |
| 1 | | | | 5 | | | | | 10 | | | | | 15 | | |
| cct | gaa | ctc | ctg | ggg | gga | ccg | tca | gtc | ttc | ctc | ttc | ccc | cca | aaa | ccc | 96 |
| Pro | Glu | Leu | Leu | Gly | Gly | Pro | Ser | Val | Phe | Leu | Phe | Pro | Pro | Lys | Pro | |
| | | | 20 | | | | | 25 | | | | | 30 | | | |
| aag | gac | acc | ctc | atg | atc | tcc | cgg | acc | cct | gag | gtc | aca | tgc | gtg | gtg | 144 |
| Lys | Asp | Thr | Leu | Met | Ile | Ser | Arg | Thr | Pro | Glu | Val | Thr | Cys | Val | Val | |
| | | | 35 | | | | | 40 | | | | | 45 | | | |
| gtg | gac | gtg | agc | cac | gaa | gac | cct | gag | gtc | aag | ttc | aac | tgg | tac | gtg | 192 |
| Val | Asp | Val | Ser | His | Glu | Asp | Pro | Glu | Val | Lys | Phe | Asn | Trp | Tyr | Val | |
| 50 | | | | | 55 | | | | | 60 | | | | | | |
| gac | ggc | gtg | gag | gtg | cat | aat | gcc | aag | aca | aag | ccg | cgg | gag | gag | cag | 240 |
| Asp | Gly | Val | Glu | Val | His | Asn | Ala | Lys | Thr | Lys | Pro | Arg | Glu | Glu | Gln | |
| 65 | | | | | 70 | | | | | 75 | | | | | 80 | |
| tac | aac | agc | acg | tac | cgt | gtg | gtc | agc | gtc | ctc | acc | gtc | ctg | cac | atg | 288 |
| Tyr | Asn | Ser | Thr | Tyr | Arg | Val | Val | Ser | Val | Leu | Thr | Val | Leu | His | Met | |
| | | | | 85 | | | | | 90 | | | | | 95 | | |
| gac | tgg | ctg | aat | ggc | aag | gag | tac | aag | tgc | aag | gtc | tcc | aac | aaa | gcc | 336 |
| Asp | Trp | Leu | Asn | Gly | Lys | Glu | Tyr | Lys | Cys | Lys | Val | Ser | Asn | Lys | Ala | |
| | | | | 100 | | | | | 105 | | | | | 110 | | |
| ctc | cca | ttc | ccc | atc | gag | gtg | acc | atc | tcc | aaa | gcc | aaa | ggg | cag | ccc | 384 |
| Leu | Pro | Phe | Pro | Ile | Glu | Val | Thr | Ile | Ser | Lys | Ala | Lys | Gly | Gln | Pro | |
| | | | 115 | | | | | 120 | | | | | 125 | | | |
| cga | gaa | cca | cag | gtg | tac | acc | ctg | ccc | cca | tcc | cgg | gag | gag | atg | acc | 432 |
| Arg | Glu | Pro | Gln | Val | Tyr | Thr | Leu | Pro | Pro | Ser | Arg | Glu | Glu | Met | Thr | |
| | | 130 | | | | | 135 | | | | | 140 | | | | |
| aag | aac | cag | gtc | agc | ctg | acc | tgc | ctg | gtc | aaa | ggc | ttc | tat | ccc | agc | 480 |
| Lys | Asn | Gln | Val | Ser | Leu | Thr | Cys | Leu | Val | Lys | Gly | Phe | Tyr | Pro | Ser | |
| 145 | | | | | 150 | | | | | 155 | | | | | 160 | |
| gac | atc | gcc | gtg | gag | tgg | gag | agc | aat | ggg | cag | ccg | gag | aac | aac | tac | 528 |
| Asp | Ile | Ala | Val | Glu | Trp | Glu | Ser | Asn | Gly | Gln | Pro | Glu | Asn | Asn | Tyr | |
| | | | | 165 | | | | | 170 | | | | | 175 | | |
| gac | acc | acg | cct | ccc | gtg | ctg | gac | tcc | gac | ggc | tcc | ttc | ttc | ctc | tat | 576 |
| Asp | Thr | Thr | Pro | Pro | Val | Leu | Asp | Ser | Asp | Gly | Ser | Phe | Phe | Leu | Tyr | |
| | | | 180 | | | | | 185 | | | | | 190 | | | |
| agc | gac | ctc | acc | gtg | gac | aag | agc | agg | tgg | cag | cag | ggg | aac | gtc | ttc | 624 |
| Ser | Asp | Leu | Thr | Val | Asp | Lys | Ser | Arg | Trp | Gln | Gln | Gly | Asn | Val | Phe | |
| | | 195 | | | | | 200 | | | | | 205 | | | | |
| tca | tgc | tcc | gtg | atg | cat | gag | gct | ctg | cac | aac | cac | tac | acg | cag | aag | 672 |
| Ser | Cys | Ser | Val | Met | His | Glu | Ala | Leu | His | Asn | His | Tyr | Thr | Gln | Lys | |
| | 210 | | | | | 215 | | | | | 220 | | | | | |
| agc | ctc | tcc | ctg | tct | ccg | ggt | aaa | tga | | | | | | | | 699 |
| Ser | Leu | Ser | Leu | Ser | Pro | Gly | Lys | | | | | | | | | |
| 225 | | | | 230 | | | | | | | | | | | | |

```
<210> SEQ ID NO 26
<211> LENGTH: 232
<212> TYPE: PRT
<213> ORGANISM: Homo sapiens

<400> SEQUENCE: 26
```

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Met
                85                  90                  95

Asp Trp Leu Asn Gly Lys Glu Tyr Lys Cys Lys Val Ser Asn Lys Ala
                100                 105                 110

Leu Pro Phe Pro Ile Glu Val Thr Ile Ser Lys Ala Lys Gly Gln Pro
            115                 120                 125

Arg Glu Pro Gln Val Tyr Thr Leu Pro Pro Ser Arg Glu Glu Met Thr
            130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Asp Thr Thr Pro Pro Val Leu Asp Ser Asp Gly Ser Phe Phe Leu Tyr
            180                 185                 190

Ser Asp Leu Thr Val Asp Lys Ser Arg Trp Gln Gln Gly Asn Val Phe
            195                 200                 205

Ser Cys Ser Val Met His Glu Ala Leu His Asn His Tyr Thr Gln Lys
            210                 215                 220

Ser Leu Ser Leu Ser Pro Gly Lys
225                 230

<210> SEQ ID NO 27
<211> LENGTH: 699
<212> TYPE: DNA
<213> ORGANISM: Homo sapiens
<220> FEATURE:
<221> NAME/KEY: CDS
<222> LOCATION: (1)..(699)
<220> FEATURE:
<221> NAME/KEY: mutation
<222> LOCATION: (248)..(248)
<220> FEATURE:
<221> NAME/KEY: mutation
<222> LOCATION: (343)..(343)
<220> FEATURE:
<221> NAME/KEY: mutation
<222> LOCATION: (344)..(344)
<220> FEATURE:
<221> NAME/KEY: mutation
<222> LOCATION: (345)..(345)
<220> FEATURE:
<221> NAME/KEY: mutation
<222> LOCATION: (355)..(355)
<220> FEATURE:
<221> NAME/KEY: mutation
<222> LOCATION: (356)..(356)
<220> FEATURE:
<221> NAME/KEY: mutation
<222> LOCATION: (357)..(357)
<220> FEATURE:
<221> NAME/KEY: mutation
<222> LOCATION: (529)..(529)
<220> FEATURE:

```
<221> NAME/KEY: mutation
<222> LOCATION: (531)..(531)
<220> FEATURE:
<221> NAME/KEY: mutation
<222> LOCATION: (580)..(580)
<220> FEATURE:
<221> NAME/KEY: mutation
<222> LOCATION: (582)..(582)
<223> OTHER INFORMATION: Nucleotide sequence encoding a human IgG1 Fc
      polypeptide chain containing the substitutions K392D, K409D,
      S298T, A330M, and K334V

<400> SEQUENCE: 27 gag ccc aaa tct tgt gac aaa act cac aca tgc cca ccg tgc cca gca      48
Glu Pro Lys Ser Cys Asp Lys Thr His Thr Cys Pro Pro Cys Pro Ala
1               5                   10                  15 cct gaa ctc ctg ggg gga ccg tca gtc ttc ctc ttc ccc cca aaa ccc      96
Pro Glu Leu Leu Gly Gly Pro Ser Val Phe Leu Phe Pro Pro Lys Pro
            20                  25                  30 aag gac acc ctc atg atc tcc cgg acc cct gag gtc aca tgc gtg gtg     144
Lys Asp Thr Leu Met Ile Ser Arg Thr Pro Glu Val Thr Cys Val Val
        35                  40                  45 gtg gac gtg agc cac gaa gac cct gag gtc aag ttc aac tgg tac gtg     192
Val Asp Val Ser His Glu Asp Pro Glu Val Lys Phe Asn Trp Tyr Val
    50                  55                  60 gac ggc gtg gag gtg cat aat gcc aag aca aag ccg cgg gag gag cag     240
Asp Gly Val Glu Val His Asn Ala Lys Thr Lys Pro Arg Glu Glu Gln
65                  70                  75                  80 tac aac acc acg tac cgt gtg gtc agc gtc ctc acc gtc ctg cac cag     288
Tyr Asn Thr Thr Tyr Arg Val Val Ser Val Leu Thr Val Leu His Gln
                85                  90                  95 gac tgg ctg aat ggc aag gag tac aag tgc aag gtc tcc aac aaa gcc     336
Asp Trp Leu Asn Gly Lys Glu Tyr Lys Cys Lys Val Ser Asn Lys Ala
            100                 105                 110 ctc cca atg ccc atc gag gtg acc atc tcc aaa gcc aaa ggg cag ccc     384
Leu Pro Met Pro Ile Glu Val Thr Ile Ser Lys Ala Lys Gly Gln Pro
        115                 120                 125 cga gaa cca cag gtg tac acc ctg ccc cca tcc cgg gag gag atg acc     432
Arg Glu Pro Gln Val Tyr Thr Leu Pro Pro Ser Arg Glu Glu Met Thr
    130                 135                 140 aag aac cag gtc agc ctg acc tgc ctg gtc aaa ggc ttc tat ccc agc     480
Lys Asn Gln Val Ser Leu Thr Cys Leu Val Lys Gly Phe Tyr Pro Ser
145                 150                 155                 160 gac atc gcc gtg gag tgg gag agc aat ggg cag ccg gag aac aac tac     528
Asp Ile Ala Val Glu Trp Glu Ser Asn Gly Gln Pro Glu Asn Asn Tyr
                165                 170                 175 gac acc acg cct ccc gtg ctg gac tcc gac ggc tcc ttc ttc ctc tat     576
Asp Thr Thr Pro Pro Val Leu Asp Ser Asp Gly Ser Phe Phe Leu Tyr
            180                 185                 190 agc gac ctc acc gtg gac aag agc agg tgg cag cag ggg aac gtc ttc     624
Ser Asp Leu Thr Val Asp Lys Ser Arg Trp Gln Gln Gly Asn Val Phe
        195                 200                 205 tca tgc tcc gtg atg cat gag gct ctg cac aac cac tac acg cag aag     672
Ser Cys Ser Val Met His Glu Ala Leu His Asn His Tyr Thr Gln Lys
    210                 215                 220 agc ctc tcc ctg tct ccg ggt aaa tga                                  699
Ser Leu Ser Leu Ser Pro Gly Lys
225                 230

<210> SEQ ID NO 28
<211> LENGTH: 232
<212> TYPE: PRT
<213> ORGANISM: Homo sapiens
```

<400> SEQUENCE: 28

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Thr Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Met Pro Ile Glu Val Thr Ile Ser Lys Ala Lys Gly Gln Pro
        115                 120                 125

Arg Glu Pro Gln Val Tyr Thr Leu Pro Pro Ser Arg Glu Glu Met Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Asp Thr Thr Pro Pro Val Leu Asp Ser Asp Gly Ser Phe Phe Leu Tyr
            180                 185                 190

Ser Asp Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
210                 215                 220

Ser Leu Ser Leu Ser Pro Gly Lys
225                 230

<210> SEQ ID NO 29
<211> LENGTH: 699
<212> TYPE: DNA
<213> ORGANISM: Homo sapiens
<220> FEATURE:
<221> NAME/KEY: CDS
<222> LOCATION: (1)..(699)
<220> FEATURE:
<221> NAME/KEY: mutation
<222> LOCATION: (248)..(248)
<220> FEATURE:
<221> NAME/KEY: mutation
<222> LOCATION: (343)..(343)
<220> FEATURE:
<221> NAME/KEY: mutation
<222> LOCATION: (344)..(344)
<220> FEATURE:
<221> NAME/KEY: mutation
<222> LOCATION: (355)..(355)
<220> FEATURE:
<221> NAME/KEY: mutation
<222> LOCATION: (356)..(356)
<220> FEATURE:
<221> NAME/KEY: mutation
<222> LOCATION: (357)..(357)
<220> FEATURE:
<221> NAME/KEY: mutation
<222> LOCATION: (529)..(529)
<220> FEATURE:
<221> NAME/KEY: mutation
<222> LOCATION: (531)..(531)
<220> FEATURE:
<221> NAME/KEY: mutation
<222> LOCATION: (580)..(580)
<220> FEATURE:
<221> NAME/KEY: mutation
<222> LOCATION: (582)..(582)
<223> OTHER INFORMATION: Nucleotide sequence encoding a human IgG1 Fc
   polypeptide chain containing the substitutions K392D, K409D,
   S298T, A330F, and K334V

<400> SEQUENCE: 29

| gag | ccc | aaa | tct | tgt | gac | aaa | act | cac | aca | tgc | cca | ccg | tgc | cca | gca | 48 |
| Glu | Pro | Lys | Ser | Cys | Asp | Lys | Thr | His | Thr | Cys | Pro | Pro | Cys | Pro | Ala | |
| 1 | | | | 5 | | | | | 10 | | | | | 15 | | |

| cct | gaa | ctc | ctg | ggg | gga | ccg | tca | gtc | ttc | ctc | ttc | ccc | cca | aaa | ccc | 96 |
| Pro | Glu | Leu | Leu | Gly | Gly | Pro | Ser | Val | Phe | Leu | Phe | Pro | Pro | Lys | Pro | |
| | | 20 | | | | | 25 | | | | | 30 | | | | |

| aag | gac | acc | ctc | atg | atc | tcc | cgg | acc | cct | gag | gtc | aca | tgc | gtg | gtg | 144 |
| Lys | Asp | Thr | Leu | Met | Ile | Ser | Arg | Thr | Pro | Glu | Val | Thr | Cys | Val | Val | |
| | | | 35 | | | | | 40 | | | | | 45 | | | |

| gtg | gac | gtg | agc | cac | gaa | gac | cct | gag | gtc | aag | ttc | aac | tgg | tac | gtg | 192 |
| Val | Asp | Val | Ser | His | Glu | Asp | Pro | Glu | Val | Lys | Phe | Asn | Trp | Tyr | Val | |
| | 50 | | | | | 55 | | | | | 60 | | | | | |

| gac | ggc | gtg | gag | gtg | cat | aat | gcc | aag | aca | aag | ccg | cgg | gag | gag | cag | 240 |
| Asp | Gly | Val | Glu | Val | His | Asn | Ala | Lys | Thr | Lys | Pro | Arg | Glu | Glu | Gln | |
| 65 | | | | | 70 | | | | | 75 | | | | | 80 | |

| tac | aac | acc | acg | tac | cgt | gtg | gtc | agc | gtc | ctc | acc | gtc | ctg | cac | cag | 288 |
| Tyr | Asn | Thr | Thr | Tyr | Arg | Val | Val | Ser | Val | Leu | Thr | Val | Leu | His | Gln | |
| | | | | 85 | | | | | 90 | | | | | 95 | | |

| gac | tgg | ctg | aat | ggc | aag | gag | tac | aag | tgc | aag | gtc | tcc | aac | aaa | gcc | 336 |
| Asp | Trp | Leu | Asn | Gly | Lys | Glu | Tyr | Lys | Cys | Lys | Val | Ser | Asn | Lys | Ala | |
| | | | 100 | | | | | 105 | | | | | 110 | | | |

| ctc | cca | ttc | ccc | atc | gag | gtg | acc | atc | tcc | aaa | gcc | aaa | ggg | cag | ccc | 384 |
| Leu | Pro | Phe | Pro | Ile | Glu | Val | Thr | Ile | Ser | Lys | Ala | Lys | Gly | Gln | Pro | |
| | | 115 | | | | | 120 | | | | | 125 | | | | |

| cga | gaa | cca | cag | gtg | tac | acc | ctg | ccc | cca | tcc | cgg | gag | gag | atg | acc | 432 |
| Arg | Glu | Pro | Gln | Val | Tyr | Thr | Leu | Pro | Pro | Ser | Arg | Glu | Glu | Met | Thr | |
| 130 | | | | | 135 | | | | | 140 | | | | | | |

| aag | aac | cag | gtc | agc | ctg | acc | tgc | ctg | gtc | aaa | ggc | ttc | tat | ccc | agc | 480 |
| Lys | Asn | Gln | Val | Ser | Leu | Thr | Cys | Leu | Val | Lys | Gly | Phe | Tyr | Pro | Ser | |
| 145 | | | | | 150 | | | | | 155 | | | | | 160 | |

| gac | atc | gcc | gtg | gag | tgg | gag | agc | aat | ggg | cag | ccg | gag | aac | aac | tac | 528 |
| Asp | Ile | Ala | Val | Glu | Trp | Glu | Ser | Asn | Gly | Gln | Pro | Glu | Asn | Asn | Tyr | |
| | | | 165 | | | | | 170 | | | | | 175 | | | |

| gac | acc | acg | cct | ccc | gtg | ctg | gac | tcc | gac | ggc | tcc | ttc | ttc | ctc | tat | 576 |
| Asp | Thr | Thr | Pro | Pro | Val | Leu | Asp | Ser | Asp | Gly | Ser | Phe | Phe | Leu | Tyr | |
| | | 180 | | | | | 185 | | | | | 190 | | | | |

| agc | gac | ctc | acc | gtg | gac | aag | agc | agg | tgg | cag | cag | ggg | aac | gtc | ttc | 624 |
| Ser | Asp | Leu | Thr | Val | Asp | Lys | Ser | Arg | Trp | Gln | Gln | Gly | Asn | Val | Phe | |
| | | 195 | | | | | 200 | | | | | 205 | | | | |

| tca | tgc | tcc | gtg | atg | cat | gag | gct | ctg | cac | aac | cac | tac | acg | cag | aag | 672 |
| Ser | Cys | Ser | Val | Met | His | Glu | Ala | Leu | His | Asn | His | Tyr | Thr | Gln | Lys | |
| | 210 | | | | | 215 | | | | | 220 | | | | | |

| agc | ctc | tcc | ctg | tct | ccg | ggt | aaa | tga | | | | | | | | 699 |
| Ser | Leu | Ser | Leu | Ser | Pro | Gly | Lys | | | | | | | | | |
| 225 | | | | | 230 | | | | | | | | | | | |

<210> SEQ ID NO 30
<211> LENGTH: 232
<212> TYPE: PRT
<213> ORGANISM: Homo sapiens

<400> SEQUENCE: 30

```
Glu Pro Lys Ser Cys Asp Lys Thr His Thr Cys Pro Pro Cys Pro Ala
1               5                   10                  15
Pro Glu Leu Leu Gly Gly Pro Ser Val Phe Leu Phe Pro Pro Lys Pro
            20                  25                  30
Lys Asp Thr Leu Met Ile Ser Arg Thr Pro Glu Val Thr Cys Val Val
        35                  40                  45
Val Asp Val Ser His Glu Asp Pro Glu Val Lys Phe Asn Trp Tyr Val
50                  55                  60
Asp Gly Val Glu Val His Asn Ala Lys Thr Lys Pro Arg Glu Glu Gln
65                  70                  75                  80
Tyr Asn Thr Thr Tyr Arg Val Val Ser Val Leu Thr Val Leu His Gln
                85                  90                  95
Asp Trp Leu Asn Gly Lys Glu Tyr Lys Cys Lys Val Ser Asn Lys Ala
            100                 105                 110
Leu Pro Phe Pro Ile Glu Val Thr Ile Ser Lys Ala Lys Gly Gln Pro
        115                 120                 125
Arg Glu Pro Gln Val Tyr Thr Leu Pro Pro Ser Arg Glu Glu Met Thr
130                 135                 140
Lys Asn Gln Val Ser Leu Thr Cys Leu Val Lys Gly Phe Tyr Pro Ser
145                 150                 155                 160
Asp Ile Ala Val Glu Trp Glu Ser Asn Gly Gln Pro Glu Asn Asn Tyr
                165                 170                 175
Asp Thr Thr Pro Pro Val Leu Asp Ser Asp Gly Ser Phe Phe Leu Tyr
            180                 185                 190
Ser Asp Leu Thr Val Asp Lys Ser Arg Trp Gln Gln Gly Asn Val Phe
        195                 200                 205
Ser Cys Ser Val Met His Glu Ala Leu His Asn His Tyr Thr Gln Lys
210                 215                 220
Ser Leu Ser Leu Ser Pro Gly Lys
225                 230
```

```
<210> SEQ ID NO 31
<211> LENGTH: 699
<212> TYPE: DNA
<213> ORGANISM: Homo sapiens
<220> FEATURE:
<221> NAME/KEY: CDS
<222> LOCATION: (1)..(699)
<220> FEATURE:
<221> NAME/KEY: mutation
<222> LOCATION: (70)..(70)
<220> FEATURE:
<221> NAME/KEY: mutation
<222> LOCATION: (71)..(71)
<220> FEATURE:
<221> NAME/KEY: mutation
<222> LOCATION: (72)..(72)
<220> FEATURE:
<221> NAME/KEY: mutation
<222> LOCATION: (343)..(343)
<220> FEATURE:
<221> NAME/KEY: mutation
<222> LOCATION: (344)..(344)
<220> FEATURE:
<221> NAME/KEY: mutation
<222> LOCATION: (345)..(345)
<220> FEATURE:
<221> NAME/KEY: mutation
<222> LOCATION: (355)..(355)
<220> FEATURE:
<221> NAME/KEY: mutation
<222> LOCATION: (356)..(356)
```

```
<220> FEATURE:
<221> NAME/KEY: mutation
<222> LOCATION: (357)..(357)
<220> FEATURE:
<221> NAME/KEY: mutation
<222> LOCATION: (529)..(529)
<220> FEATURE:
<221> NAME/KEY: mutation
<222> LOCATION: (531)..(531)
<220> FEATURE:
<221> NAME/KEY: mutation
<222> LOCATION: (580)..(580)
<220> FEATURE:
<221> NAME/KEY: mutation
<222> LOCATION: (582)..(582)
<223> OTHER INFORMATION: Nucleotide sequence encoding a human IgG1 Fc
      polypeptide chain containing the substitutions K392D, K409D,
      S239D, A330M, and K334V

<400> SEQUENCE: 31
```

| | | | | | | | | | | | | | | | | |
|---|---|---|---|---|---|---|---|---|---|---|---|---|---|---|---|---|
| gag | ccc | aaa | tct | tgt | gac | aaa | act | cac | aca | tgc | cca | ccg | tgc | cca | gca | 48 |
| Glu | Pro | Lys | Ser | Cys | Asp | Lys | Thr | His | Thr | Cys | Pro | Pro | Cys | Pro | Ala | |
| 1 | | | | 5 | | | | | 10 | | | | | 15 | | |
| cct | gaa | ctc | ctg | ggg | gga | ccg | gac | gtc | ttc | ctc | ttc | ccc | cca | aaa | ccc | 96 |
| Pro | Glu | Leu | Leu | Gly | Gly | Pro | Asp | Val | Phe | Leu | Phe | Pro | Pro | Lys | Pro | |
| | | | 20 | | | | | 25 | | | | | 30 | | | |
| aag | gac | acc | ctc | atg | atc | tcc | cgg | acc | cct | gag | gtc | aca | tgc | gtg | gtg | 144 |
| Lys | Asp | Thr | Leu | Met | Ile | Ser | Arg | Thr | Pro | Glu | Val | Thr | Cys | Val | Val | |
| | | 35 | | | | | 40 | | | | | 45 | | | | |
| gtg | gac | gtg | agc | cac | gaa | gac | cct | gag | gtc | aag | ttc | aac | tgg | tac | gtg | 192 |
| Val | Asp | Val | Ser | His | Glu | Asp | Pro | Glu | Val | Lys | Phe | Asn | Trp | Tyr | Val | |
| 50 | | | | | 55 | | | | | 60 | | | | | | |
| gac | ggc | gtg | gag | gtg | cat | aat | gcc | aag | aca | aag | ccg | cgg | gag | gag | cag | 240 |
| Asp | Gly | Val | Glu | Val | His | Asn | Ala | Lys | Thr | Lys | Pro | Arg | Glu | Glu | Gln | |
| 65 | | | | | 70 | | | | | 75 | | | | | 80 | |
| tac | aac | agc | acg | tac | cgt | gtg | gtc | agc | gtc | ctc | acc | gtc | ctg | cac | cag | 288 |
| Tyr | Asn | Ser | Thr | Tyr | Arg | Val | Val | Ser | Val | Leu | Thr | Val | Leu | His | Gln | |
| | | | | 85 | | | | | 90 | | | | | 95 | | |
| gac | tgg | ctg | aat | ggc | aag | gag | tac | aag | tgc | aag | gtc | tcc | aac | aaa | gcc | 336 |
| Asp | Trp | Leu | Asn | Gly | Lys | Glu | Tyr | Lys | Cys | Lys | Val | Ser | Asn | Lys | Ala | |
| | | | | 100 | | | | | 105 | | | | | 110 | | |
| ctc | cca | atg | ccc | atc | gag | gtg | acc | atc | tcc | aaa | gcc | aaa | ggg | cag | ccc | 384 |
| Leu | Pro | Met | Pro | Ile | Glu | Val | Thr | Ile | Ser | Lys | Ala | Lys | Gly | Gln | Pro | |
| | | | 115 | | | | | 120 | | | | | 125 | | | |
| cga | gaa | cca | cag | gtg | tac | acc | ctg | ccc | cca | tcc | cgg | gag | gag | atg | acc | 432 |
| Arg | Glu | Pro | Gln | Val | Tyr | Thr | Leu | Pro | Pro | Ser | Arg | Glu | Glu | Met | Thr | |
| | | 130 | | | | | 135 | | | | | 140 | | | | |
| aag | aac | cag | gtc | agc | ctg | acc | tgc | ctg | gtc | aaa | ggc | ttc | tat | ccc | agc | 480 |
| Lys | Asn | Gln | Val | Ser | Leu | Thr | Cys | Leu | Val | Lys | Gly | Phe | Tyr | Pro | Ser | |
| 145 | | | | | 150 | | | | | 155 | | | | | 160 | |
| gac | atc | gcc | gtg | gag | tgg | gag | agc | aat | ggg | cag | ccg | gag | aac | aac | tac | 528 |
| Asp | Ile | Ala | Val | Glu | Trp | Glu | Ser | Asn | Gly | Gln | Pro | Glu | Asn | Asn | Tyr | |
| | | | | 165 | | | | | 170 | | | | | 175 | | |
| gac | acc | acg | cct | ccc | gtg | ctg | gac | tcc | gac | ggc | tcc | ttc | ttc | ctc | tat | 576 |
| Asp | Thr | Thr | Pro | Pro | Val | Leu | Asp | Ser | Asp | Gly | Ser | Phe | Phe | Leu | Tyr | |
| | | | 180 | | | | | 185 | | | | | 190 | | | |
| agc | gac | ctc | acc | gtg | gac | aag | agc | agg | tgg | cag | cag | ggg | aac | gtc | ttc | 624 |
| Ser | Asp | Leu | Thr | Val | Asp | Lys | Ser | Arg | Trp | Gln | Gln | Gly | Asn | Val | Phe | |
| | | 195 | | | | | 200 | | | | | 205 | | | | |
| tca | tgc | tcc | gtg | atg | cat | gag | gct | ctg | cac | aac | cac | tac | acg | cag | aag | 672 |
| Ser | Cys | Ser | Val | Met | His | Glu | Ala | Leu | His | Asn | His | Tyr | Thr | Gln | Lys | |
| 210 | | | | | 215 | | | | | 220 | | | | | | |
| agc | ctc | tcc | ctg | tct | ccg | ggt | aaa | tga | | | | | | | | 699 |
| Ser | Leu | Ser | Leu | Ser | Pro | Gly | Lys | | | | | | | | | |

225                    230

<210> SEQ ID NO 32
<211> LENGTH: 232
<212> TYPE: PRT
<213> ORGANISM: Homo sapiens

<400> SEQUENCE: 32

Glu Pro Lys Ser Cys Asp Lys Thr His Thr Cys Pro Pro Cys Pro Ala
1               5                   10                  15

Pro Glu Leu Leu Gly Gly Pro Asp Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Met Pro Ile Glu Val Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Asp Thr Thr Pro Pro Val Leu Asp Ser Asp Gly Ser Phe Phe Leu Tyr
            180                 185                 190

Ser Asp Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 33
<211> LENGTH: 699
<212> TYPE: DNA
<213> ORGANISM: Homo sapiens
<220> FEATURE:
<221> NAME/KEY: CDS
<222> LOCATION: (1)..(699)
<220> FEATURE:
<221> NAME/KEY: mutation
<222> LOCATION: (70)..(70)
<220> FEATURE:
<221> NAME/KEY: mutation
<222> LOCATION: (71)..(71)
<220> FEATURE:
<221> NAME/KEY: mutation
<222> LOCATION: (72)..(72)
<220> FEATURE:
<221> NAME/KEY: mutation
<222> LOCATION: (248)..(248)
<220> FEATURE:
<221> NAME/KEY: mutation
<222> LOCATION: (355)..(355)
<220> FEATURE:

```
<221> NAME/KEY: mutation
<222> LOCATION: (356)..(356)
<220> FEATURE:
<221> NAME/KEY: mutation
<222> LOCATION: (357)..(357)
<220> FEATURE:
<221> NAME/KEY: mutation
<222> LOCATION: (529)..(529)
<220> FEATURE:
<221> NAME/KEY: mutation
<222> LOCATION: (531)..(531)
<220> FEATURE:
<221> NAME/KEY: mutation
<222> LOCATION: (580)..(580)
<220> FEATURE:
<221> NAME/KEY: mutation
<222> LOCATION: (582)..(582)
<223> OTHER INFORMATION: Nucleotide sequence encoding a human IgG1 Fc
      polypeptide chain containing the substitutions K392D, K409D,
      S239D, S298T, and K334V

<400> SEQUENCE: 33
```

| | | | | | | | | | | | | | | | | |
|---|---|---|---|---|---|---|---|---|---|---|---|---|---|---|---|---|
| gag | ccc | aaa | tct | tgt | gac | aaa | act | cac | aca | tgc | cca | ccg | tgc | cca | gca | 48 |
| Glu | Pro | Lys | Ser | Cys | Asp | Lys | Thr | His | Thr | Cys | Pro | Pro | Cys | Pro | Ala | |
| 1 | | | | 5 | | | | | 10 | | | | | 15 | | |
| cct | gaa | ctc | ctg | ggg | gga | ccg | gac | gtc | ttc | ctc | ttc | ccc | cca | aaa | ccc | 96 |
| Pro | Glu | Leu | Leu | Gly | Gly | Pro | Asp | Val | Phe | Leu | Phe | Pro | Pro | Lys | Pro | |
| | | | 20 | | | | | 25 | | | | | 30 | | | |
| aag | gac | acc | ctc | atg | atc | tcc | cgg | acc | cct | gag | gtc | aca | tgc | gtg | gtg | 144 |
| Lys | Asp | Thr | Leu | Met | Ile | Ser | Arg | Thr | Pro | Glu | Val | Thr | Cys | Val | Val | |
| | | 35 | | | | | 40 | | | | | 45 | | | | |
| gtg | gac | gtg | agc | cac | gaa | gac | cct | gag | gtc | aag | ttc | aac | tgg | tac | gtg | 192 |
| Val | Asp | Val | Ser | His | Glu | Asp | Pro | Glu | Val | Lys | Phe | Asn | Trp | Tyr | Val | |
| 50 | | | | | 55 | | | | | 60 | | | | | | |
| gac | ggc | gtg | gag | gtg | cat | aat | gcc | aag | aca | aag | ccg | cgg | gag | gag | cag | 240 |
| Asp | Gly | Val | Glu | Val | His | Asn | Ala | Lys | Thr | Lys | Pro | Arg | Glu | Glu | Gln | |
| 65 | | | | | 70 | | | | | 75 | | | | | 80 | |
| tac | aac | acc | acg | tac | cgt | gtg | gtc | agc | gtc | ctc | acc | gtc | ctg | cac | cag | 288 |
| Tyr | Asn | Thr | Thr | Tyr | Arg | Val | Val | Ser | Val | Leu | Thr | Val | Leu | His | Gln | |
| | | | | 85 | | | | | 90 | | | | | 95 | | |
| gac | tgg | ctg | aat | ggc | aag | gag | tac | aag | tgc | aag | gtc | tcc | aac | aaa | gcc | 336 |
| Asp | Trp | Leu | Asn | Gly | Lys | Glu | Tyr | Lys | Cys | Lys | Val | Ser | Asn | Lys | Ala | |
| | | | 100 | | | | | 105 | | | | | 110 | | | |
| ctc | cca | gcc | ccc | atc | gag | gtg | acc | atc | tcc | aaa | gcc | aaa | ggg | cag | ccc | 384 |
| Leu | Pro | Ala | Pro | Ile | Glu | Val | Thr | Ile | Ser | Lys | Ala | Lys | Gly | Gln | Pro | |
| | | 115 | | | | | 120 | | | | | 125 | | | | |
| cga | gaa | cca | cag | gtg | tac | acc | ctg | ccc | cca | tcc | cgg | gag | gag | atg | acc | 432 |
| Arg | Glu | Pro | Gln | Val | Tyr | Thr | Leu | Pro | Pro | Ser | Arg | Glu | Glu | Met | Thr | |
| 130 | | | | | 135 | | | | | 140 | | | | | | |
| aag | aac | cag | gtc | agc | ctg | acc | tgc | ctg | gtc | aaa | ggc | ttc | tat | ccc | agc | 480 |
| Lys | Asn | Gln | Val | Ser | Leu | Thr | Cys | Leu | Val | Lys | Gly | Phe | Tyr | Pro | Ser | |
| 145 | | | | | 150 | | | | | 155 | | | | | 160 | |
| gac | atc | gcc | gtg | gag | tgg | gag | agc | aat | ggg | cag | ccg | gag | aac | aac | tac | 528 |
| Asp | Ile | Ala | Val | Glu | Trp | Glu | Ser | Asn | Gly | Gln | Pro | Glu | Asn | Asn | Tyr | |
| | | | | 165 | | | | | 170 | | | | | 175 | | |
| gac | acc | acg | cct | ccc | gtg | ctg | gac | tcc | gac | ggc | tcc | ttc | ttc | ctc | tat | 576 |
| Asp | Thr | Thr | Pro | Pro | Val | Leu | Asp | Ser | Asp | Gly | Ser | Phe | Phe | Leu | Tyr | |
| | | | 180 | | | | | 185 | | | | | 190 | | | |
| agc | gac | ctc | acc | gtg | gac | aag | agc | agg | tgg | cag | cag | ggg | aac | gtc | ttc | 624 |
| Ser | Asp | Leu | Thr | Val | Asp | Lys | Ser | Arg | Trp | Gln | Gln | Gly | Asn | Val | Phe | |
| | | 195 | | | | | 200 | | | | | 205 | | | | |
| tca | tgc | tcc | gtg | atg | cat | gag | gct | ctg | cac | aac | cac | tac | acg | cag | aag | 672 |
| Ser | Cys | Ser | Val | Met | His | Glu | Ala | Leu | His | Asn | His | Tyr | Thr | Gln | Lys | |
| 210 | | | | | 215 | | | | | 220 | | | | | | |

```
agc ctc tcc ctg tct ccg ggt aaa tga                                    699
Ser Leu Ser Leu Ser Pro Gly Lys
225                 230
```

<210> SEQ ID NO 34
<211> LENGTH: 232
<212> TYPE: PRT
<213> ORGANISM: Homo sapiens

<400> SEQUENCE: 34

```
Glu Pro Lys Ser Cys Asp Lys Thr His Thr Cys Pro Pro Cys Pro Ala
1               5                   10                  15

Pro Glu Leu Leu Gly Gly Pro Asp Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Thr Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Val Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Asp Thr Thr Pro Pro Val Leu Asp Ser Asp Gly Ser Phe Phe Leu Tyr
            180                 185                 190

Ser Asp Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230
```

<210> SEQ ID NO 35
<211> LENGTH: 176
<212> TYPE: PRT
<213> ORGANISM: Homo sapiens

<400> SEQUENCE: 35

```
Arg Thr Glu Asp Leu Pro Lys Ala Val Val Phe Leu Glu Pro Gln Trp
1               5                   10                  15

Tyr Ser Val Leu Glu Lys Asp Ser Val Thr Leu Lys Cys Gln Gly Ala
            20                  25                  30

Tyr Ser Pro Glu Asp Asn Ser Thr Gln Trp Phe His Asn Glu Ser Leu
        35                  40                  45

Ile Ser Ser Gln Ala Ser Ser Tyr Phe Ile Asp Ala Ala Thr Val Asn
    50                  55                  60

Asp Ser Gly Glu Tyr Arg Cys Gln Thr Asn Leu Ser Thr Leu Ser Asp
65                  70                  75                  80
```

```
Pro Val Gln Leu Glu Val His Ile Gly Trp Leu Leu Leu Gln Ala Pro
                85                  90                  95

Arg Trp Val Phe Lys Glu Asp Pro Ile His Leu Arg Cys His Ser
            100                 105                 110

Trp Lys Asn Thr Ala Leu His Lys Val Thr Tyr Leu Gln Asn Gly Lys
        115                 120                 125

Asp Arg Lys Tyr Phe His His Asn Ser Asp Phe His Ile Pro Lys Ala
    130                 135                 140

Thr Leu Lys Asp Ser Gly Ser Tyr Phe Cys Arg Gly Leu Val Gly Ser
145                 150                 155                 160

Lys Asn Val Ser Ser Glu Thr Val Asn Ile Thr Ile Thr Gln Gly Leu
                165                 170                 175

<210> SEQ ID NO 36
<211> LENGTH: 699
<212> TYPE: DNA
<213> ORGANISM: Homo sapiens
<220> FEATURE:
<221> NAME/KEY: CDS
<222> LOCATION: (1)..(699)
<220> FEATURE:
<221> NAME/KEY: mutation
<222> LOCATION: (343)..(343)
<220> FEATURE:
<221> NAME/KEY: mutation
<222> LOCATION: (344)..(344)
<220> FEATURE:
<221> NAME/KEY: mutation
<222> LOCATION: (345)..(345)
<220> FEATURE:
<221> NAME/KEY: mutation
<222> LOCATION: (355)..(355)
<220> FEATURE:
<221> NAME/KEY: mutation
<222> LOCATION: (356)..(356)
<220> FEATURE:
<221> NAME/KEY: mutation
<222> LOCATION: (357)..(357)
<220> FEATURE:
<221> NAME/KEY: mutation
<222> LOCATION: (529)..(529)
<220> FEATURE:
<221> NAME/KEY: mutation
<222> LOCATION: (531)..(531)
<220> FEATURE:
<221> NAME/KEY: mutation
<222> LOCATION: (580)..(580)
<220> FEATURE:
<221> NAME/KEY: mutation
<222> LOCATION: (582)..(582)
<223> OTHER INFORMATION: Nucleotide sequence encoding a human IgG1 Fc
      polypeptide chain containing the substitutions A330M, K334V,
      K392D, and K409D

<400> SEQUENCE: 36 gag ccc aaa tct tgt gac aaa act cac aca tgc cca ccg tgc cca gca      48
Glu Pro Lys Ser Cys Asp Lys Thr His Thr Cys Pro Pro Cys Pro Ala
1               5                   10                  15 cct gaa ctc ctg ggg gga ccg tca gtc ttc ctc ttc ccc cca aaa ccc      96
Pro Glu Leu Leu Gly Gly Pro Ser Val Phe Leu Phe Pro Pro Lys Pro
            20                  25                  30 aag gac acc ctc atg atc tcc cgg acc cct gag gtc aca tgc gtg gtg     144
Lys Asp Thr Leu Met Ile Ser Arg Thr Pro Glu Val Thr Cys Val Val
        35                  40                  45 gtg gac gtg agc cac gaa gac cct gag gtc aag ttc aac tgg tac gtg     192
Val Asp Val Ser His Glu Asp Pro Glu Val Lys Phe Asn Trp Tyr Val
    50                  55                  60
```

| | | | | | | | | | | | | | | | |
|---|---|---|---|---|---|---|---|---|---|---|---|---|---|---|---|
| gac | ggc | gtg | gag | gtg | cat | aat | gcc | aag | aca | aag | ccg | cgg | gag | gag | cag | 240 |
| Asp | Gly | Val | Glu | Val | His | Asn | Ala | Lys | Thr | Lys | Pro | Arg | Glu | Glu | Gln | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| tac | aac | agc | acg | tac | cgt | gtg | gtc | agc | gtc | ctc | acc | gtc | ctg | cac | cag | 288 |
| Tyr | Asn | Ser | Thr | Tyr | Arg | Val | Val | Ser | Val | Leu | Thr | Val | Leu | His | Gln | |
| | | | | 85 | | | | | 90 | | | | | 95 | | |

| | | | | | | | | | | | | | | | | |
|---|---|---|---|---|---|---|---|---|---|---|---|---|---|---|---|---|
| gac | tgg | ctg | aat | ggc | aag | gag | tac | aag | tgc | aag | gtc | tcc | aac | aaa | gcc | 336 |
| Asp | Trp | Leu | Asn | Gly | Lys | Glu | Tyr | Lys | Cys | Lys | Val | Ser | Asn | Lys | Ala | |
| | | | | 100 | | | | | 105 | | | | | 110 | | |

| | | | | | | | | | | | | | | | | |
|---|---|---|---|---|---|---|---|---|---|---|---|---|---|---|---|---|
| ctc | cca | atg | ccc | atc | gag | gtg | acc | atc | tcc | aaa | gcc | aaa | ggg | cag | ccc | 384 |
| Leu | Pro | Met | Pro | Ile | Glu | Val | Thr | Ile | Ser | Lys | Ala | Lys | Gly | Gln | Pro | |
| | | 115 | | | | | 120 | | | | | 125 | | | | |

| | | | | | | | | | | | | | | | | |
|---|---|---|---|---|---|---|---|---|---|---|---|---|---|---|---|---|
| cga | gaa | cca | cag | gtg | tac | acc | ctg | ccc | cca | tcc | cgg | gag | gag | atg | acc | 432 |
| Arg | Glu | Pro | Gln | Val | Tyr | Thr | Leu | Pro | Pro | Ser | Arg | Glu | Glu | Met | Thr | |
| | 130 | | | | | 135 | | | | | 140 | | | | | |

| | | | | | | | | | | | | | | | | |
|---|---|---|---|---|---|---|---|---|---|---|---|---|---|---|---|---|
| aag | aac | cag | gtc | agc | ctg | acc | tgc | ctg | gtc | aaa | ggc | ttc | tat | ccc | agc | 480 |
| Lys | Asn | Gln | Val | Ser | Leu | Thr | Cys | Leu | Val | Lys | Gly | Phe | Tyr | Pro | Ser | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| gac | atc | gcc | gtg | gag | tgg | gag | agc | aat | ggg | cag | ccg | gag | aac | aac | tac | 528 |
| Asp | Ile | Ala | Val | Glu | Trp | Glu | Ser | Asn | Gly | Gln | Pro | Glu | Asn | Asn | Tyr | |
| | | | | 165 | | | | | 170 | | | | | 175 | | |

| | | | | | | | | | | | | | | | | |
|---|---|---|---|---|---|---|---|---|---|---|---|---|---|---|---|---|
| gac | acc | acg | cct | ccc | gtg | ctg | gac | tcc | gac | ggc | tcc | ttc | ttc | ctc | tat | 576 |
| Asp | Thr | Thr | Pro | Pro | Val | Leu | Asp | Ser | Asp | Gly | Ser | Phe | Phe | Leu | Tyr | |
| | | | 180 | | | | | 185 | | | | | 190 | | | |

| | | | | | | | | | | | | | | | | |
|---|---|---|---|---|---|---|---|---|---|---|---|---|---|---|---|---|
| agc | gac | ctc | acc | gtg | gac | aag | agc | agg | tgg | cag | cag | ggg | aac | gtc | ttc | 624 |
| Ser | Asp | Leu | Thr | Val | Asp | Lys | Ser | Arg | Trp | Gln | Gln | Gly | Asn | Val | Phe | |
| | | | 195 | | | | | 200 | | | | | 205 | | | |

| | | | | | | | | | | | | | | | | |
|---|---|---|---|---|---|---|---|---|---|---|---|---|---|---|---|---|
| tca | tgc | tcc | gtg | atg | cat | gag | gct | ctg | cac | aac | cac | tac | acg | cag | aag | 672 |
| Ser | Cys | Ser | Val | Met | His | Glu | Ala | Leu | His | Asn | His | Tyr | Thr | Gln | Lys | |
| | | 210 | | | | | 215 | | | | | 220 | | | | |

| | | | | | | | | |
|---|---|---|---|---|---|---|---|---|
| agc | ctc | tcc | ctg | tct | ccg | ggt | aaa | tga | 699 |
| Ser | Leu | Ser | Leu | Ser | Pro | Gly | Lys | | |
| 225 | | | | | 230 | | | | |

<210> SEQ ID NO 37
<211> LENGTH: 232
<212> TYPE: PRT
<213> ORGANISM: Homo sapiens

<400> SEQUENCE: 37

Glu Pro Lys Ser Cys Asp Lys Thr His Thr Cys Pro Pro Cys Pro Ala
1               5                  10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Met Pro Ile Glu Val Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

-continued

```
Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Asp Thr Thr Pro Pro Val Leu Asp Ser Asp Gly Ser Phe Phe Leu Tyr
            180                 185                 190

Ser Asp Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 38
<211> LENGTH: 699
<212> TYPE: DNA
<213> ORGANISM: Homo sapiens
<220> FEATURE:
<221> NAME/KEY: CDS
<222> LOCATION: (1)..(699)
<220> FEATURE:
<221> NAME/KEY: mutation
<222> LOCATION: (55)..(55)
<220> FEATURE:
<221> NAME/KEY: mutation
<222> LOCATION: (56)..(56)
<220> FEATURE:
<221> NAME/KEY: mutation
<222> LOCATION: (57)..(57)
<220> FEATURE:
<221> NAME/KEY: mutation
<222> LOCATION: (242)..(242)
<220> FEATURE:
<221> NAME/KEY: mutation
<222> LOCATION: (243)..(243)
<220> FEATURE:
<221> NAME/KEY: mutation
<222> LOCATION: (421)..(421)
<220> FEATURE:
<221> NAME/KEY: mutation
<222> LOCATION: (550)..(550)
<220> FEATURE:
<221> NAME/KEY: mutation
<222> LOCATION: (552)..(552)
<223> OTHER INFORMATION: Nucleotide sequence encoding a human IgG1 Fc
      polypeptide chain containing the substitutions L234Y, Y296W,
      E356K, and D399K

<400> SEQUENCE: 38 gag ccc aaa tct tgt gac aaa act cac aca tgc cca ccg tgc cca gca    48
Glu Pro Lys Ser Cys Asp Lys Thr His Thr Cys Pro Pro Cys Pro Ala
1               5                   10                  15 cct gaa tat ctg ggg gga ccg tca gtc ttc ctc ttc ccc cca aaa ccc    96
Pro Glu Tyr Leu Gly Gly Pro Ser Val Phe Leu Phe Pro Pro Lys Pro
                20                  25                  30 aag gac acc ctc atg atc tcc cgg acc cct gag gtc aca tgc gtg gtg    144
Lys Asp Thr Leu Met Ile Ser Arg Thr Pro Glu Val Thr Cys Val Val
            35                  40                  45 gtg gac gtg agc cac gaa gac cct gag gtc aag ttc aac tgg tac gtg    192
Val Asp Val Ser His Glu Asp Pro Glu Val Lys Phe Asn Trp Tyr Val
50                  55                  60 gac ggc gtg gag gtg cat aat gcc aag aca aag ccg cgg gag gag cag    240
Asp Gly Val Glu Val His Asn Ala Lys Thr Lys Pro Arg Glu Glu Gln
65                  70                  75                  80 tgg aac agc acg tac cgt gtg gtc agc gtc ctc acc gtc ctg cac cag    288
Trp Asn Ser Thr Tyr Arg Val Val Ser Val Leu Thr Val Leu His Gln
                85                  90                  95
```

```
gac tgg ctg aat ggc aag gag tac aag tgc aag gtc tcc aac aaa gcc      336
Asp Trp Leu Asn Gly Lys Glu Tyr Lys Cys Lys Val Ser Asn Lys Ala
        100                 105                 110 ctc cca gcc ccc atc gag aaa acc atc tcc aaa gcc aaa ggg cag ccc      384
Leu Pro Ala Pro Ile Glu Lys Thr Ile Ser Lys Ala Lys Gly Gln Pro
    115                 120                 125 cga gaa cca cag gtg tac acc ctg ccc cca tcc cgg aag gag atg acc      432
Arg Glu Pro Gln Val Tyr Thr Leu Pro Pro Ser Arg Lys Glu Met Thr
130                 135                 140 aag aac cag gtc agc ctg acc tgc ctg gtc aaa ggc ttc tat ccc agc      480
Lys Asn Gln Val Ser Leu Thr Cys Leu Val Lys Gly Phe Tyr Pro Ser
145                 150                 155                 160 gac atc gcc gtg gag tgg gag agc aat ggg cag ccg gag aac aac tac      528
Asp Ile Ala Val Glu Trp Glu Ser Asn Gly Gln Pro Glu Asn Asn Tyr
                165                 170                 175 aag acc acg cct ccc gtg ctg aag tcc gac ggc tcc ttc ttc ctc tat      576
Lys Thr Thr Pro Pro Val Leu Lys Ser Asp Gly Ser Phe Phe Leu Tyr
            180                 185                 190 agc aag ctc acc gtg gac aag agc agg tgg cag cag ggg aac gtc ttc      624
Ser Lys Leu Thr Val Asp Lys Ser Arg Trp Gln Gln Gly Asn Val Phe
        195                 200                 205 tca tgc tcc gtg atg cat gag gct ctg cac aac cac tac acg cag aag      672
Ser Cys Ser Val Met His Glu Ala Leu His Asn His Tyr Thr Gln Lys
210                 215                 220 agc ctc tcc ctg tct ccg ggt aaa tga                                  699
Ser Leu Ser Leu Ser Pro Gly Lys
225                 230

<210> SEQ ID NO 39
<211> LENGTH: 232
<212> TYPE: PRT
<213> ORGANISM: Homo sapiens

<400> SEQUENCE: 39

Glu Pro Lys Ser Cys Asp Lys Thr His Thr Cys Pro Pro Cys Pro Ala
1               5                   10                  15

Pro Glu Tyr Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Trp Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Lys Glu Met Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Lys Ser Asp Gly Ser Phe Phe Leu Tyr
```

|    |    |    | 180 |    |    |    | 185 |    |    |    | 190 |    |
|----|----|----|----|----|----|----|----|----|----|----|----|----|

Ser Lys Leu Thr Val Asp Lys Ser Arg Trp Gln Gln Gly Asn Val Phe
        195               200               205

Ser Cys Ser Val Met His Glu Ala Leu His Asn His Tyr Thr Gln Lys
210               215               220

Ser Leu Ser Leu Ser Pro Gly Lys
225               230

<210> SEQ ID NO 40
<211> LENGTH: 699
<212> TYPE: DNA
<213> ORGANISM: Homo sapiens
<220> FEATURE:
<221> NAME/KEY: CDS
<222> LOCATION: (1)..(699)
<220> FEATURE:
<221> NAME/KEY: mutation
<222> LOCATION: (223)..(223)
<220> FEATURE:
<221> NAME/KEY: mutation
<222> LOCATION: (225)..(225)
<220> FEATURE:
<221> NAME/KEY: mutation
<222> LOCATION: (242)..(242)
<220> FEATURE:
<221> NAME/KEY: mutation
<222> LOCATION: (243)..(243)
<220> FEATURE:
<221> NAME/KEY: mutation
<222> LOCATION: (421)..(421)
<220> FEATURE:
<221> NAME/KEY: mutation
<222> LOCATION: (550)..(550)
<220> FEATURE:
<221> NAME/KEY: mutation
<222> LOCATION: (552)..(552)
<223> OTHER INFORMATION: Nucleotide sequence encoding a human IgG1 Fc
     polypeptide chain containing the substitutions K290Y, Y296W,
     E356K, and D399K

<400> SEQUENCE: 40

| | | | | | | | | | | | | | | | | |
|---|---|---|---|---|---|---|---|---|---|---|---|---|---|---|---|---|
| gag | ccc | aaa | tct | tgt | gac | aaa | act | cac | aca | tgc | cca | ccg | tgc | cca | gca | 48 |
| Glu | Pro | Lys | Ser | Cys | Asp | Lys | Thr | His | Thr | Cys | Pro | Pro | Cys | Pro | Ala | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| cct | gaa | ctc | ctg | ggg | gga | ccg | tca | gtc | ttc | ctc | ttc | ccc | cca | aaa | ccc | 96 |
| Pro | Glu | Leu | Leu | Gly | Gly | Pro | Ser | Val | Phe | Leu | Phe | Pro | Pro | Lys | Pro | |
| | | | 20 | | | | | 25 | | | | | 30 | | | |

| | | | | | | | | | | | | | | | | |
|---|---|---|---|---|---|---|---|---|---|---|---|---|---|---|---|---|
| aag | gac | acc | ctc | atg | atc | tcc | cgg | acc | cct | gag | gtc | aca | tgc | gtg | gtg | 144 |
| Lys | Asp | Thr | Leu | Met | Ile | Ser | Arg | Thr | Pro | Glu | Val | Thr | Cys | Val | Val | |
| | | 35 | | | | | 40 | | | | | 45 | | | | |

| | | | | | | | | | | | | | | | | |
|---|---|---|---|---|---|---|---|---|---|---|---|---|---|---|---|---|
| gtg | gac | gtg | agc | cac | gaa | gac | cct | gag | gtc | aag | ttc | aac | tgg | tac | gtg | 192 |
| Val | Asp | Val | Ser | His | Glu | Asp | Pro | Glu | Val | Lys | Phe | Asn | Trp | Tyr | Val | |
| | 50 | | | | | 55 | | | | | 60 | | | | | |

| | | | | | | | | | | | | | | | | |
|---|---|---|---|---|---|---|---|---|---|---|---|---|---|---|---|---|
| gac | ggc | gtg | gag | gtg | cat | aat | gcc | aag | aca | tat | ccg | cgg | gag | gag | cag | 240 |
| Asp | Gly | Val | Glu | Val | His | Asn | Ala | Lys | Thr | Tyr | Pro | Arg | Glu | Glu | Gln | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| tgg | aac | agc | acg | tac | cgt | gtg | gtc | agc | gtc | ctc | acc | gtc | ctg | cac | cag | 288 |
| Trp | Asn | Ser | Thr | Tyr | Arg | Val | Val | Ser | Val | Leu | Thr | Val | Leu | His | Gln | |
| | | | | 85 | | | | | 90 | | | | | 95 | | |

| | | | | | | | | | | | | | | | | |
|---|---|---|---|---|---|---|---|---|---|---|---|---|---|---|---|---|
| gac | tgg | ctg | aat | ggc | aag | gag | tac | aag | tgc | aag | gtc | tcc | aac | aaa | gcc | 336 |
| Asp | Trp | Leu | Asn | Gly | Lys | Glu | Tyr | Lys | Cys | Lys | Val | Ser | Asn | Lys | Ala | |
| | | | 100 | | | | | 105 | | | | | 110 | | | |

| | | | | | | | | | | | | | | | | |
|---|---|---|---|---|---|---|---|---|---|---|---|---|---|---|---|---|
| ctc | cca | gcc | ccc | atc | gag | aaa | acc | atc | tcc | aaa | gcc | aaa | ggg | cag | ccc | 384 |
| Leu | Pro | Ala | Pro | Ile | Glu | Lys | Thr | Ile | Ser | Lys | Ala | Lys | Gly | Gln | Pro | |
| | | 115 | | | | | 120 | | | | | 125 | | | | |

| | | | | | | | | | | | | | | | | |
|---|---|---|---|---|---|---|---|---|---|---|---|---|---|---|---|---|
| cga | gaa | cca | cag | gtg | tac | acc | ctg | ccc | cca | tcc | cgg | aag | gag | atg | acc | 432 |

```
                Arg Glu Pro Gln Val Tyr Thr Leu Pro Pro Ser Arg Lys Glu Met Thr
                    130                 135                 140 aag aac cag gtc agc ctg acc tgc ctg gtc aaa ggc ttc tat ccc agc         480
Lys Asn Gln Val Ser Leu Thr Cys Leu Val Lys Gly Phe Tyr Pro Ser
145                 150                 155                 160 gac atc gcc gtg gag tgg gag agc aat ggg cag ccg gag aac aac tac         528
Asp Ile Ala Val Glu Trp Glu Ser Asn Gly Gln Pro Glu Asn Asn Tyr
                165                 170                 175 aag acc acg cct ccc gtg ctg aag tcc gac ggc tcc ttc ttc ctc tat         576
Lys Thr Thr Pro Pro Val Leu Lys Ser Asp Gly Ser Phe Phe Leu Tyr
            180                 185                 190 agc aag ctc acc gtg gac aag agc agg tgg cag cag ggg aac gtc ttc         624
Ser Lys Leu Thr Val Asp Lys Ser Arg Trp Gln Gln Gly Asn Val Phe
        195                 200                 205 tca tgc tcc gtg atg cat gag gct ctg cac aac cac tac acg cag aag         672
Ser Cys Ser Val Met His Glu Ala Leu His Asn His Tyr Thr Gln Lys
    210                 215                 220 agc ctc tcc ctg tct ccg ggt aaa tga                                     699
Ser Leu Ser Leu Ser Pro Gly Lys
225                 230

<210> SEQ ID NO 41
<211> LENGTH: 232
<212> TYPE: PRT
<213> ORGANISM: Homo sapiens

<400> SEQUENCE: 41

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Tyr Pro Arg Glu Glu Gln
65                  70                  75                  80

Trp Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Lys Glu Met Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Lys Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205
```

```
Ser Cys Ser Val Met His Glu Ala Leu His Asn His Tyr Thr Gln Lys
    210                 215                 220
Ser Leu Ser Leu Ser Pro Gly Lys
225                 230
```